United States Patent
Nakayama et al.

(10) Patent No.: US 10,550,141 B2
(45) Date of Patent: Feb. 4, 2020

(54) TETRADENTATE LIGAND, AND PRODUCTION METHOD THEREFOR, SYNTHETIC INTERMEDIATE THEREOF, AND TRANSITION METAL COMPLEX THEREOF

(71) Applicant: TAKASAGO INTERNATIONAL CORPORATION, Tokyo (JP)

(72) Inventors: Yuji Nakayama, Kanagawa (JP); Naota Yokoyama, Kanagawa (JP)

(73) Assignee: TAKASAGO INTERNATIONAL CORPORATION, Tokyo (JP)

(*) Notice: Subject to any disclaimer, the term of this patent is extended or adjusted under 35 U.S.C. 154(b) by 0 days.

(21) Appl. No.: 16/089,730

(22) PCT Filed: Mar. 30, 2017

(86) PCT No.: PCT/JP2017/013435
§ 371 (c)(1),
(2) Date: Sep. 28, 2018

(87) PCT Pub. No.: WO2017/170952
PCT Pub. Date: Oct. 5, 2017

(65) Prior Publication Data
US 2019/0127407 A1 May 2, 2019

(30) Foreign Application Priority Data
Mar. 30, 2016 (JP) .................. 2016-067534

(51) Int. Cl.
| | | |
|---|---|---|
| C07F 15/00 | (2006.01) | |
| B01J 31/22 | (2006.01) | |
| C07D 263/22 | (2006.01) | |
| C07B 53/00 | (2006.01) | |
| C07D 263/38 | (2006.01) | |
| C07F 9/50 | (2006.01) | |
| C07F 15/02 | (2006.01) | |
| C07C 319/14 | (2006.01) | |
| C07C 323/25 | (2006.01) | |
| C07C 323/29 | (2006.01) | |

(52) U.S. Cl.
CPC .......... *C07F 15/0053* (2013.01); *B01J 31/22* (2013.01); *C07B 53/00* (2013.01); *C07C 319/14* (2013.01); *C07C 323/25* (2013.01); *C07C 323/29* (2013.01); *C07D 263/22* (2013.01); *C07D 263/38* (2013.01); *C07F 9/5022* (2013.01); *C07F 15/025* (2013.01); *B01J 2531/0216* (2013.01); *B01J 2531/821* (2013.01); *B01J 2531/822* (2013.01); *B01J 2531/825* (2013.01); *B01J 2531/842* (2013.01)

(58) Field of Classification Search
CPC ........ C07F 15/0053; C07F 9/50; C07F 15/00; C07F 15/02; B01J 31/22; C07C 319/14; C07C 323/25; C07D 263/22

USPC .......................................................... 544/64
See application file for complete search history.

(56) References Cited

U.S. PATENT DOCUMENTS

| | | |
|---|---|---|
| 2010/0063294 A1 | 3/2010 | Kuriyama et al. |
| 2013/0006020 A1 | 1/2013 | Kuriyama et al. |

FOREIGN PATENT DOCUMENTS

| | | |
|---|---|---|
| JP | 07-173132 A | 7/1995 |
| JP | 2011-37809 A | 2/2011 |
| JP | 5477557 B2 | 4/2014 |

OTHER PUBLICATIONS

Written Opinion (PCT/ISA/237) issued by the International Searching Authority in corresponding International Application No. PCT/JP2017/013435, dated Jun. 13, 2017.
International Search Report (PCT/ISA/210), issued by International Searching Authority in corresponding International Application No. PCT/JP2017/013435, dated Jun. 13, 2017.
Lionel A. Saudan et al. "Dihydrogen Reduction of Carboxylic Esters to Alcohols under the Catalysis of Homogeneous Ruthenium Complexes: High Efficiency and Unprecedented Chemoselectivity" Angew. Chem. Int. Ed., 2007, vol. 46, (pp. 7473-7476).
Ruth Patchett et al. "Asymmetric Hydrogenation of Ketones with $H_2$ and Ruthenium Catalysts Containing Chiral Tetradentate $S_2N_2$ Ligands" Angew. Chem. Int. Ed., vol. 52, 2013 (pp. 10352-10355).
Tianshu Li et al. "Dihydridoamine and Hydridoamido Complexes of Ruthenium(II) with a Tetradentate PNNP Donor Ligand" Organometallics, vol. 23, No. 26, 2004 (pp. 6239-6247).
Michael Quirmbach et al. "Synthesis of heterofunctionalized multidentate diphosphines" Tetrahedron, vol. 56, 2000 (pp. 775-780).

(Continued)

*Primary Examiner* — Kahsay Habte
(74) *Attorney, Agent, or Firm* — Sughrue Mion, PLLC

(57) ABSTRACT

The present invention relates to: a compound as a ligand in a variety of catalytic organic synthetic reactions; a method for producing the compound; a synthetic intermediate of the compound; and a transition metal complex which has the compound as a ligand. The compound includes a compound represented by the following general formula ($1^A$):

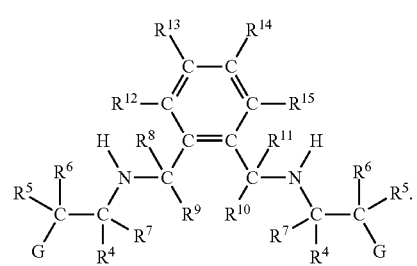

9 Claims, No Drawings

(56) References Cited

OTHER PUBLICATIONS

M. M. Taqui Khan et al. "Synthesis and characterization of dinuclear Cu(I) complexes with two bimetallic hexadentate ligands having $N_2P_4$ donor sites. Crystal structure of $[Cu_2(BDPE)Cl_2]$ 2DMF" Inorganica Chemica Acta, vol. 183, 1991 (pp. 229-237).
Communication dated Oct. 17, 2019, from the European Patent Office in counterpart European Application No. 17775486.8.

TETRADENTATE LIGAND, AND PRODUCTION METHOD THEREFOR, SYNTHETIC INTERMEDIATE THEREOF, AND TRANSITION METAL COMPLEX THEREOF

TECHNICAL FIELD

The present invention relates to a novel tetradentate ligand, its production method and synthetic intermediate, and a transition metal complex of the tetradentate ligand.

BACKGROUND ART

Nowadays, various transition metal complexes each composed of a transition metal and a ligand are aggressively used as a catalyst in organic synthesis reactions. It is known that not only the type of the transition metal but also the ligand, i.e., an organic compound containing a group having a lone electron pair (coordinating group) capable of coordinating to a metal species, plays a very important role as a factor of exhibiting the performance and activity of the catalyst above.

Of these ligands, an organic compound having four coordinating groups (tetradentate ligand) forms three chelate rings at the time of coordination and therefore has a characteristic such that its metal complex is highly stabilized. Furthermore, in a metal complex having a regular octahedral structure, the tetradentate ligand can be coordinated not only in the trans fashion but also in the cis-α/cis-β fashion and thus can induce a new asymmetric environment in the metal center.

In this way, the tetradentate ligand exhibits an interesting coordination behavior and therefore, occupies an important position in the field of complex chemistry, catalyst chemistry, organic synthesis chemistry, etc., and researches and developments thereof are still actively conducted at present. The tetradentate ligand structures reported are so far extended from a simple one capable of being synthesized in a short process to a complicated one requiring a multi-stage reaction, but from the industrial viewpoint, a tetradentate ligand with a simpler structure enabling easy large-scale synthesis is preferred.

As an example of such a tetradentate ligand, a dehydrative condensate of 2-diphenylphosphinobenzaldehyde and an ethylenediamine derivative is known to behave as a PNNP (phosphorus-nitrogen-nitrogen-phosphorus) tetradentate ligand for metal species. It has been reported that a ruthenium complex of the PNNP tetradentate ligand above exhibits good catalytic activity, for example, in a hydrogenation reaction of esters (Patent Document 1 and Non-Patent Document 1).

Furthermore, in recent years, it has been reported that a dehydrative condensate of an ethylenediamine derivative and 2-alkylthiobenzaldehyde capable of being synthesized from inexpensively available 2-nitrobenzaldehyde also functions as an SNNS (sulfur-nitrogen-nitrogen-sulfur) tetradentate ligand, and that a ruthenium complex of this SNNS tetradentate ligand can be an excellent catalyst in an asymmetric hydrogenation reaction of ketones (Non-Patent Document 2).

PRIOR ART LITERATURE

Patent Document

Patent Document 1: Japanese Patent No. 5,477,557

Non-Patent Document

Non-Patent Document 1: Lionel A. Saudan, Christophe M. Saudan, Catherine Debieux, and Patrick Wyss, Angew. Chem. Int. Ed., 2007, 46, 7473-7476.

Non-Patent Document 2: Ruth Patchett, Iris Magpantay, Lionel Saudan, Christoph Schotes, Antonio Mezzetti, and Francesco Santoro, Angew. Chem. Int. Ed., 2013, 52, 10352-10355.

SUMMARY OF THE INVENTION

Problems that the Invention is to Solve

As described above, researches and developments of a tetradentate ligand with a simpler structure enabling easy large-scale synthesis and a ruthenium complex thereof have advanced to a certain extent, but the hydrogenation reaction of esters described in Patent Document 1 and Non-Patent Document 1 has problems not only that a high-pressure (5 MPa) hydrogen gas is required but also that 2-diphenylphosphinobenzaldehyde as a raw material of the PNNP tetradentate ligand is relatively expensive.

Furthermore, also in the asymmetric hydrogenation reaction of ketones described in Non-Patent Document 2, a high-pressure hydrogen gas of 5 MPa is necessary and moreover, there is no example of application to a hydrogenation reaction of esters having poorer reactivity than that of ketones. Accordingly, with respect to a PNNP tetradentate ligand or SNNS tetradentate ligand of simple structure, which are widely used at present, large-scale synthesis in industry may be possible, but this technique still has room for improvement in terms of insufficient catalytic activity of a transition metal complex thereof or the raw material cost.

The present invention has been made in consideration of these circumstances. More specifically, an object of the present invention is to provide a tetradentate ligand exhibiting an interesting coordination behavior for metal species and giving a transition metal complex thereof with high catalytic activity, and a simple and efficient production method for the tetradentate ligand.

Means for Solving the Problems

As a result of intensive studies so as to attain the object above, the present inventors have found that 1) a novel synthetic intermediate is readily obtained by a reaction between easily available α,α'-dibromo-o-xylene and 2-oxazolidone that is easily available as well, and 2) various novel PNNP tetradentate ligands and novel SNNS tetradentate ligands can be synthesized with high yield by a reaction between the synthetic intermediate above and secondary phosphine, secondary phosphine-boron trihydride complex or thiol, of which various derivatives are available (an outline of the reaction formula is shown in Eq. 1 below, but the present invention is not limited to this outline in any way).

[Chem. 1]

Eq. 1

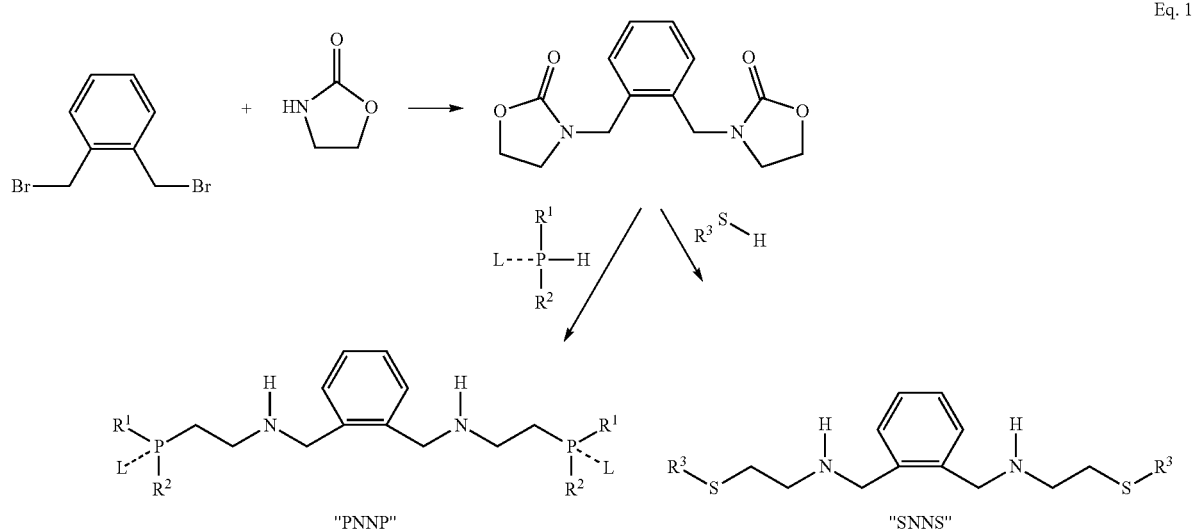

"PNNP"    "SNNS"

Furthermore, it has been found that 3) ruthenium complexes of these tetradentate ligands have a characteristic coordination form such as cis-α/cis-β and 4) these ruthenium complexes exhibit excellent catalytic activity not only in a hydrogenation reaction of esters but also in a hydrogenation reaction of amides, lactones, nitriles, and the like. The present inventors have further advanced studies based on the fundamental knowledge above and have accomplished the present invention.

That is, the present invention includes the following [1] to [10].

[1] A compound represented by the following general formula ($1^A$):

[Chem. 2]

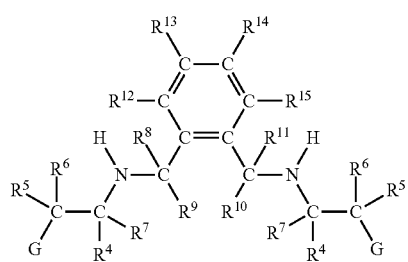

[wherein the solid lines represent single bonds and the double lines represent double bonds, C represents a carbon atom, H represents a hydrogen atom and N represents a nitrogen atom, each of $R^4$, $R^5$, $R^6$, $R^7$, $R^8$, $R^9$, $R^{10}$, $R^{11}$, $R^{12}$, $R^{13}$, $R^{14}$, and $R^{15}$ independently represents a group selected from the group consisting of a hydrogen atom, an alkyl group, a cycloalkyl group, an aryl group, and an aralkyl group, and G represents a group selected from the group consisting of a monovalent group represented by the following general formula ($G^P$):

[Chem. 3]

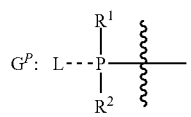

(wherein the solid lines represent single bonds, the dotted line represents a coordinate bond and the solid line intersected by a wavy line represents a bond to an adjacent atom, P represents a phosphorus atom, L represents a lone electron pair or a boron trihydride, each of $R^1$ and $R^2$ independently represents a group selected from the group consisting of an alkyl group, a cycloalkyl group, an alkenyl group that may have a substituent, an aryl group that may have a substituent, a heteroaryl group that may have a substituent, and an aralkyl group that may have a substituent, and $R^1$ and $R^2$ may combine with each other to form a phosphorus atom-containing ring that may have a substituent) and a monovalent group represented by the following general formula ($G^S$):

[Chem. 4]

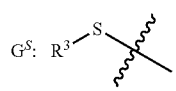

(wherein the solid line represents a single bond and the solid line intersected by a wavy line represents a bond to an adjacent atom, S represents a sulfur atom, and $R^3$ represents a group selected from the group consisting of an alkyl group, a cycloalkyl group, an alkenyl group that may have a substituent, an aryl group that may have a substituent, a heteroaryl group that may have a substituent, and an aralkyl group that may have a substituent)].

[2] The compound according to [1] above, wherein all of the $R^5$ to $R^{15}$ are hydrogen atoms.

[3] The compound according to [1] or [2] above, which is an optically active substance.

[4] A method for producing the compound according to any one of [1] to [3] above, including subjecting a compound represented by the following general formula ($2^A$):

[Chem. 5]

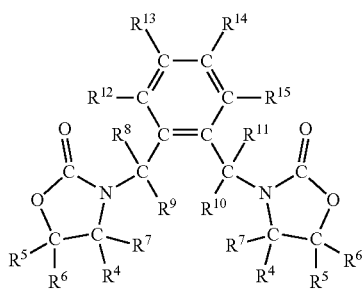

(wherein the solid lines represent single bonds and the double lines represent double bonds, C represents a carbon atom, N represents a nitrogen atom, O represents an oxygen atom, and each of $R^4$, $R^5$, $R^6$, $R^7$, $R^8$, $R^9$, $R^{10}$, $R^{11}$, $R^{12}$, $R^{13}$, $R^{14}$, and $R^{15}$ independently represents a group selected from the group consisting of a hydrogen atom, an alkyl group, a cycloalkyl group, an aryl group, and an aralkyl group) to a reaction with a compound represented by the following general formula (3):

[Chem. 6]

    3

(wherein the solid line represents a single bond, H represents a hydrogen atom, and G represents the same group as G defined in [1] above).

[5] A compound represented by the following general formula ($2^A$):

[Chem. 7]

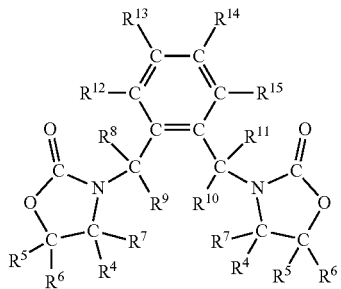

(wherein the solid lines represent single bonds and the double lines represent double bonds, C represents a carbon atom, N represents a nitrogen atom, O represents an oxygen atom, and each of $R^4$, $R^5$, $R^6$, $R^7$, $R^8$, $R^9$, $R^{10}$, $R^{11}$, $R^{12}$, $R^{13}$, $R^{14}$, and $R^{15}$ independently represents a group selected from the group consisting of a hydrogen atom, an alkyl group, a cycloalkyl group, an aryl group, and an aralkyl group).

[6] The compound according to [5] above, wherein all of the $R^5$ to $R^{15}$ are hydrogen atoms.

[7] The compound according to [5] or [6] above, which is an optically active substance.

[8] A transition metal complex, containing the compound according to any one of [1] to [3] above as a ligand.

[9] The transition metal complex according to [8] above, containing a metal species selected from the group consisting of transition metals of Groups 8 to 11.

[10] The transition metal complex according to [9] above, wherein the metal species is a metal species selected from transition metals of Group 8.

Advantage of the Invention

The novel compound represented by general formula ($1^A$) of the present invention can be easily synthesized with high yield by subjecting the novel compound represented by general formula ($2^A$) of the present invention to a reaction with a compound represented by general formula (3). Furthermore, this compound acts as a tetradentate ligand, and a transition metal complex obtained by the reaction with various transition metal compounds exhibits excellent catalytic activity in a variety of organic synthesis reactions.

For example, a ruthenium complex having a compound represented by general formula ($1^A$) as a ligand exhibits excellent catalytic activity in a hydrogenation reaction of esters, compared with a ruthenium complex having a conventional tetradentate ligand capable of being simply and easily produced, and therefore, primary alcohols having high industrial value can be efficiently produced by the reaction thereof.

In addition, when a hydrogenation reaction of amides, halogenated esters, unsaturated esters, lactones, and nitriles is performed by using a ruthenium complex having a compound represented by general formula ($1^A$) as a ligand, not only primary alcohols but also a useful compound such as halogenated alcohols, unsaturated alcohols, diols, and primary amines can be produced with high selectivity and high yield.

MODE FOR CARRYING OUT THE INVENTION

[Compound Represented by General Formula ($1^A$)]

The compound represented by general formula ($1^A$) (hereinafter referred to as the compound ($1^A$) of the present invention) is described in detail below.

In general formula ($1^A$), the solid lines represent single bonds and the double lines represent double bonds. C represents a carbon atom, H represents a hydrogen atom and N represents a nitrogen atom. Each of $R^4$, $R^5$, $R^6$, $R^7$, $R^8$, $R^9$, $R^{10}$, $R^{11}$, $R^{12}$, $R^{13}$, $R^{14}$, and $R^{15}$ independently represents a group selected from the group consisting of a hydrogen atom, an alkyl group, a cycloalkyl group, an aryl group, and an aralkyl group. G represents a group selected from the group consisting of a monovalent group represented by the general formula ($G^P$) above and a monovalent group represented by the general formula ($G^S$) above. In general formulae ($G^P$) and ($G^S$), the solid lines represent single bonds, the dotted line represents a coordinate bond and the solid line intersected by a wavy line represents a bond to an adjacent atom. P represents a phosphorus atom and S represents a sulfur atom. L represents a lone electron pair or a boron trihydride. Each of $R^1$, $R^2$ and $R^3$ independently represents a group selected from the group consisting of an alkyl group, a cycloalkyl group, an alkenyl group that may have a substituent, an aryl group that may have a substituent, a heteroaryl group that may have a substituent, and an aralkyl group that may have a substituent, and preferably represents a group selected from the group consisting of an alkyl group, a cycloalkyl group, and an aryl group that may have a substituent.

The alkyl group in $R^1$ to $R^3$ may be linear or branched and examples thereof include an alkyl group having 1 to 30 carbon atoms, preferably an alkyl group having 1 to 20 carbon atoms, more preferably an alkyl group having 1 to 10 carbon atoms, and specifically includes a methyl group, an ethyl group, an n-propyl group, a 2-propyl group, an n-butyl group, a 2-butyl group, an isobutyl group, a tert-butyl group, an n-pentyl group, a 2-pentyl group, a 3-pentyl group, a 2-methylbutyl group, a 3-methylbutyl group, a 2-methylbutan-2-yl group, a 2-methylbutan-3-yl group, a 2,2-dimethylpropyl group, an n-hexyl group, a 2-hexyl group, a 3-hexyl group, a 2-methylpentyl group, a 3-methylpentyl group, a 4-methylpentyl group, a 2-methylpentan-2-yl group, a 2-methylpentan-3-yl group, a 2-methylpentan-4-yl group, a 3-methylpentan-2-yl group, a 3-methylpentan-3-yl group, a 2,2-dimethylbutyl group, a 3,3-dimethylbutyl group, a 2,2-dimethylbutan-3-yl group, an n-heptyl group, an n-octyl group, an n-nonyl group, and an n-decyl group, and preferable specific examples thereof include a methyl group.

Examples of the cycloalkyl group in $R^1$ to $R^3$ include a cycloalkyl group having 3 to 30 carbon atoms, preferably a cycloalkyl group having 3 to 20 carbon atoms, more preferably a cycloalkyl group having 3 to 10 carbon atoms, and specifically include a cyclopropyl group, a cyclobutyl group, a cyclopentyl group, a cyclohexyl group, a 1-adamantyl group, and a 2-adamantyl group, and preferable specific examples thereof include a cyclohexyl group.

The alkenyl group in $R^1$ to $R^3$ may be linear, branched or cyclic and examples thereof include an alkenyl group having 2 to 20 carbon atoms, preferably an alkenyl group having 2 to 14 carbon atoms, more preferably an alkenyl group having 2 to 8 carbon atoms, and specifically include a vinyl group, a 1-propenyl group, a 2-propenyl group, an allyl group, a 1-cyclohexenyl group, a 1-styryl group, and a 2-styryl group.

Examples of the aryl group in $R^1$ to $R^3$ include an aryl group having 6 to 18 carbon atoms, preferably an aryl group having 6 to 14 carbon atoms, more preferably an aryl group having 6 to 10 carbon atoms, and specifically include a phenyl group, a 1-naphthyl group, and a 2-naphthyl group, and preferable specific examples thereof include a phenyl group.

Examples of the heteroaryl group in $R^1$ to $R^3$ include heteroaryl groups derived from a 5-membered aromatic heterocycle containing an oxygen atom or a sulfur atom and from a polycyclic aromatic heterocycle produced by ring-fusing the aromatic heterocycle with the aryl group above, and specifically include a 2-furyl group, a 3-furyl group, a 2-thienyl group, a 3-thienyl group, a 2-benzofuryl group, a 3-benzofuryl group, a 2-benzothienyl group, and a 3-benzothienyl group.

Examples of the aralkyl group in $R^1$ to $R^3$ include an aralkyl group formed by substituting at least one hydrogen atom of the alkyl group or cycloalkyl group above by the aryl group above and a polycyclic aralkyl group formed by ring-fusing the cycloalkyl group above with the aryl group above, and specifically include a benzyl group, a 1-phenylethyl group, a 2-phenylethyl group, a 1-phenylpropyl group, a 2-phenylpropyl group, a 3-phenylpropyl group, a 1-phenyl-2-propyl group, a 2-phenyl-2-propyl group, a 1-indanyl group, a 2-indanyl group, and a 9-fluorenyl group.

$R^1$ and $R^2$ may combine with each other to form a phosphorus atom-containing ring that may have a substituent. Specific examples of the phosphorus atom-containing ring include a phosphorane ring, a 1H-phosphole ring, a phosphinane ring, a 1,2-dihydrophosphinine ring, a phosphepane ring, and a 1H-phosphepine ring.

Examples of the substituent that may be substituted on the alkenyl group, aryl group, heteroaryl group, and aralkyl group in $R^1$ to $R^3$ and on the phosphorus atom-containing ring formed by combining $R^1$ and $R^2$ with each other, include an alkyl group, a cycloalkyl group, a halogenoalkyl group, an aryl group, an aralkyl group, an alkoxy group, a silyl group, and a halogeno group. Of these substituents, the alkyl group, cycloalkyl group, aryl group and aralkyl group include the same groups as the groups described in detail in the description of $R^1$ to $R^3$ above.

Examples of the halogenoalkyl group as the substituent include a group formed by substituting at least one hydrogen atom of the alkyl group above by a halogen atom, and specifically include a trifluoromethyl group and a nonafluorobutyl group.

Examples of the alkoxy group as the substituent include an alkoxy group having 1 to 10 carbon atoms, preferably an alkoxy group having 1 to 4 carbon atoms, and specifically include a methoxy group, an ethoxy group, a 1-propoxy group, a 2-propoxy group, a 1-butoxy group, a 2-butoxy group, and a tert-butoxy group.

Examples of the silyl group as the substituent include, for example, a silyl group having 3 to 36 carbon atoms, preferably a silyl group having 3 to 18 carbon atoms, and specifically include a trimethylsilyl group, a triethylsilyl group, a tert-butyldimethylsilyl group, a tri(2-propyl)silyl group, a tert-butyldiphenylsilyl group, and a triphenylsilyl group.

Examples of the halogeno group as the substituent specifically include a fluoro group, a chloro group, a bromo group, and an iodo group, and preferably include a fluoro group and a chloro group.

The alkyl group in $R^4$ to $R^{15}$ may be linear or branched and examples thereof include an alkyl group having 1 to 20 carbon atoms, preferably an alkyl group having 1 to 10 carbon atoms, more preferably an alkyl group having 1 to 6 carbon atoms, and specifically include a methyl group, an ethyl group, an n-propyl group, a 2-propyl group, an n-butyl group, a 2-butyl group, an isobutyl group, a tert-butyl group, an n-pentyl group, a 2-pentyl group, a 3-pentyl group, a 2-methylbutyl group, a 3-methylbutyl group, a 2-methylbutan-2-yl group, a 2-methylbutan-3-yl group, a 2,2-dimethylpropyl group, an n-hexyl group, a 2-hexyl group, a 3-hexyl group, a 2-methylpentyl group, a 3-methylpentyl group, a 4-methylpentyl group, a 2-methylpentan-2-yl group, a 2-methylpentan-3-yl group, a 2-methylpentan-4-yl group, a 3-methylpentan-2-yl group, a 3-methylpentan-3-yl group, a 2,2-dimethylbutyl group, a 3,3-dimethylbutyl group, and a 2,2-dimethylbutan-3-yl group, and preferable specific examples thereof include a 2-propyl group.

Examples of the cycloalkyl group in $R^4$ to $R^{15}$ include a cycloalkyl group having 3 to 20 carbon atoms, preferably a cycloalkyl group having 3 to 10 carbon atoms, more preferably a cycloalkyl group having 3 to 6 carbon atoms, and specifically include a cyclopropyl group, a cyclobutyl group, a cyclopentyl group, and a cyclohexyl group.

Examples of the aryl group in $R^4$ to $R^{15}$ include an aryl group having 6 to 18 carbon atoms, preferably an aryl group having 6 to 14 carbon atoms, more preferably an aryl group having 6 to 10 carbon atoms, and specifically include a phenyl group, a 1-naphthyl group, and a 2-naphthyl group, and preferable specific examples thereof include a phenyl group.

Examples of the aralkyl group in $R^4$ to $R^{15}$ include an aralkyl group formed by substituting at least one hydrogen atom of the alkyl group above by the aryl group above, and specifically include a benzyl group, a 1-phenylethyl group, a 2-phenylethyl group, a 1-phenylpropyl group, a 2-phenylpropyl group, a 3-phenylpropyl group, a 1-phenyl-2-propyl group, and a 2-phenyl-2-propyl group, and preferable specific examples thereof include a benzyl group.

The compound ($1^A$) of the present invention may be an optically active substance. A more preferred embodiment of the compound ($1^A$) of the present invention is specifically a compound where in general formula ($1^A$), all of $R^5$ to $R^{15}$ are a hydrogen atom, represented by the following general formula ($1^B$):

[Chem. 8]

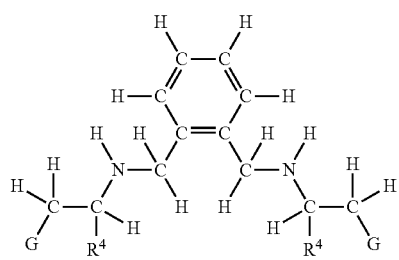

$1^B$ (wherein the solid lines, double lines, C, H, N, $R^4$, and G are the same as the solid lines, double lines, C, H, N, $R^4$, and G defined in general formula ($1^A$)) (hereinafter referred to as compound ($1^B$)).

The particularly preferred embodiment of the compound ($1^A$) of the present invention specifically includes compounds ($1^B$-1) to ((S,S)-$1^B$-8) shown below.

[Chem. 9]

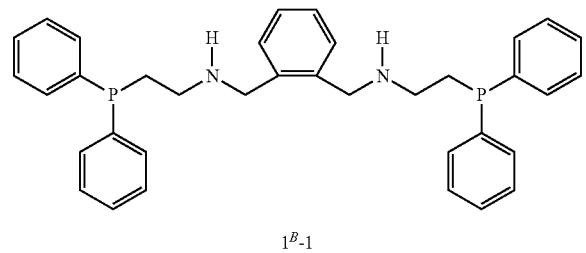

$1^B$-1

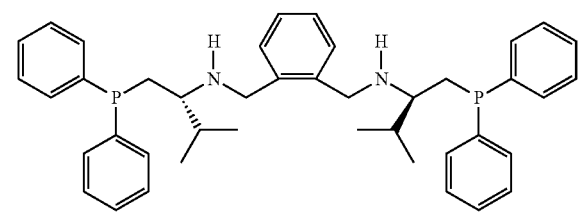

(R,R)-$1^B$-2

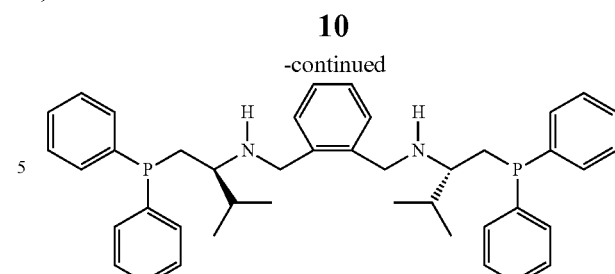

(S,S)-$1^B$-2

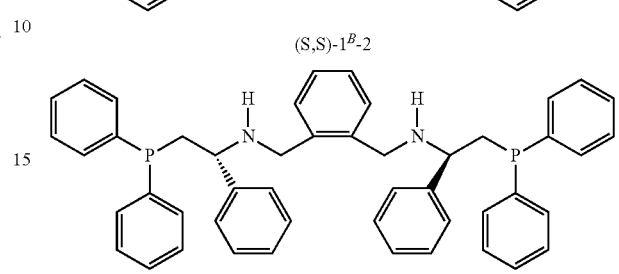

(R,R)-$1^B$-3

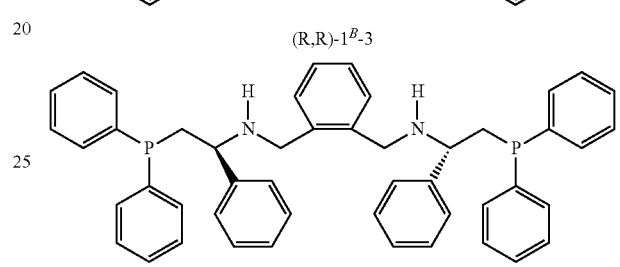

(S,S)-$1^B$-3

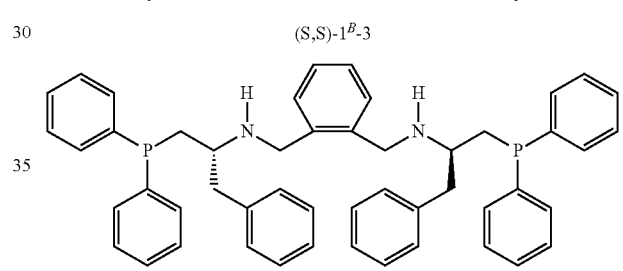

(R,R)-$1^B$-4

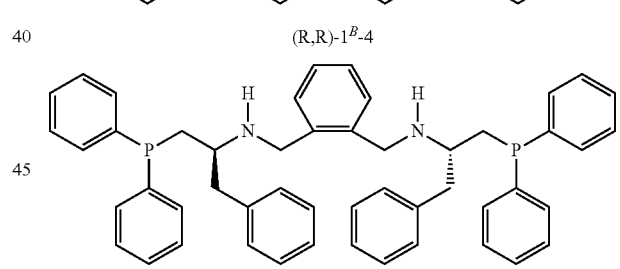

(S,S)-$1^B$-4

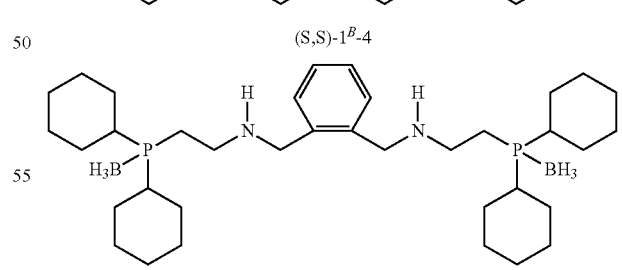

$1^B$-5

$1^B$-6

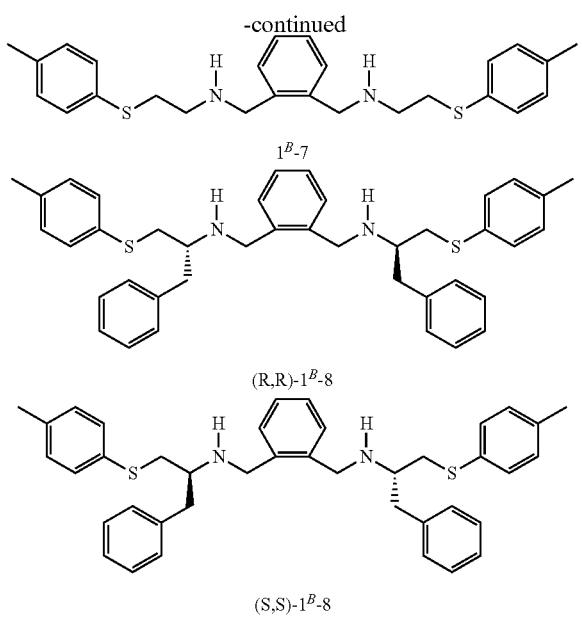

1$^B$-7

(R,R)-1$^B$-8

(S,S)-1$^B$-8

Among the compound (1$^A$) of the present invention, some compounds are unstable to air or some compounds become a highly viscous liquid substance and in turn, are difficult to purify or measure, and therefore, in order to facilitate the handling, a corresponding salt may be formed by the reaction with a Bronsted acid, specifically, hydrohalic acid, perchloric acid, nitric acid, sulfuric acid, sulfonic acid, carboxylic acid, phenols, phosphoric acid, hexafluorophosphoric acid, boric acid, and tetrafluoroboric acid.

Examples of the hydrohalic acid specifically include hydrofluoric acid, hydrochloric acid, hydrobromic acid, and hydroiodic acid. Examples of the sulfonic acid specifically include methanesulfonic acid, trifluoromethanesulfonic acid, p-toluenesulfonic acid, and 10-camphorsulfonic acid. Examples of the carboxylic acid specifically include formic acid, acetic acid, trifluoroacetic acid, benzoic acid, salicylic acid, oxalic acid, and tartaric acid. Examples of the phenols specifically include phenol, p-cresol, p-nitrophenol, and pentafluorophenol.

In the case of using a salt of the compound (1$^A$) of the present invention with a Bronsted acid for the production of a transition metal complex having the compound (1$^A$) of the present invention as a ligand (hereinafter, referred to as the transition metal complex of the present invention), the salt may be used as it is for the reaction, may be subjected to a reaction with a base outside the reaction system to liberate the compound (1$^A$) of the present invention and then used for the reaction, or may be used for the reaction while liberating the compound (1$^A$) of the present invention under the action of a base in the reaction system.

Furthermore, in the case where G in the compound (1$^A$) of the present invention is represented by general formula (G$^P$) and L in general formula (G$^P$) is boron trihydride, in the case of production of the transition metal complex of the present invention, the compound (1$^A$) of the present invention may be used as it is for the reaction, may be used for the reaction after boron trihydride is dissociated outside of the reaction system, or may be used for the reaction while dissociating boron trihydride in the reaction system. For the dissociation of boron trihydride, a dissociating agent is preferably used in combination, and examples of the dissociating agent for boron trihydride include amines such as diethylamine, triethylamine, morpholine, and 1,4-diazabicyclo[2,2,2]octane.

[Compound Represented by General Formula (2$^A$)]

The compound represented by general formula (2$^A$) (hereinafter referred to as the intermediate (2$^A$) of the present invention) working out to a raw material compound of the compound (1$^A$) of the present invention is described below.

In general formula (2$^A$), the solid lines represent single bonds and the double lines represent double bonds. C represents a carbon atom, N represents a nitrogen atom and O represents an oxygen atom. R$^4$ to R$^{15}$ are the same groups as R$^4$ to R$^{15}$ defined in general formula (1$^A$).

The intermediate (2$^A$) of the present invention may be an optically active substance. A more preferred embodiment of the intermediate (2$^A$) of the present invention specifically includes a compound where in general formula (2$^A$), all of R$^5$ to R$^{15}$ are hydrogen atoms, represented by the following general formula (2$^B$):

[Chem. 10]

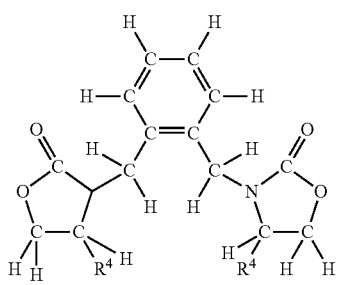

2$^B$ (wherein H represents a hydrogen atom, and the solid lines, double lines, C, N, O, and R$^4$ are the same as the solid lines, double lines, C, H, N, and R$^4$ defined in general formula (2$^A$)) (hereinafter referred to as compound (2$^B$)).

The particularly preferred embodiment of the intermediate (2$^A$) of the present invention specifically includes compounds (2$^B$-1) to ((S,S)-2$^B$-4) shown below.

[Chem. 11]

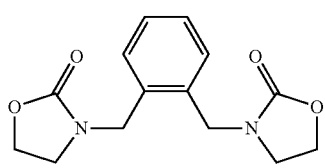

2$^B$-1

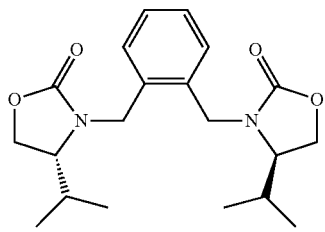

(R,R)-2$^B$-2

-continued (S-S)-2$^B$-2
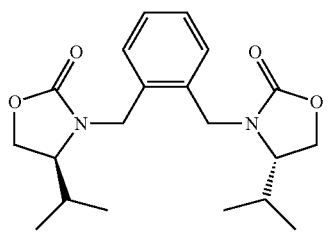

(R,R)-2$^B$-3
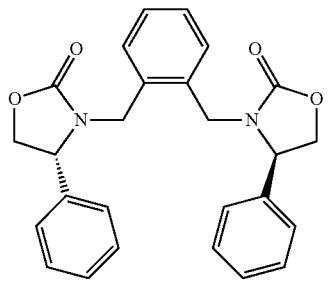

(S,S)-2$^B$-3
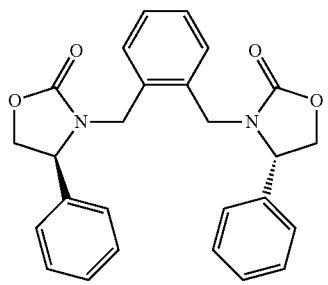

(R,R)-2$^B$-4
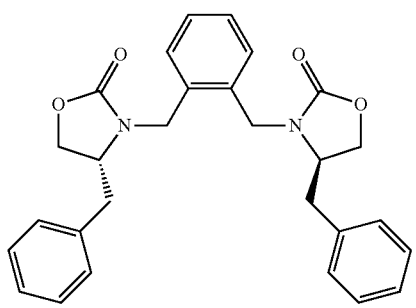

(S,S)-2$^B$-4
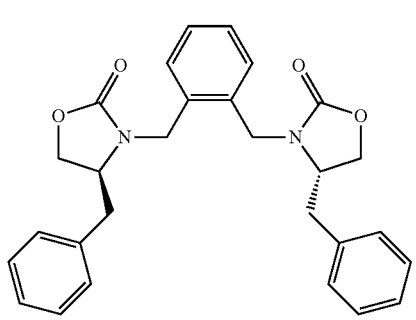

The intermediate (2$^A$) of the present invention can be easily obtained by subjecting a compound represented by the following general formula (4$^A$):

[Chem. 12]

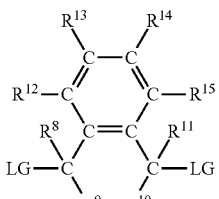

4$^A$ (wherein the solid lines represent single bonds and the double lines represent double bonds, C represents a carbon atom, LG represents a leaving group, and R$^8$ to R$^{15}$ are the same groups as R$^8$ to R$^{15}$ defined in general formula (2$^A$)) (hereinafter, referred to as compound (4$^A$)) to a reaction with a compound represented by the following general formula (5$^A$):

[Chem. 13]

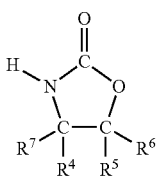

5$^A$ (wherein the solid lines represent single bonds and the double line represents a double bond, C represents a carbon atom, H represents a hydrogen atom, N represents a nitrogen atom, O represents an oxygen atom, and R$^4$ to R$^7$ are the same groups as R$^4$ to R$^7$ defined in general formula (2$^A$)) (hereinafter referred to as compound (5$^A$)) under basic conditions.

In addition, the compound (2$^B$) that is a more preferred embodiment of the intermediate (2$^A$) of the present invention can be easily obtained by subjecting a compound represented by the following general formula (4$^B$):

[Chem. 14]

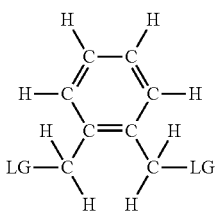

4$^B$ (wherein H represents a hydrogen atom, and the solid lines, double lines, C, and LG are the same as the solid lines, double lines, C, and LG defined in general formula (4$^A$)) (hereinafter referred to as compound (4$^B$)) to a reaction with a compound represented by the following general formula (5$^B$):

[Chem. 15]

$5^B$ (wherein the solid lines, double line, C, H, N, O, and R⁴ are the same as the solid lines, double line, C, H, N, O, and R⁴ defined in general formula ($5^A$)) (hereinafter referred to as compound ($5^B$)) under basic conditions.

In general formulae ($4^A$) and ($4^B$), LG represents a leaving group, preferably a halogeno group and a sulfonyloxy group. Examples of the halogeno group specifically include a fluoro group, a chloro group, a bromo group, and an iodo group, and preferable specific examples thereof include a bromo group. Examples of the sulfonyloxy group specifically include a methanesulfonyloxy group, a p-toluenesulfonyloxy group, and a trifluoromethanesulfonyloxy group.

The particularly preferred embodiment of the compound ($4^A$) specifically includes compound ($4^B$-1) shown below, and the particularly preferred embodiment of the compound ($5^B$) specifically includes compounds ($5^B$-1) to ((S)-$5^B$-4) shown below.

[Chem. 16]

$4^B$-1

$5^B$-1

(R)-$5^B$-2

(S)-$5^B$-2

(R)-$5^B$-3

(S)-$5^B$-3

(R)-$5^B$-4

(S)-$5^B$-4

[Production Method for Compound ($1^A$) of the Present Invention]

The production method of the compound ($1^A$) of the present invention is described in detail below. The compound ($1^A$) of the present invention can be easily obtained by the reaction of the intermediate ($2^A$) of the present invention with a compound represented by general formula (3) (hereinafter, referred to as compound (3)) (Eq. 2).

[Chem. 17]

Eq. 2

$2^A$ + G—H ⟶
        3

-continued $$1^A$$

First, compound (3) is described in more detail by referring to specific examples.

In general formula (3), the solid line represents a single bond. H represents a hydrogen atom. G represents the same group as G defined in general formula ($1^A$).

Compound (3) specifically includes a compound represented by the following general formula ($3^P$):

[Chem. 18]

$$3^P$$

(wherein the solid lines represent single bonds and the dotted line represents a coordinate bond, H represents a hydrogen atom and P represents a phosphorus atom, L represents a lone electron pair or a boron trihydride, and $R^1$ and $R^2$ represent the same groups as $R^1$ and $R^2$ defined in general formula ($1^A$)) (hereinafter, referred to as compound ($3^P$)), namely, secondary phosphine and secondary phosphine-boron trihydride complex, and a compound represented by the following general formula ($3^S$):

[Chem. 19]

$$3^S$$

(wherein the solid lines represent single bonds, H represents a hydrogen atom and S represents a sulfur atom, and $R^3$ represents the same group as $R^3$ defined in general formula ($1^A$)) (hereinafter, referred to as compound ($3^S$)), namely, thiol.

Out of compound ($3^P$), specific examples of the secondary phosphine include dimethylphosphine ($3^P$-1), diethylphosphine ($3^P$-2), diisopropylphosphine ($3^P$-3), di-tert-butylphosphine ($3^P$-4), dicyclopentylphosphine ($3^P$-5), dicyclohexylphosphine ($3^P$-6), di-1-adamantylphosphine ($3^P$-7), tert-butylphenylphosphine ($3^P$-8), diphenylphosphine ($3^P$-9), bis(2-methylphenyl)phosphine ($3^P$-10), bis(4-methylphenyl)phosphine ($3^P$-11), bis(3,5-dimethylphenyl)phosphine ($3^P$-12), bis(2,4,6-trimethylphenyl)phosphine ($3^P$-13), bis(2-methoxyphenyl)phosphine ($3^P$-14), bis(4-methoxyphenyl)phosphine ($3^P$-15), bis[4-(trifluoromethyl)phenyl]phosphine ($3^P$-16), bis[3,5-bis(trifluoromethyl)phenyl]phosphine ($3^P$-17), bis(3,5-di-ten-butyl-4-methoxyphenyl)phosphine ($3^P$-18), (11bS)-4,5-dihydro-3H-dinaphtho[2,1-c: 1',2'-e]phosphepine ($3^P$-19), and di-2-furylphosphine ($3^P$-20), and preferable specific examples thereof include diphenylphosphine ($3^P$-9).

Out of the compound ($3^P$), specific examples of the secondary phosphine-boron trihydride complex include boron trihydride complexes of the secondary phosphines recited as specific examples above, and preferable specific examples thereof include a dicyclohexylphosphine-boron trihydride complex ($3^P$-21).

[Chem. 20]

$$3^P\text{-1}$$

$$3^P\text{-2}$$

$$3^P\text{-3}$$

$$3^P\text{-4}$$

$$3^P\text{-5}$$

$$3^P\text{-6}$$

$$3^P\text{-7}$$

$$3^P\text{-8}$$

$$3^P\text{-9}$$

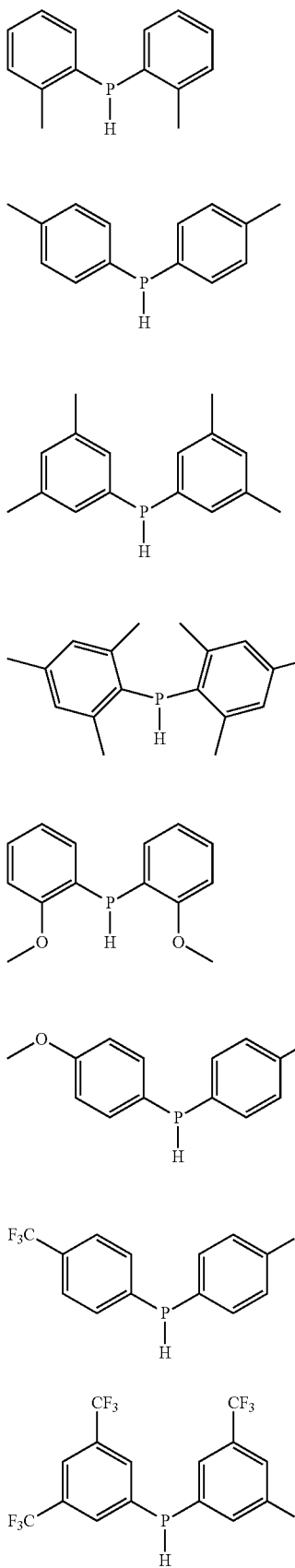

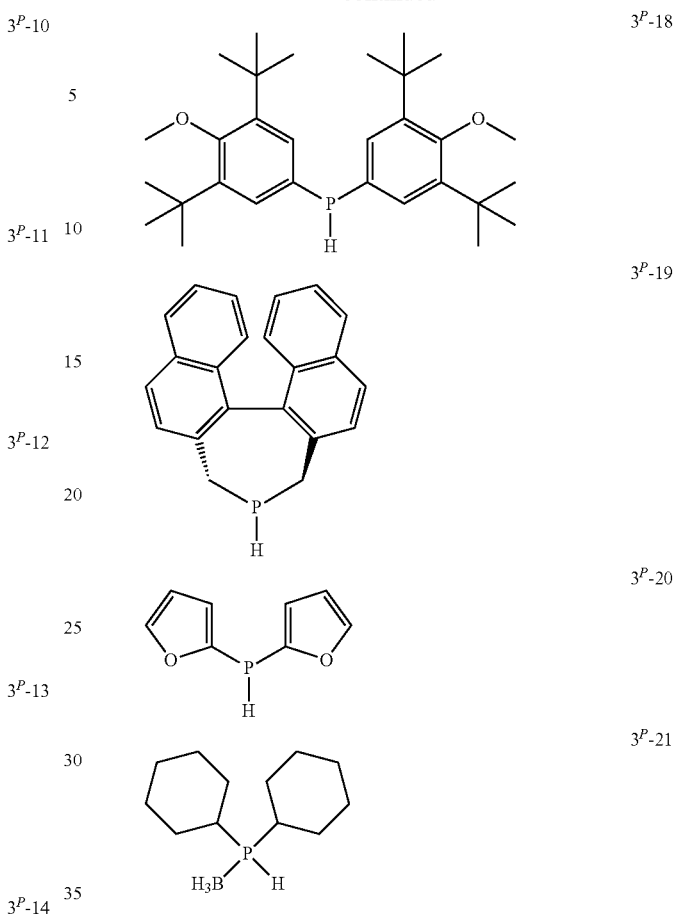

Among the compound ($3^P$), the secondary phosphine is generally unstable to air and therefore, in order to facilitate the handling, a salt may be formed with a Bronsted acid, specifically, tetrafluoroboric acid. The salt of the secondary phosphine with a Bronsted acid may be used for the reaction with the intermediate ($2^A$) of the present invention after liberating the secondary phosphine under the action of a base outside the reaction system or may be used for the reaction with the intermediate ($2^A$) of the present invention while liberating the secondary phosphine under the action of a base in the reaction system.

In the reaction of the intermediate ($2^A$) of the present invention with compound ($3^1$), as a substitute for compound (3), a monovalent anion derived from secondary phosphine (secondary phosphide) or a monovalent anion derived from a boron trihydride complex of secondary phosphine (boron trihydride complex of secondary phosphide) may be used. These secondary phosphide and boron trihydride complex of secondary phosphide can be easily prepared by subjecting compound (3') to a reaction with a base. The secondary phosphide can also be prepared by other reactions, and specific examples thereof include a reaction of a secondary phosphine halide with an alkali metal, a reaction of a secondary phosphine dimer with an alkali metal, and a reaction of a tertiary phosphine with an alkali metal.

Specific examples of compound ($3^S$), i.e., thiol, include methanethiol ($3^S$-1), ethanethiol ($3^S$-2), 1-propanethiol ($3^S$-3), 2-propanethiol ($3^S$-4), 1-butanethiol ($3^S$-5), 2-butanethiol ($3^S$-6), 2-methyl-1-propanethiol ($3^S$-7), 2-methyl-2-propanethiol ($3^S$-8), 1-pentanethiol ($3^S$-9), 3-methyl-1-butanethiol ($3^S$-10), cyclopentanethiol ($3^S$-11), 1-hexanethiol ($3^S$-12), cyclohexanethiol ($3^S$-13), 1-heptanethiol ($3^S$-14), 1-octanethiol ($3^S$-15), 1-nonanethiol ($3^S$-16), 1-decanethiol ($3^S$-17), 1-adamantanethiol ($3^S$-18), benzenethiol ($3^S$-19), o-toluenethiol ($3^S$-20), m-toluenethiol ($3^S$-21), p-toluenethiol ($3^S$-2$_2$), 2,4-dimethylbenzenethiol ($3^S$-23), 2,5-dimethylbenzenethiol ($3^S$-2$_4$), 3,4-dimethylbenzenethiol ($3^S$-25), 3,5-dimethylbenzenethiol ($3^S$-26), 4-isopropylbenzenethiol ($3^S$-27), 4-tert-butylbenzenethiol ($3^S$-28), 2-methoxybenzenethiol ($3^S$-29), 4-methoxybenzenethiol ($3^S$-30), 2,5-dimethoxybenzenethiol ($3^S$-31), 3,4-dimethoxybenzenethiol ($3^S$-32), 2-fluorobenzenethiol ($3^S$-33), 3-fluorobenzenethiol ($3^S$-34), 4-fluorobenzenethiol ($3^S$-35), 2-chlorobenzenethiol ($3^S$-36), 4-chlorobenzenethiol ($3^S$-37), biphenyl-4-thiol ($3^S$-38), 1-naphthalenethiol ($3^S$-39), benzyl mercaptan ($3^S$-40), (2,4,6-trimethylphenyl)methanethiol ($3^S$-41), (4-methoxyphenyl)methanethiol ($3^S$-42), (4-fluorophenyl)methanethiol ($3^S$-43), (2-chlorophenyl)methanethiol ($3^S$-44), (4-chlorophenyl)methanethiol ($3^S$-45), triphenylmnethanethiol ($3^S$-46), and 9-mercaptofluorene ($3^S$-47).

[Chem.21]

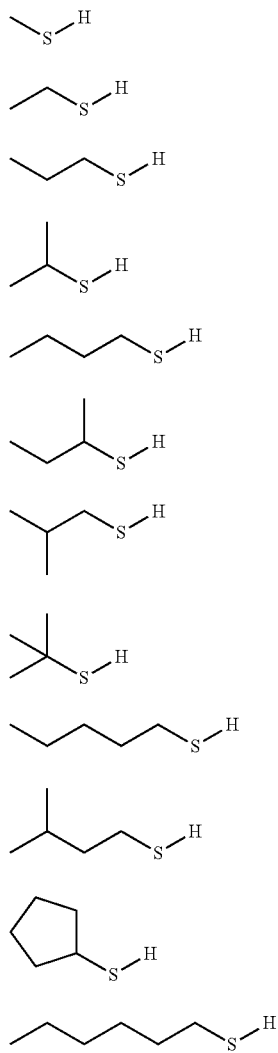

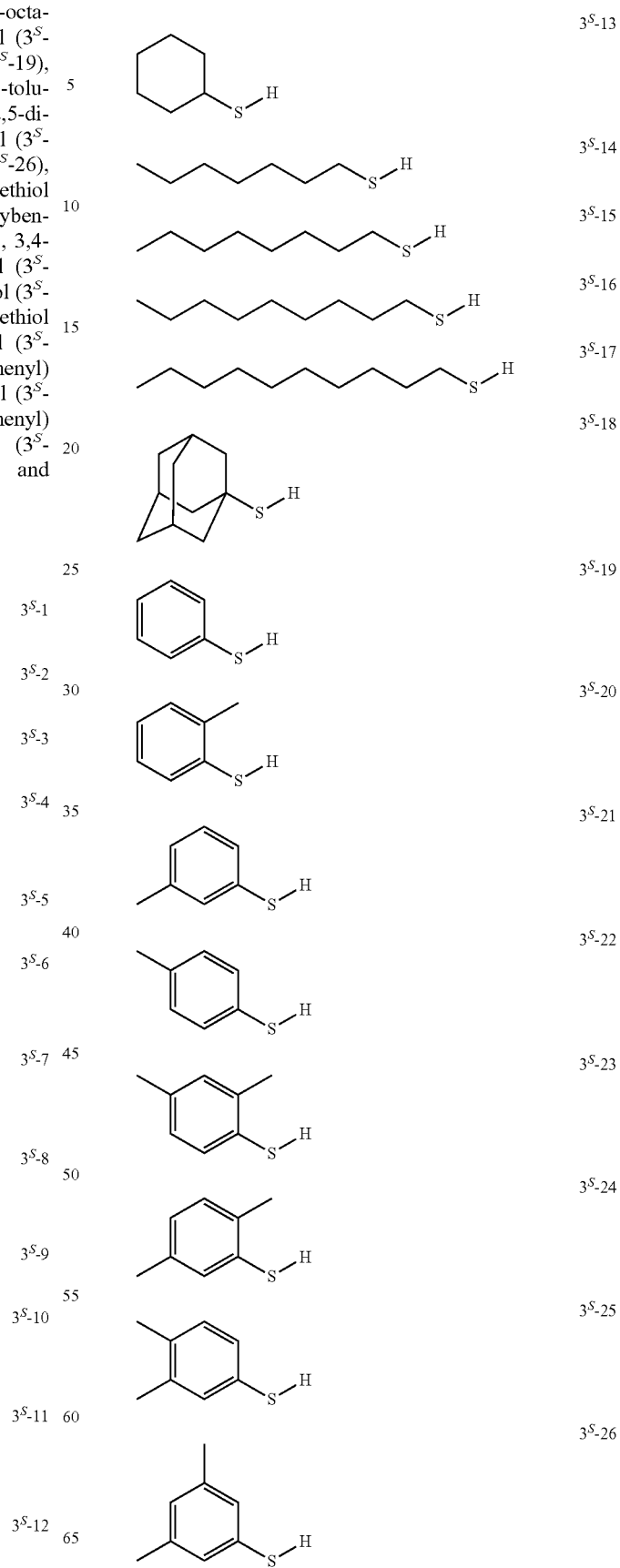

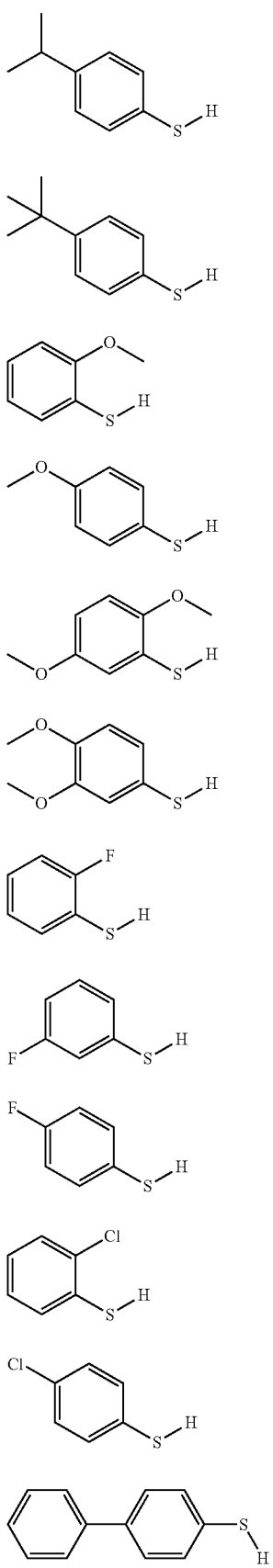
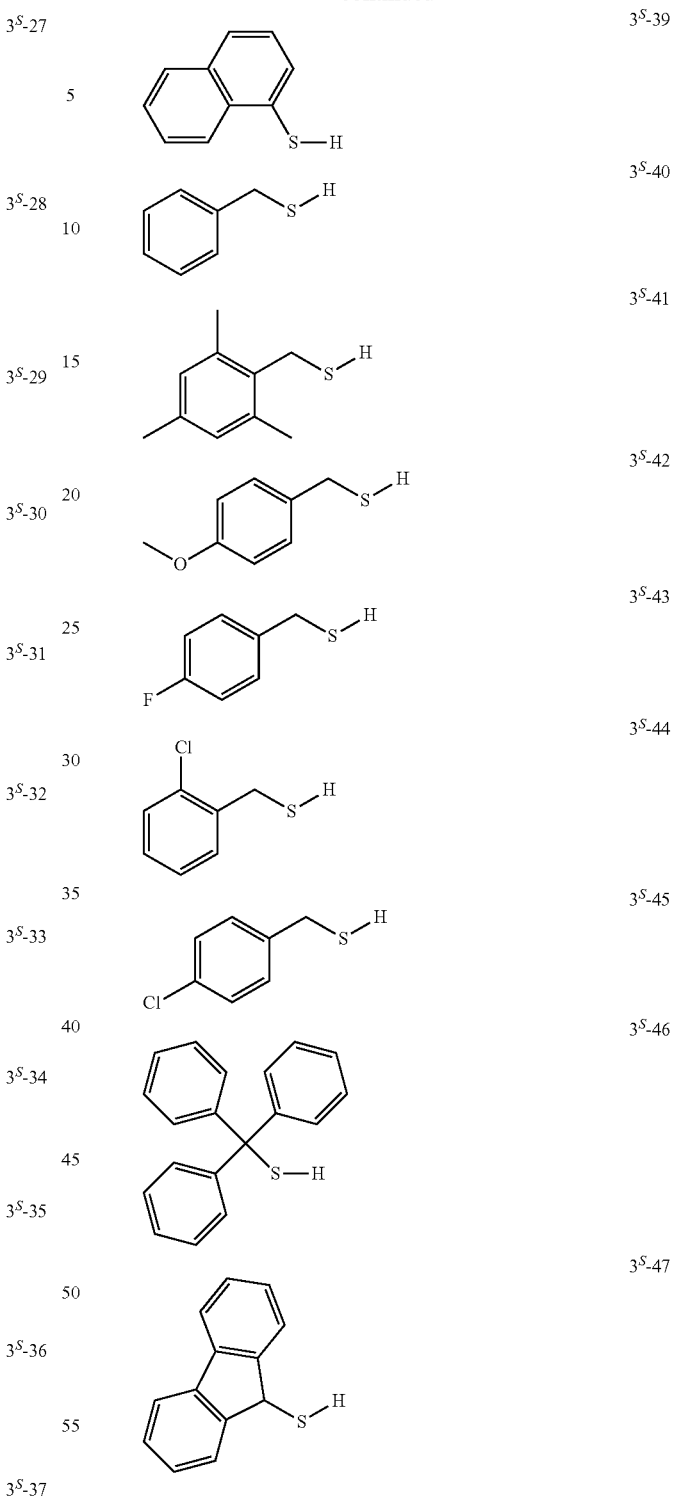

In the reaction of the intermediate ($2^A$) of the present invention with compound (35) i.e., thiol, as a substitute for thiol generally having a strong malodor, a more easily handleable monovalent anion derived from thiol (thiolate) may also be used. The thiolate can be easily prepared by subjecting compound ($3^S$) to a reaction with a base.

Specific examples of the thiolate include alkali metal salts of the thiols recited as specific examples above, and preferable specific examples thereof include sodium salt of methanethiol ($3^S$-1) (sodium methanethiolate) and sodium salt of p-toluenethiol ($3^S$-$2_2$) (sodium p-toluenethiolate).

The reaction of the intermediate ($2^A$) of the present invention with compound (3) may be conducted under any of acidic conditions, neutral conditions and basic conditions, but in view of reactivity, the reaction is preferably conducted under basic conditions.

In the case of conducting the reaction under basic conditions, examples of the preferable base specifically include an alkali metal hydroxide such as lithium hydroxide, sodium hydroxide, and potassium hydroxide, an alkali metal phosphate such as sodium phosphate and potassium phosphate, an alkali metal carbonate such as lithium carbonate, sodium carbonate, and potassium carbonate, an alkali metal carboxylate such as sodium acetate and potassium acetate, an alkaline earth metal hydroxide such as calcium hydroxide, strontium hydroxide, and barium hydroxide, a metal hydride such as lithium hydride, sodium hydride, potassium hydride, calcium hydride, sodium borohydride, and lithium aluminum hydride, an alkali metal alkoxide such as lithium methoxide, sodium methoxide, potassium methoxide, sodium ethoxide, potassium ethoxide, sodium tert-butoxide, and potassium tert-butoxide, an organolithium compound such as methyllithium, n-butyllithium, sec-butyllithium, tert-butyllithium, and phenyllithium, alkali metal amides such as lithium amide, sodium amide, lithium diisopropyl amide, and lithium hexamethyldisilazide, a Grignard reagent such as methylmagnesium chloride, tert-butylmagnesium chloride, phenylmagnesium chloride, phenylmagnesium bromide, and methylmagnesium iodide, amines such as triethylamine, tri-n-butylamine, diisopropylethylamine, N,N-dimethylaniline, 4-dimethylaminopyridine, pyrrolidine, piperidine, N-methylmorpholine, 1,5-diazabicyclo[4.3.0]non-5-ene, and 1,8-diazabicyclo[5.4.0]undec-7-ene, and preferable specific examples thereof include n-butyllithium. Each of these bases may be used alone, or two or more thereof may be used appropriately in combination.

The amount of the base used is not particularly limited but is appropriately selected from the range of usually from 0.3 to 10 equivalents, preferably from 0.5 to 5 equivalents, more preferably from 0.8 to 3 equivalents, relative to compound (3).

The method for adding the base in this reaction is not particularly limited, but each of compound (3) and the base may be added individually, a mixture of compound (3) and the base (and a solvent) may be added, or the secondary phosphide, secondary phosphide-boron trihydride complex, or thiolate, obtained by subjecting compound (3) to a reaction with the base (in a solvent), may be added. Accordingly, in the case of subjecting, as a substitute for compound (3), the secondary phosphide, secondary phosphide-boron trihydride complex or thiolate to a reaction with the intermediate ($2^A$) of the present invention, the reaction may be conducted without adding the base.

The reaction of the intermediate ($2^A$) of the present invention with compound (3) is preferably conducted in the presence of a solvent. Examples of the solvent specifically include aliphatic hydrocarbons such as n-pentane, n-hexane, n-heptane, n-octane, n-decane, cyclohexane, and decalin, aromatic hydrocarbons such as benzene, toluene, xylene, mesitylene, p-cymene, and 1,4-diisopropylbenzene, halogenated aromatic hydrocarbons such as chlorobenzene and o-dichlorobenzene, alcohols such as methanol, ethanol, 2-propanol, n-butanol, tert-butanol, 2-methyl-2-butanol, and 2-ethoxyethanol, polyhydric alcohols such as ethylene glycol, propylene glycol, 1,2-propanediol, and glycerin, ethers such as diethyl ether, diisopropyl ether, tert-butyl methyl ether, cyclopentyl methyl ether, 1,2-dimethoxyethane, ethylene glycol diethyl ether, tetrahydrofuran, and 1,4-dioxane, amides such as formamide, N,N-dimethylformamide, N,N-dimethylacetamide, and N-methylpyrrolidone, nitriles such as acetonitrile and benzonitrile, sulfoxides such as dimethyl sulfoxide, water, and preferable specific examples thereof include n-hexane, tetrahydrofuran, and 2-methyl-2-butanol. Each of these solvents may be used alone, or two or more thereof may be used appropriately in combination.

The amount of the solvent used is not particularly limited but is appropriately selected from the range of usually from 0.5 to 200 times by volume, preferably from 1 to 100 times by volume, more preferably from 2 to 50 times by volume, relative to the intermediate ($2^A$) of the present invention.

This reaction is preferably performed in an inert gas atmosphere. The inert gas specifically includes argon gas and nitrogen gas.

The reaction temperature is appropriately selected from the range of usually from −78° C. to 200° C., preferably from −20° C. to 175° C., more preferably from 0° C. to 150° C.

The reaction time varies depending on the base, the solvent, the reaction temperature, and other conditions but is appropriately selected from the range of usually from 1 minute to 24 hours, preferably from 2 minutes to 12 hours, more preferably from 5 minutes to 8 hours.

Compound ($1^B$) that is a more preferred embodiment of the compound ($1^A$) of the present invention can be synthesized by subjecting compound ($2^B$) to a reaction with compound (3) according to the production method above (Eq. 3).

[Chem. 22]

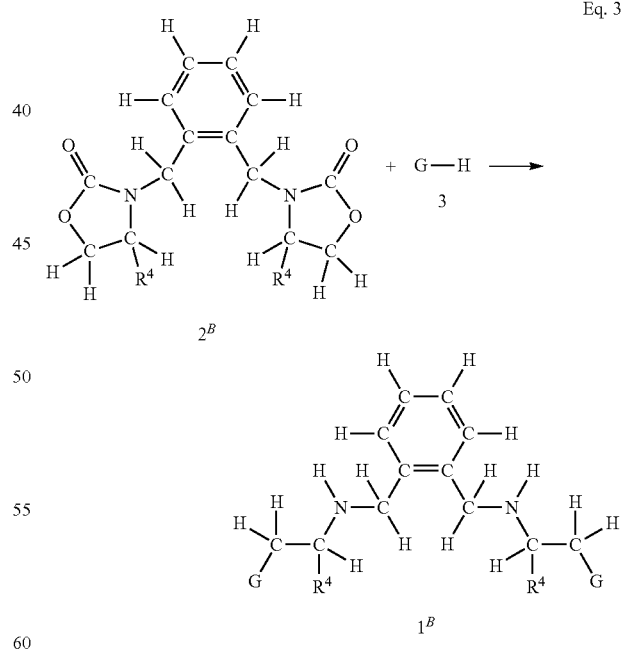

The thus-obtained compound ($1^A$) of the present invention may be subjected, if desired, to a post treatment, isolation and purification. The method for the post treatment includes, for example, concentration, solvent replacement, washing, extraction, filtration, and formation of a salt by the addition of a Bronsted acid, and these methods can be performed independently or in combination. The method for isolation and purification includes, for example, decolorization with an adsorbent, column chromatography, distillation, and crystallization, and these methods can be performed independently or in combination.

[Transition Metal Complex of the Present Invention]

The transition metal complex of the present invention is described in detail below. The metal species in the transition metal complex of the present invention is not particularly limited as long as the compound ($1^4$) of the present invention can be coordinated thereto, but in view of catalytic activity in an organic synthesis reaction, the metal species is preferably a metal species selected from the group consisting of transition metals of groups 8 to 11, more preferably a metal species selected from transition metals of group 8, and particularly preferable metal species include iron and ruthenium.

The transition metal complex of the present invention is obtained by subjecting the compound ($1^4$) of the present invention to a reaction with a transition metal compound serving as a transition metal source. The transition metal compound is also not particularly limited as long as the compound ($1^4$) of the present invention can react therewith, but compounds of transition metals of groups 8 to 11, i.e., an iron compound, a ruthenium compound, an osmium compound, a cobalt compound, a rhodium compound, an iridium compound, a nickel compound, a palladium compound, a platinum compound, a copper compound, a silver compound, and a gold compound are preferred; compounds of transition metals of group 8, i.e., an iron compound, a ruthenium compound, and an osmium compound are more preferred; and an iron compound and a ruthenium compound are still more preferred as the transition metal compound. The preferable transition metal compounds are described more specifically below.

Examples of the iron compound include zerovalent, divalent and trivalent iron compounds and specifically include iron(0) pentacarbonyl, diiron(0) nonacarbonyl, triiron(0) dodecacarbonyl, iron(II) fluoride, iron(II) chloride, iron(II) chloride tetrahydrate, iron(II) bromide, iron(II) iodide, iron (II) sulfate monohydrate, iron(II) sulfate heptahydrate, iron (II) perchlorate hexahydrate, iron(II) trifluoromethanesulfonate, iron(II) tetrafluoroborate hexahydrate, iron(II) acetate, ammonium iron(II) sulfate hexahydrate, iron(II) acetylacetonate, iron(III) fluoride, iron(III) fluoride trihydrate, iron(III) chloride, iron(III) chloride hexahydrate, iron (III) bromide, iron(III) sulfate hydrate, iron(III) nitrate nonahydrate, iron(III) perchlorate hydrate, iron(III) trifluoromethanesulfonate, iron(III) phosphate hydrate, iron (III) acetylacetonate, and iron(III) trifluoroacetylacetonate, and preferable specific examples thereof include iron(II) chloride.

Examples of the ruthenium compound include zerovalent, divalent and trivalent ruthenium compounds and specifically include triruthenium(0) dodecacarbonyl, dichloro(benzene) ruthenium(II) dimer, dichloro(p-cymene)ruthenium(II) dimer, dichloro(mesitylene)ruthenium(II) dimer, dichloro (hexamethylbenzene)ruthenium(II) dimer, diiodo(p-cymene)ruthenium(II) dimer, dipivalato(p-cymene)ruthenium (II), bis(π-methallyl)(1,5-cyclooctadiene)ruthenium(II), dichloro(1,5-cyclooctadiene)ruthenium(II) polymer, dichloro(norbornadiene)ruthenium(II) polymer, dichlorotris(triphenylphosphine)ruthenium(II), chlorohydridotris(triphenylphosphine)ruthenium(II) toluene adduct, dihydridotetrakis (triphenylphosphine)ruthenium(II), carbonylchlorohydridotris(triphenylphosphine)ruthenium(II), carbonyldihydridotris(triphenylphosphine)ruthenium(II), dichlorotetrakis(dimethylsulfoxide)ruthenium(II), ruthenium(III) chloride, ruthenium(III) chloride hydrate, ruthenium(III) iodide, ruthenium(III) iodide hydrate, hexaammineruthenium(III) trichloride, and ruthenium(III) acetylacetonate, and preferable specific examples thereof include dichloro(p-cymene) ruthenium(II) dimer, dichlorotris(triphenylphosphine)ruthenium(II), and dipivalato(p-cymene)ruthenium(II).

Examples of the osmium compound includes divalent and trivalent osmium compounds and specifically include dichloro(p-cymene)osmium(II) dimer, carbonylchlorohydridotris(triphenylarsine)osmium(II), osmium(III) chloride, and osmium(III) chloride trihydrate.

Examples of the cobalt compound include divalent and trivalent cobalt compounds and specifically include cobalt (II) fluoride, cobalt(II) fluoride tetrahydrate, cobalt(II) chloride, cobalt(II) chloride dihydrate, cobalt(II) chloride hexahydrate, cobalt(II) bromide, cobalt(II) bromide dihydrate, cobalt(II) iodide, cobalt(II) sulfate monohydrate, cobalt(II) sulfate heptahydrate, cobalt(II) nitrate hexahydrate, cobalt (II) perchlorate hexahydrate, cobalt(II) tetrafluoroborate hexahydrate, cobalt(II) acetate, cobalt(II) acetate tetrahydrate, cobalt(II) cyanide dihydrate, cobalt(II) acetylacetonate, cobalt(II) acetylacetonate hydrate, cobalt(II) hexafluoroacetylacetonate hydrate, cobalt(III) fluoride, cobalt(III) acetylacetonate, and hexaamminecobalt(III) trichloride.

Examples of the rhodium compound include monovalent, divalent and trivalent rhodium compounds and specifically include chloro(1,5-hexadiene)rhodium(I) dimer, chloro(1,5-cyclooctadiene)rhodium(I) dimer, chlorobis(cyclooctene)rhodium(I) dimer, bis(1,5-cyclooctadiene)rhodium(I) trifluoromethanesulfonate, bis(1,5-cyclooctadiene)rhodium(I) hexafluoroantimonate, bis(1,5-cyclooctadiene)rhodium(I) tetrafluoroborate, bis(norbornadiene)rhodium(I) trifluoromethanesulfonate, (acetylacetonato)bis(ethylene)rhodium (I), (acetylacetonato)(1,5-cyclooctadiene)rhodium(I), (acetylacetonato)(norbornadiene)rhodium(I), bis(acetonitrile)(1,5-cyclooctadiene)rhodium(I) tetrafluoroborate, bis (1,5-cyclooctadiene)rhodium(I) tetrakis[bis(3,5-trifluoromethyl)phenyl]borate, tetrakis(triphenylphosphine)rhodium (I) hydride, (acetylacetonato)dicarbonylrhodium(I), rhodium(III) chloride, rhodium(III) chloride trihydrate, rhodium(III) nitrate hydrate, tetrakis(μ-trifluoroacetato)dirhodium(II), tetrakis(μ-acetato)dirhodium(II), tetrakis(μ-acetato)dirhodium(II) dihydrate, tetrakis(μ-trimethylacetato) dirhodium(II), tetrakis(μ-octanoato)dirhodium(II), tetrakis (triphenylacetato)dirhodium(II), and rhodium(II) acetylacetonate.

Examples of the iridium compound include monovalent and trivalent iridium compounds and specifically include chloro(1,5-cyclooctadiene)iridium(I) dimer, (1,5-cyclooctadienexmethoxy)iridium(I) dimer, bis(cyclooctadiene)iridium(I) tetrakis[3,5-bis(trifluoromethyl)phenyl]borate, bis(1, 5-cyclooctadiene)iridium(I) tetrafluoroborate, (1,5-cyclooctadieneXhexafluoroacetylacetonato)iridium(I), (acetylacetonato)(1,5-cyclooctadiene)iridium(I), (acetylacetonato)dicarbonyliridium(I), iridium(III) chloride, iridium (III) chloride hydrate, and iridium(III) acetylacetonate.

Examples of the nickel compound include zerovalent and divalent nickel compounds and specifically include bis(1,5-cyclooctadiene)nickel(0), tetrakis(triphenylphosphine) nickel(0), dichlorobis(triphenylphosphine)nickel(II), nickel (II) fluoride, nickel(II) chloride, nickel(II) chloride monohydrate, nickel(II) chloride hexahydrate, nickel(II) bromide, nickel(II) bromide trihydrate, nickel(II) iodide, nickel(II) trifluoromethanesulfonate, nickel(II) sulfate, nickel(II) sulfate hexahydrate, nickel(II) sulfate heptahydrate, nickel(II) nitrate hexahydrate, nickel(II) perchlorate hexahydrate, nickel(II) oxalate dihydrate, nickel(II) acetate tetrahydrate, nickel(II) acetylacetonate, and nickel(II) hexafluoroacetylacetonate hydrate.

Examples of the palladium compound include zerovalent and divalent palladium compounds and specifically include bis(dibenzylideneacetone)palladium(0), tris(dibenzylideneacetone)dipalladium(0), tetrakis(triphenylphosphine)palladium(0), bis(acetonitrile)dichloropalladium(II), bis(acetonitrile)dibromopalladium(II), bis(benzonitrile)dichloropalladium(II), bis(benzonitrile)dibromopalladium(II), dichloro(1,5-cyclooctadiene)palladium(II), bis(triphenylphosphine)dichloropalladium(II), (π-allyl)palladium(II) chloride dimer, (π-methallyl)palladium(II) chloride dimer, (π-cinnamyl)palladium(II) chloride dimer, palladium(II) chloride, palladium(II) bromide, palladium(II) iodide, palladium(II) sulfate, palladium(II) nitrate dihydrate, palladium(II) trifluoroacetate, palladium(II) acetate, palladium(II) propionate, palladium(II) pivalate, palladium(II) cyanide, palladium(II) acetylacetonate, palladium(II) hexafluoroacetylacetonate, tetrakis(acetonitrile)palladium(II) tetrafluoroborate, sodium tetrachloropalladate(II), and potassium tetrachloropalladate(II).

Examples of the platinum compound include divalent and tetravalent platinum compounds and specifically include platinum(II) chloride, platinum(II) bromide, platinum(II) iodide, platinum(II) cyanide, platinum(II) acetylacetonate, potassium tetrachloroplatinate(II), dichloro(1,5-cyclooctadiene)platinum(II), cis-bis(acetonitrile)dichloroplatinum(II), trans-bis(acetonitrile)dichloroplatinum(II), cis-bis(benzonitrile)dichloroplatinum(II), platinum(IV) chloride, and potassium hexachloroplatinate(IV).

Examples of the copper compound include monovalent and divalent copper compounds and specifically include copper(I) oxide, copper(I) chloride, copper(I) bromide, copper(I) iodide, copper(I) trifluoromethanesulfonate benzene complex, copper(I) acetate, copper(I) cyanide, tetrakis(acetonitrile)copper(I) tetrafluoroborate, tetrakis(acetonitrile)copper(I) hexafluorophosphate, copper(II) oxide, copper(II) fluoride, copper(II) fluoride dihydrate, copper(II) chloride, copper(II) chloride dihydrate, copper(II) bromide, copper(II) trifluoromethanesulfonate, copper(II) sulfate, copper(II) sulfate pentahydrate, copper(II) nitrate trihydrate, copper(II) perchlorate hexahydrate, copper(II) tetrafluoroborate hexahydrate, copper(II) trifluoroacetate, copper(II) acetate, copper(II) acetate monohydrate, copper(II) acetylacetonate, and copper(II) hexafluoroacetylacetonate hydrate.

Examples of the silver compound include monovalent and divalent silver compounds and specifically include silver(I) oxide, silver(I) fluoride, silver(I) chloride, silver(I) bromide, silver(I) trifluoromethanesulfonate, silver(I) methanesulfonate, silver(I) p-toluenesulfonate, silver(I) sulfate, silver(I) nitrate, silver(I) perchlorate, silver(I) perchlorate monohydrate, silver(I) tetrafluoroborate, silver(I) hexafluorophosphate, silver(I) trifluoroacetate, silver(I) acetate, silver(I) benzoate, silver(I) carbonate, silver(I) nitrite, silver(I) cyanate, silver(I) acetylacetonate, silver(II) fluoride, and silver(II) picolinate.

Examples of the gold compound include monovalent and trivalent gold compounds and specifically include gold(I) chloride, gold(I) iodide, gold(I) cyanide, gold(III) chloride, gold(III) chloride dihydrate, gold(III) bromide, chloroauric acid(III) tetrahydrate, and potassium chloroaurate(III).

In the production of the transition metal complex of the present invention, a solvent is preferably allowed to coexist. The solvent is not particularly limited as long as it does not inhibit the coordination action of the compound ($1^A$) of the present invention, but preferable specific examples thereof include toluene, tetrahydrofuran, 1-butanol, 3-methoxy-1-butanol, and acetone. Each of these solvents may be used alone, or two or more thereof may be appropriately used in combination. In the reaction of the compound ($1^A$) of the present invention with a transition metal compound, an acid and a base may be allowed to coexist, if desired, and the production may be performed in an inert gas atmosphere such as nitrogen and argon.

The thus-obtained transition metal complex of the present invention may be subjected, if desired, to a post treatment, isolation and purification. Examples of the method for the post treatment include concentration, solvent replacement, washing, extraction, and filtration, and these post treatments can be performed independently or in combination.

Examples of the method for isolation and purification include decolorization with an adsorbent, column chromatography, crystallization, and sublimation, and these methods can be performed independently or in combination.

In the case of using the transition metal complex of the present invention as a catalyst in an organic synthesis reaction, the transition metal complex of the present invention may be used without isolating it from the reaction solution of the compound ($1^A$) of the present invention and a transition metal compound or may be used after performing, if desired, the above-described post treatment, isolation and purification, and each may be used alone or two or more may be appropriately used in combination. Furthermore, an organic synthesis reaction using the complex as a catalyst may be performed while preparing the transition metal complex of the present invention by directly adding the compound ($1^A$) of the present invention and a transition metal compound to the inside of the organic synthesis reaction system. In addition, the transition metal complex of the present invention may be subjected to various chemical conversions including an anion exchange reaction and then used as a catalyst in an organic synthesis reaction.

The compound ($1^A$) of the present invention acts mainly as a tetradentate ligand but may act as a bidentate ligand or a tridentate ligand depending on the structure of the transition metal compound reacted and may also act as a cross-linking ligand between the same or different metals. Accordingly, the transition metal complex of the present invention may be not only a mononuclear complex (a complex having only one metal atom) but also a polynuclear complex (a complex having two or more metal atoms, irrespective of the same or different), but in view of catalytic activity in an organic synthesis reaction, it is more preferred to be a mononuclear complex.

The particularly preferred embodiment of the transition metal complex of the present invention specifically includes transition metal complexes shown below, i.e., $RuCl_2(1^B\text{-}1)$ to $FeCl_2[(S,S)\text{-}1^B\text{-}3]$. The coordination form of these transition metal complexes may be any of trans, cis-α, and cis-β.

[Chem. 23]
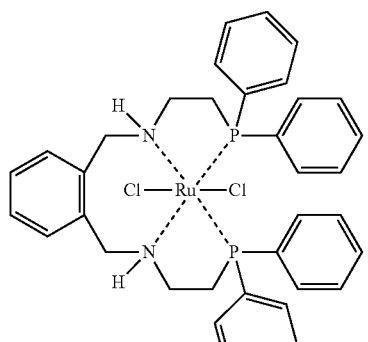
RuCl$_2$(1$^B$-1)
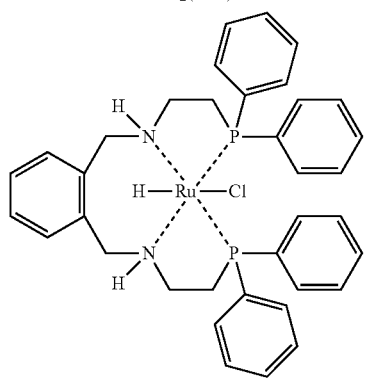
RuHCl(1$^B$-1)
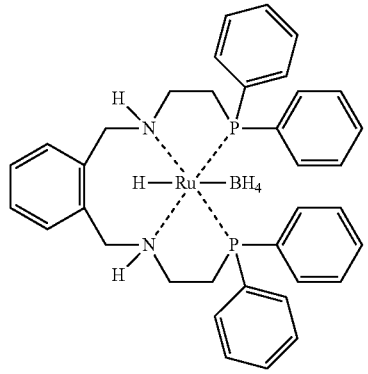
RuH(BH$_4$)(1$^B$-1)
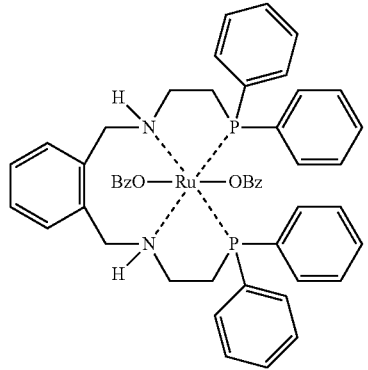
Ru(OBz)$_2$(1$^B$-1)
-continued
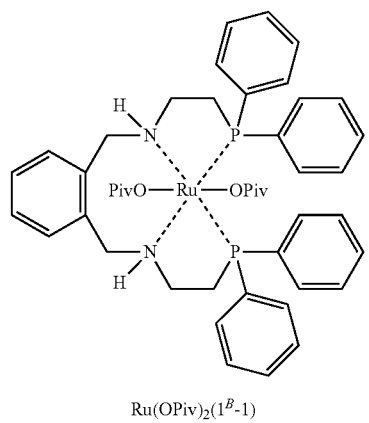
Ru(OPiv)$_2$(1$^B$-1)
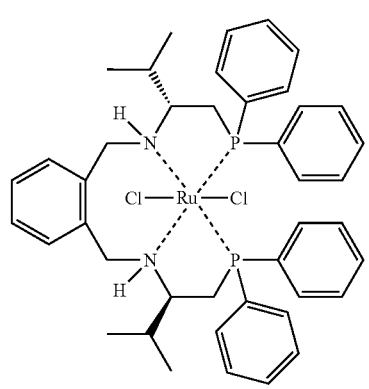
RuCl$_2$[(R,R)-1$^B$-2]
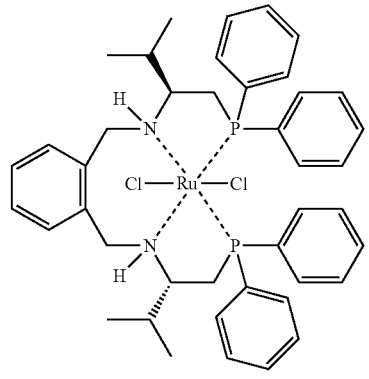
RuCl$_2$[(S,S)-1$^B$-2]
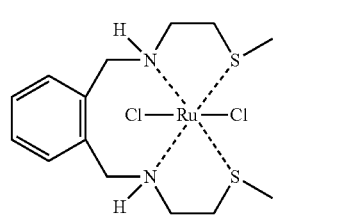
RuCl$_2$(1$^B$-6)

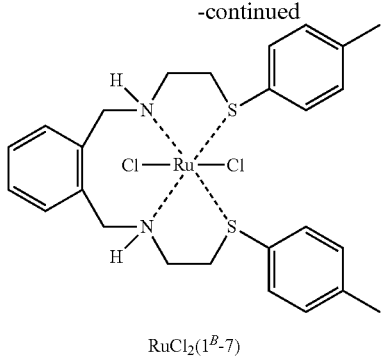

RuCl₂(1^B-7)

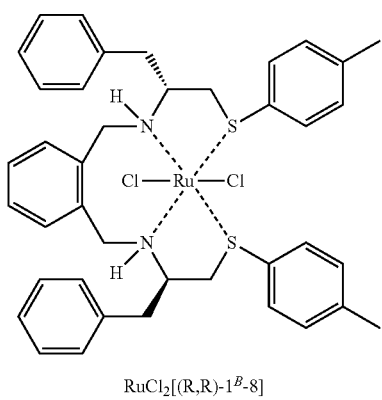

RuCl₂[(R,R)-1^B-8]

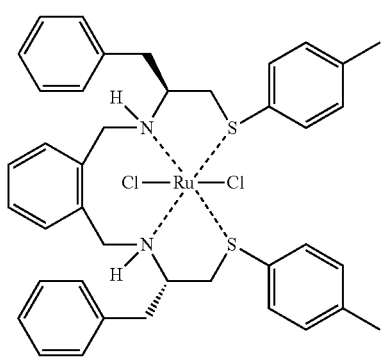

RuCl₂[(S,S)-1^B-8]

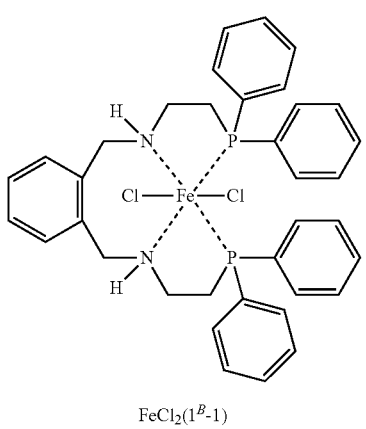

FeCl₂(1^B-1)

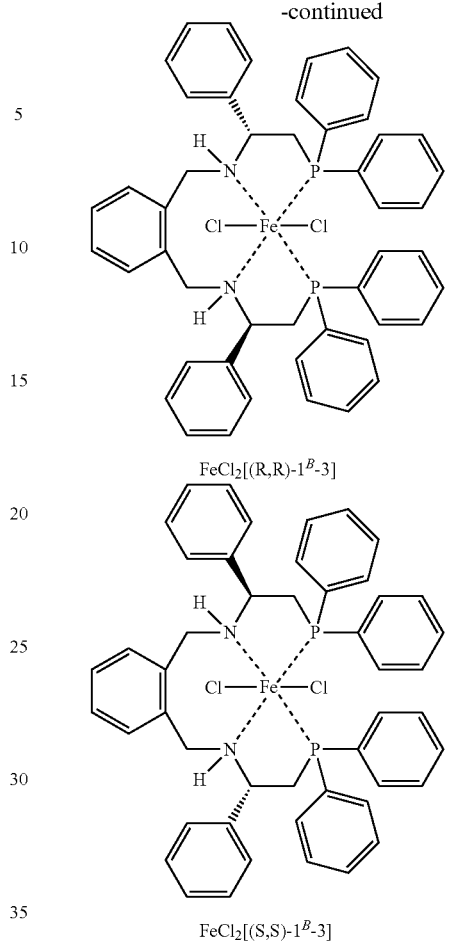

FeCl₂[(R,R)-1^B-3]

FeCl₂[(S,S)-1^B-3]

The compound (1^A) of the present invention is useful as a ligand in a variety of catalytic organic synthesis reactions, and the transition metal complex of the present invention is useful as a catalyst in a variety of organic synthesis reactions. The organic synthesis reaction is not particularly limited but specifically includes an oxidation reaction, a reduction reaction, a hydrogenation reaction, a dehydrogenation reaction, a hydrogen transfer reaction, an addition reaction, a conjugate addition reaction, a pericyclic reaction, a functional group conversion reaction, an isomerization reaction, a rearrangement reaction, a polymerization reaction, a bond formation reaction, and a bond cleavage reaction, and preferably includes a hydrogenation reaction, and preferable specific examples thereof include a hydrogenation reaction of esters, amides, lactones, and nitriles.

EXAMPLES

The compound of the present invention, the metal complex of the present invention, the intermediate of the present invention, and the catalytic reaction using the metal complex of the present invention are described in detail below by referring to Examples, but the present invention is not limited by these Examples in any way. In Examples, the following apparatuses and conditions were employed for the measurements of physical properties.

1) Proton nuclear magnetic resonance spectroscopy ($^1$H NMR): Model 400MR DD2 apparatus (resonance frequency: 400 MHz, manufactured by Agilent Technology Inc.)

2) Carbon 13 nuclear magnetic resonance spectroscopy ($^{13}$C NMR): Model 400MR DD2 apparatus (resonance frequency: 100 MHz, manufactured by Agilent Technology Inc.)

3) Phosphorus 31 nuclear magnetic resonance spectroscopy ($^{31}$P NMR): Model 400MR DD2 apparatus (resonance frequency: 161 MHz, manufactured by Agilent Technology Inc.)

4) High-resolution mass spectrometry (HRMS): Model JMS-T100GCV apparatus (manufactured by JEOL Ltd.)

5) Gas chromatography (GC): Model GC-4000 apparatus (manufactured by GL Sciences Inc.) and Model GC-4000Plus apparatus (manufactured by GL Sciences Inc.)

[Measurement Condition 1] Apparatus: Model GC-4000 apparatus, column: InertCap 1 (manufactured by GL Sciences Inc.), injector temperature: 250° C., detector temperature: 250° C., initial temperature: 50° C., temperature rate: 10° C./min, final temperature: 250° C., holding time at final temperature: 0 minute.

[Measurement Condition 2] In GC measurement condition 1, Model GC-4000Plus apparatus was used as the apparatus, and the holding time at final temperature was extended to 10 minutes from 0 minute.

Examples 1 to 4 are related to the production of the intermediate ($2^A$) of the present invention, Examples 5 to 12 are related to the production of the compound ($1^A$) of the present invention, Examples 13 to 24 are related to the production of the transition metal complex of the present invention, and Examples 25 to 39 are related to the organic synthesis reaction using the transition metal complex of the present invention as a catalyst. Unless otherwise indicated, the substrate and solvent were charged under nitrogen stream, the reaction was carried out under a nitrogen atmosphere, and the post treatment of the reaction solution and the isolation and purification of the crude product were carried out in air.

Example 1

Synthesis of 3,3'-[1,2-phenylenebis(methylene)]bis (2-oxazolidinone) (Structural Formula ($2^B$-1)) (Eq. 4)

[Chem. 24]

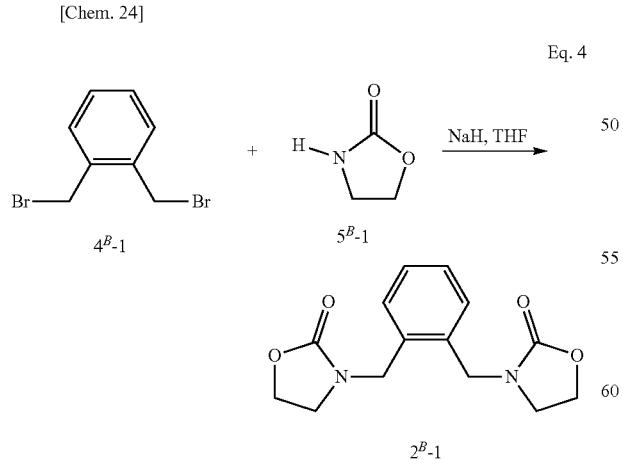

(Setup/Reaction)

A 500 mL four-necked round-bottom flask equipped with a magnetic stirring bar, 200 mL dropping funnel, condenser, thermometer and a three-way stopcock was evacuated and filled with nitrogen gas, α,α'-dibromo-o-xylene ($4^B$-1) (20.0 g, 75.8 mmol, 1.0 equivalent), dehydrated tetrahydrofuran (THF) (76 mL) and sodium hydride (NaH) (purity: 62.5%, 6.4 g, 166.8 mmol, 2.2 equivalents) were charged into the flask successively. The obtained gray suspension was heated by means of an oil bath while stirring with a magnetic stirrer and thereby refluxed (inner temperature: about 66° C.). Subsequently, 2-oxazolidone ($5^B$-1) (13.9 g, 159.2 mmol, 2.1 equivalents) and dehydrated THF (140 mL) were charged into the dropping funnel successively, dissolved by heating with a heat gun, and then added dropwise into the reaction mixture over 60 minutes under reflux (vigorous foaming occurred upon dropwise addition). The obtained white suspension was then stirred for 1 hour under reflux.

(Post Treatment/Isolation/Purification)

After the reaction solution was concentrated under reduced pressure, water (100 mL) and chloroform (200 mL) were charged thereinto successively, followed by stirring at room temperature, and after standing still, the aqueous layer was separated. The aqueous layer was extracted with chloroform (50 mL) and thereafter, the organic layers were combined and washed once with water (50 mL). The organic layer was concentrated under reduced pressure and after adding ethyl acetate (100 mL) to the obtained residue, the solution was cooled to 5° C. by means of ice-water bath while stirring to precipitate crystals. The crystals were collected by suction filtration, washed with cold ethyl acetate (−20° C., 100 mL), and then dried by heating under reduced pressure to give 19.7 g of title compound ($2^B$-1) as a white powder. Isolated yield: 94.1%.

$^1$H NMR (400 MHz, CDCl$_3$): δ=7.36-7.28 (m, 4H), 4.52 (s, 4H), 4.37-4.31 (m, 4H), 3.49-3.43 (m, 4H).

$^{13}$C NMR (100 MHz, CDCl$_3$): δ=158.35, 134.15, 129.26, 128.49, 61.83, 45.47, 44.20.

Example 2

Synthesis of 3,3'-[1,2-phenylenebis(methylene)]bis [(S)-4-isopropyl-2-oxazolidinone] (Structural Formula ((S,S)-$2^B$-2)) (Eq. 5)

[Chem. 25]

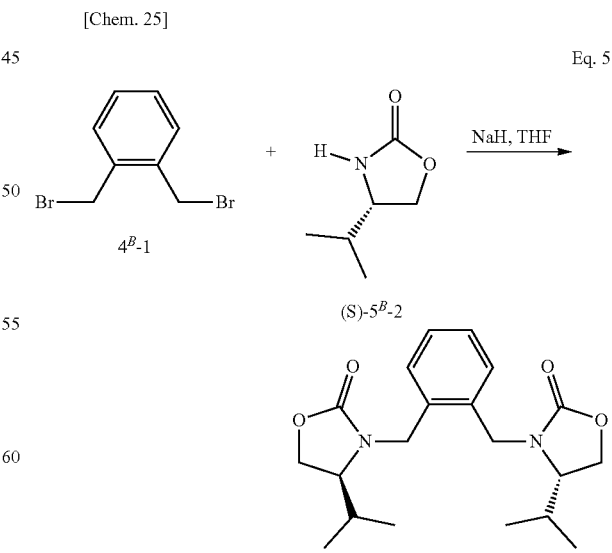

37

(Setup/Reaction)

A 200 mL four-necked round-bottom flask equipped with a magnetic stirring bar, 100 mL dropping funnel, condenser, thermometer and a three-way stopcock was evacuated and filled with nitrogen gas, α,α'-dibromo-o-xylene ($4^B$-1) (7.92 g, 30.0 mmol, 1.0 equivalent), dehydrated THF (30 mL) and NaH (purity: 62.5%, 2.53 g, 66.0 mmol, 2.2 equivalents) were charged into the flask successively. The obtained gray suspension was heated by means of an oil bath while stirring with a magnetic stirrer and thereby refluxed. Subsequently, (S)-4-isopropyl-2-oxazolidinone ((S)-$5^B$-2) (7.94 g, 61.5 mmol, 2.05 equivalents) and dehydrated THF (60 mL) were charged into the dropping funnel successively, and the obtained solution was added dropwise into the reaction mixture over 30 minutes under reflux. The obtained white suspension was then stirred for 1 hour under reflux.

(Post Treatment/Isolation/Purification)

After the reaction solution was concentrated under reduced pressure, water (50 mL) and ethyl acetate (100 mL) were charged thereinto successively, followed by stirring at room temperature, and after standing still, the aqueous layer was separated. The organic layer was washed once with water (25 mL) and then concentrated under reduced pressure, and after the obtained residue was dissolved in chloroform (20 mL), n-hexane (100 mL) was gradually added to precipitate crystals. The crystals were collected by suction filtration, washed with n-hexane (50 mL), and then dried by heating under reduced pressure to give 8.90 g of title compound ((S,S)-$2^B$-2) as a white powder. Isolated yield: 82.3%.

$^1$H NMR (400 MHz, CDCl$_3$): δ=7.33-7.27 (m, 4H), 4.77 (d, J=16.0 Hz, 2H), 4.28 (d, J=16.0 Hz, 2H), 4.22 (t, J=9.2 Hz, 2H), 4.13 (dd, J=5.2, 9.2 Hz, 2H), 3.62 (ddd, J=3.6, 5.2, 8.8 Hz, 2H), 2.09-1.95 (m, 2H), 0.85 (d, J=6.8 Hz, 6H), 0.83 (d, J=6.8 Hz, 6H).

$^{13}$C NMR (100 MHz, CDCl$_3$): δ=158.64, 134.08, 128.72, 128.14, 62.85, 59.27, 43.24, 27.47, 17.74, 14.08.

Example 3

Synthesis of 3,3'-[1,2-phenylenebis(methylene)]bis [(S)-4-phenyl-2-oxazolidinone] (Structural Formula ((S,S)-$2^B$-3)) (Eq. 6)

[Chem. 26]

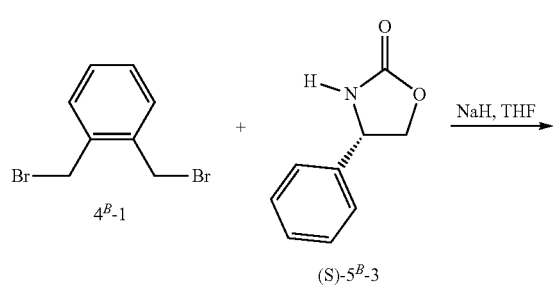

Eq. 6

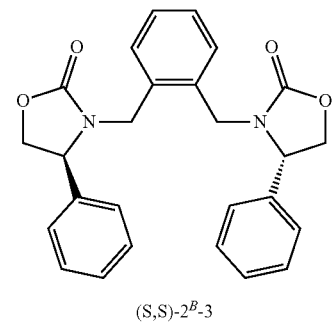

(S,S)-$2^B$-3

(Setup/Reaction)

A 200 mL four-necked round-bottom flask equipped with a magnetic stirring bar, 100 mL dropping funnel, condenser, thermometer and a three-way stopcock was evacuated and filled with nitrogen gas, α,α'-dibromo-o-xylene ($4^B$-1) (7.92 g, 30.0 mmol, 1.0 equivalent), dehydrated THF (30 mL) and NaH (purity: 62.5%, 2.53 g, 66.0 mmol, 2.2 equivalents) were charged into the flask successively. The obtained gray suspension was heated by means of an oil bath while stirring with a magnetic stirrer and thereby refluxed. Subsequently, (S)-4-phenyl-2-oxazolidinone ((S)-$5^B$-3) (10.0 g, 61.5 mmol, 2.05 equivalents) and dehydrated THF (60 mL) were charged into the dropping funnel successively, dissolved by heating with a heat gun, and then added dropwise into the reaction mixture over 30 minutes under reflux. The obtained white suspension was then stirred for 1 hour under reflux.

(Post Treatment/Isolation/Purification)

After the reaction solution was concentrated under reduced pressure, water (50 mL) and chloroform (200 mL) were charged thereinto successively, followed by stirring at room temperature, and after standing still, the aqueous layer was separated. The organic layer was washed once with water (50 mL) and then concentrated under reduced pressure, and after adding chloroform (40 mL) to the residue and performing heating, n-hexane (240 mL) was gradually added to the obtained solution to precipitate swollen crystals. The crystals were collected by suction filtration, washed with n-hexane (100 mL), and then dried by heating under reduced pressure to give 12.2 g of title compound ((S,S)-$2^B$-3) as a white powder. Isolated yield: 94.9%.

$^1$H NMR (400 MHz, CDCl$_3$): δ=7.36-7.29 (m, 6H), 7.25-7.19 (m, 2H), 7.13-7.02 (m, 6H), 4.51-4.41 (m, 6H), 4.02 (dd, J=5.6, 7.2 Hz, 2H), 3.53 (d, J=15.6 Hz, 2H).

$^{13}$C NMR (100 MHz, CDCl$_3$): δ=158.20, 137.17, 133.88, 129.56, 129.28, 129.07, 128.27, 126.94, 69.90, 59.24, 42.37.

Example 4

Synthesis of 3,3'-[1,2-phenylenebis(methylene)]bis[(S)-4-benzyl-2-oxazolidinone] (Structural Formula ((S,S)-$2^B$-4)) (Eq. 7)

[Chem. 27]

Eq. 7

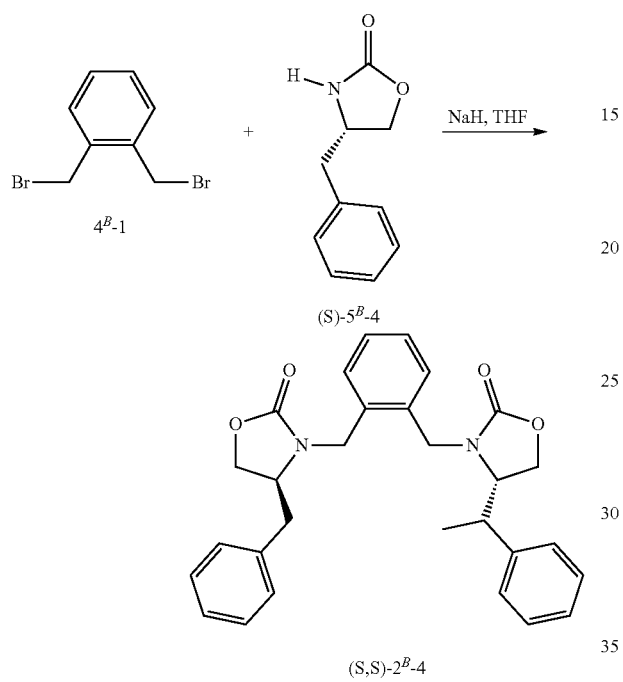

(Setup/Reaction)

A 500 mL four-necked round-bottom flask equipped with a magnetic stirring bar, 200 mL dropping funnel, condenser, thermometer and a three-way stopcock was evacuated and filled with nitrogen gas, α,α'-dibromo-o-xylene ($4^B$-1) (10.2 g, 38.5 mmol, 1.0 equivalent), dehydrated THF (40 mL) and NaH (purity: 58.8%, 3.46 g, 84.7 mmol, 2.2 equivalents) were charged into the flask successively. The obtained gray suspension was heated by means of an oil bath while stirring with a magnetic stirrer and thereby refluxed. Subsequently, (S)-4-benzyl-2-oxazolidinone ((S)-$5^B$-4) (14.0 g, 79.0 mmol, 2.05 equivalents) and dehydrated THF (80 mL) were charged into the dropping funnel successively, dissolved by heating with a heat gun, and then added dropwise into the reaction mixture over 30 minutes under reflux. The obtained white suspension was then stirred for 1 hour under reflux.

(Post Treatment/Isolation/Purification)

After the reaction solution was concentrated under reduced pressure, water (200 mL) and chloroform (200 mL) were charged thereinto successively, followed by stirring at room temperature, and after standing still, the aqueous layer was separated. The cloudy organic layer was washed twice with water (50 mL) and then concentrated under reduced pressure, and after dissolving the obtained residue by adding chloroform (40 mL), n-hexane (80 mL) was gradually added to precipitate crystals. The crystals were collected by suction filtration, washed with n-hexane (100 mL), and then dried by heating under reduced pressure to give 16.2 g of title compound ((S,S)-$2^B$-4) as a white powder. Isolated yield: 91.9%.

$^1$H NMR (400 MHz, CDCl$_3$): δ=7.41-7.20 (m, 10H), 7.05-7.00 (m, 4H), 4.65 (d, J=16.0 Hz, 2H), 4.40 (d, J=16.0 Hz, 2H), 4.18 (t, J=8.8 Hz, 2H), 4.05 (dd, J=5.6, 8.8 Hz, 2H), 3.94-3.86 (m, 2H), 3.02 (dd, J=4.8, 13.6 Hz, 2H), 2.61 (dd, J=9.2, 13.6 Hz, 2H).

$^{13}$C NMR (100 MHz, CDCl$_3$): δ=158.22, 135.22, 134.34, 128.92, 128.90, 128.30, 127.18, 66.99, 56.45, 43.97, 38.61.

Example 5

Synthesis of N,N'-[1,2-phenylenebis(methylene)]bis[2-(diphenylphosphino)ethylamine] (Structural Formula ($1^B$-1)) (Eq. 8)

[Chem. 28]

Eq. 8

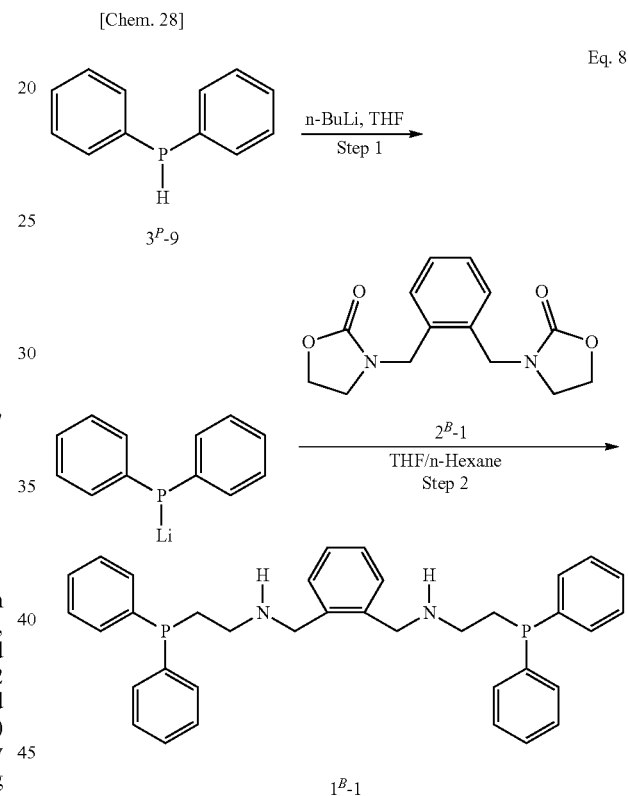

First Step (Setup/Reaction)

A 500 mL four-necked round-bottom flask equipped with a magnetic stirring bar, 50 mL dropping funnel, thermometer and a three-way stopcock was evacuated and filled with nitrogen gas, diphenylphosphine ($3^P$-9) (purity: 98.5%, 10.0 g, net weight: 9.85 g, 52.9 mmol, 2.2 equivalents) and dehydrated THF (53 mL) were charged into the flask successively. The obtained solution was cooled to 5° C. by means of an ice-water bath while stirring with a magnetic stirrer. Subsequently, an n-hexane solution of n-butyllithium (n-BuLi) (concentration: 1.61 mol/L, 32.9 mL, 52.9 mmol, 2.2 equivalents) was charged into the dropping funnel and added dropwise into the reaction solution over 20 minutes at a rate keeping the inner temperature at 10° C. or less. Thereafter, the ice-water bath was removed, and the obtained solution was stirred for 20 minutes at room temperature to give a THF/n-hexane solution of lithium diphenylphosphide (52.9 mmol, 2.2 equivalents) as a red-orange liquid.

Second Step (Setup/Reaction)

A 500 mL four-necked round-bottom flask equipped with a magnetic stirring bar, 200 mL dropping funnel, thermometer and a three-way stopcock was evacuated and filled with nitrogen gas, 3,3'-[1,2-phenylenebis(methylene)]bis(2-oxazolidinone) ($2^B$-1) (6.64 g, 24.0 mmol, 1.0 equivalent) obtained in Example 1 and dehydrated THF (72 mL) were charged into the flask successively, and the obtained white suspension was stirred with a magnetic stirrer. Subsequently, the THF/n-hexane solution of lithium diphenylphosphide (52.9 mmol, 2.2 equivalents) obtained in the first step was charged into the dropping funnel, and added dropwise into the suspension over 30 minutes at a rate keeping the inner temperature at 30° C. or less. Thereafter, the obtained red-orange reaction solution was stirred at room temperature for 1 hour.

(Post Treatment/Isolation/Purification)

After the reaction solution was concentrated under reduced pressure, toluene (250 mL) and water (250 mL) were charged thereinto successively, followed by stirring at room temperature, and after standing still, the aqueous layer was separated. The organic layer was washed twice with water (50 mL) and then concentrated under reduced pressure to afford the residue, which was purified by silica gel column chromatography (after removing impurities by using toluene/ethyl acetate=1/1 as an eluent, the eluent was switched to ethyl acetate/triethylamine=20/1 to elute the target substance) to give 11.3 g of title compound ($1^B$-1) as a pale yellow viscous liquid. Isolated yield: 84.0%. This compound had difficulty in weighing because of its high viscosity, and therefore it was stored as a toluene solution under nitrogen.

$^1$H NMR (400 MHz, CDCl$_3$): δ=7.42-7.34 (m, 8H), 7.32-7.26 (m, 12H), 7.23-7.16 (m, 4H), 3.75 (s, 4H), 2.82-2.72 (m, 4H), 2.27 (t, J=8.0 Hz, 4H), 1.77* (br s, 2H) (*including a peak derived from water).

$^{31}$P NMR (161 MHz, CDCl$_3$): δ=−20.83 (s, 2P).

Example 6

Synthesis of (1S,1'S)-N,N'-[1,2-phenylenebis(methylene)]bis[2-(diphenylphosphino)-1-isopropyl-ethylamine] (Structural Formula ((S,S)-$1^B$-2)) (Eq. 9)

[Chem. 29]

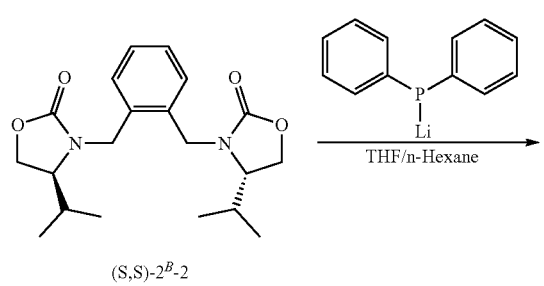

Eq. 9

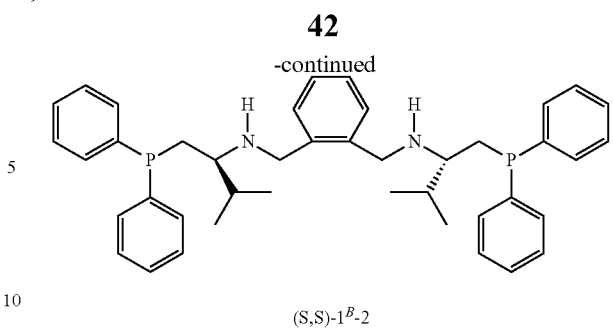

(S,S)-$1^B$-2

(Setup/Reaction)

A THF/n-hexane solution of lithium diphenylphosphide (52.9 mmol, 2.2 equivalents) was prepared by performing the same operation as in the first step of Example 5. Subsequently, the 50 mL dropping funnel charged with n-BuLi was removed, and a 100 mL dropping funnel was attached instead. Into this dropping funnel were charged 3,3'-[1,2-phenylenebis(methylene)]bis[(S)-4-isopropyl-2-oxazolidinone] ((S,S)-$2^B$-2) (8.7 g, 24.0 mmol, 1.0 equivalent) obtained in Example 2 and dehydrated THF (72 mL) successively, dissolved by heating with a heat gun, and then added dropwise into the solution over 30 minutes at a rate keeping the inner temperature at 30° C. or less. The obtained red-orange reaction solution was stirred with the magnetic stirrer at room temperature for 1 hour.

(Post Treatment/Isolation/Purification)

After the reaction solution was concentrated under reduced pressure, toluene (250 mL) and water (250 mL) were charged thereinto successively, followed by stirring, and after standing still, the aqueous layer was separated. The organic layer was washed twice with water (50 mL) and then concentrated under reduced pressure to afford the residue, which was purified by silica gel column chromatography (after removing impurities by using toluene as an eluent, the eluent was switched to toluene/ethyl acetate/triethylamine=100/10/1 to elute the target substance) to give 13.8 g of title compound ((S,S)-$1^B$-2) as a pale brown viscous liquid. Isolated yield: 89.2%. This compound had difficulty in weighing because of its high viscosity, and therefore it was stored as a toluene solution under nitrogen.

$^1$H NMR (400 MHz, CDCl$_3$): δ=7.44-7.25 (m, 20H), 7.18-7.12 (m, 4H), 3.78 (d, J=12.4 Hz, 2H), 3.68 (d, J=12.4 Hz, 2H), 2.50-2.41 (m, 2H), 2.25-2.16 (m, 2H), 2.10-1.96 (m, 4H), 1.55* (br s, 2H), 0.87 (d, J=6.8 Hz, 6H), 0.80 (d, J=6.8 Hz, 6H) (*including a peak derived from water).

$^{31}$P NMR (161 MHz, CDCl$_3$): δ=−21.95 (s, 2P).

Example 7

Synthesis of (1S,1'S)-N,N'-[1,2-phenylenebis(methylene)]bis[2-(diphenylphosphino)-1-phenyl-ethylamine] (Structural Formula ((S,S)-1$^B$-3)) (Eq. 10)

[Chem. 30]

Eq. 10

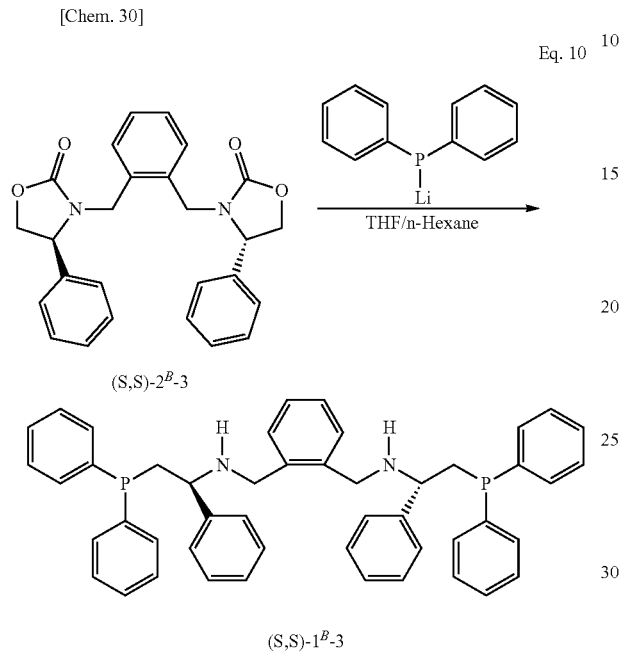

(Setup/Reaction)

A THF/n-hexane solution of lithium diphenylphosphide (52.9 mmol, 2.2 equivalents) was prepared by performing the same operation as in the first step of Example 5. Subsequently, the 50 mL dropping funnel charged with n-BuLi was removed, and a 100 mL dropping funnel was attached instead. Into this dropping funnel were charged 3,3'-[1,2-phenylenebis(methylene)]bis[(S)-4-phenyl-2-oxazolidinone] ((S,S)-2$^B$-3) (10.3 g, 24.0 mmol, 1.0 equivalent) obtained in Example 3 and dehydrated THF (72 mL) successively, and the obtained white suspension was added dropwise into the solution over 30 minutes at a rate keeping the inner temperature at 30° C. or less. The obtained red-orange suspension was stirred with the magnetic stirrer at room temperature for 1 hour.

(Post Treatment/Isolation/Purification)

After the reaction solution was concentrated under reduced pressure, toluene (250 mL) and water (250 mL) were charged thereinto successively, followed by stirring at room temperature, and after standing still, the aqueous layer was separated. The organic layer was washed once with water (50 mL) and then concentrated under reduced pressure to afford the residue, which was purified by silica gel column chromatography (after removing impurities by using toluene as an eluent, the eluent was switched to toluene/ethyl acetate/triethylamine=100/10/1 to elute the target substance) to give 5.5 g of title compound ((S,S)-1$^B$-3) as a pale brown amorphous. Isolated yield: 32.1%.

$^1$H NMR (400 MHz, CDCl$_3$): δ=7.35-7.10 (m, 34H), 3.67-3.57 (m, 2H), 3.49 (d, J=12.8 Hz, 2H), 3.41 (d, J=12.8 Hz, 2H), 2.52-2.39 (m, 4H), 2.30* (bs s, 2H) (*including a peak derived from water).

$^{31}$P NMR (161 MHz, CDCl$_3$): δ=−23.18 (s, 2P).

Example 8

Synthesis of (1S,1'S)-N,N'-[1,2-phenylenebis(methylene)]bis[2-diphenylphosphino)-1-benzyl-ethylamine] (Structural Formula ((S,S)-1$^B$-4)) (Eq. 11)

[Chem. 31]

Eq. 11

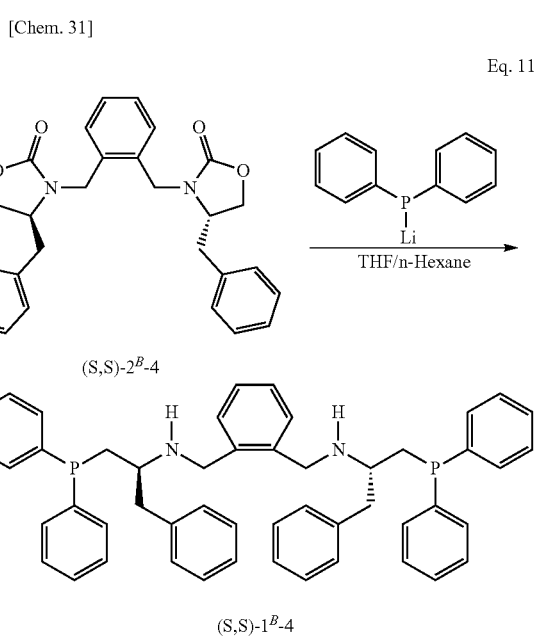

(Setup/Reaction)

A THF/n-hexane solution of lithium diphenylphosphide (52.9 mmol, 2.2 equivalents) was prepared by performing the same operation as in the first step of Example 5. Subsequently, the 50 mL dropping funnel charged with n-BuLi was removed, and a 100 mL dropping funnel was attached instead. Into this dropping funnel were charged 3,3'-[1,2-phenylenebis(methylene)]bis[(S)-4-benzyl-2-oxazolidinone] ((S,S)-2$^B$-4) (11.0 g, 24.0 mmol, 1.0 equivalent) obtained in Example 4 and dehydrated THF (72 mL) successively, dissolved by heating with a heat gun, and then added dropwise into the solution over 30 minutes at a rate keeping the inner temperature at 30° C. or less. The obtained red-orange reaction solution was stirred with the magnetic stirrer at room temperature for 1 hour.

(Post Treatment/Isolation/Purification)

After the reaction solution was concentrated under reduced pressure, toluene (250 mL) and water (250 mL) were charged thereinto successively, followed by stirring at room temperature, and after standing still, the aqueous layer was separated. The organic layer was washed twice with water (50 mL) and then concentrated under reduced pressure to afford the residue, which was purified by silica gel column chromatography (after removing impurities by using toluene as an eluent, the eluent was switched to toluene/ethyl acetate/triethylamine=75/25/1 to elute the target substance) to give 14.8 g of title compound ((S,S)-1$^B$-4) as a pale brown amorphous. Isolated yield: 83.2%. This compound had difficulty in weighing because of its high viscosity, and therefore it was stored as a toluene solution under nitrogen.

$^1$H NMR (400 MHz, CDCl$_3$): δ=7.36-7.29 (m, 4H), 7.28-7.07 (m, 24H), 7.03-6.97 (m, 6H), 3.66 (d, J=12.8 Hz,

2H), 3.62 (d, J=12.8 Hz, 2H), 2.89-2.77 (m, 6H), 2.25-2.11 (m, 4H), 1.65* (br s, 2H) (*including a peak derived from water).

$^{31}$P NMR (161 MHz, CDCl$_3$): δ=−23.32 (s, 2P).

Example 9

Synthesis of N,N'-[1,2-phenylenebis(methylene)]bis[2-(dicyclohexylphosphino)ethylamine]bisborate (Structural Formula ($1^B$-5)) (Eq. 12)

[Chem. 32]

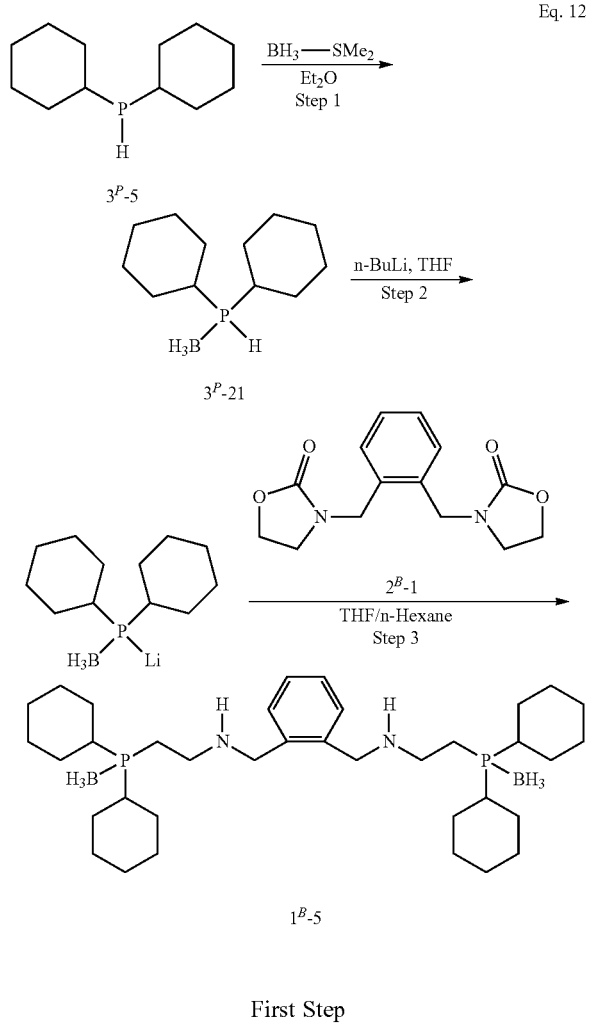

First Step (Setup/Reaction)

A 200 mL four-necked round-bottom flask equipped with a magnetic stirring bar, 20 mL dropping funnel, thermometer and a three-way stopcock was evacuated and filled with nitrogen gas, dicyclohexylphosphine ($3^P$-6) (20.0 mL, 91.2 mmol, 1.0 equivalent) and dehydrated diethyl ether (Et$_2$O) (100 mL) were charged into the flask successively. The obtained solution was cooled to 5° C. by means of an ice-water bath while stirring with a magnetic stirrer. Subsequently, a boron trihydride-dimethylsulfide complex (BH$_3$—SMe$_2$) (concentration: 10.0 mol/L, 13.7 mL, 137.0 mmol, 1.5 equivalents) was charged into the dropping funnel and added dropwise to the solution over 10 minutes at a rate keeping the inner temperature at 10° C. or less, and the temperature of the reaction solution was then raised to room temperature.

(Post Treatment/Isolation/Purification)

After the reaction solution was concentrated under reduced pressure, the obtained residue was dissolved with chloroform (200 mL), and water (100 mL) was then added thereinto, followed by stirring at room temperature, and after standing still, the aqueous layer was separated. The organic layer was concentrated under reduced pressure to afford the residue, which was triturated and then dried under reduced pressure to give 19.3 g of dicyclohexylphosphine-boron trihydride complex ($3^P$-21) as a white powder. This compound was used in the second step without purification.

Second Step (Setup/Reaction)

A 100 mL four-necked round-bottom flask equipped with a magnetic stirring bar, 20 mL dropping funnel, thermometer and a three-way stopcock was evacuated and filled with nitrogen gas, dicyclohexylphosphine-boron trihydride complex ($3^P$-21) (6.0 g, 28.3 mmol, 2.2 equivalents) obtained in the first step and dehydrated THF (28 mL) were charged into the flask successively. The obtained solution was cooled to 5° C. by means of an ice-water bath while stirring with a magnetic stirrer. Subsequently, an n-hexane solution of n-BuLi (concentration: 1.61 mol/L, 17.6 mL, 28.3 mmol, 2.2 equivalents) was charged into the dropping funnel and added dropwise into the solution over 20 minutes at a rate keeping the inner temperature at 10° C. or less. Thereafter, the ice-water bath was removed, and the solution was stirred at room temperature for 20 minutes to give a lithium dicyclohexylphosphide-boron trihydride complex/n-hexane/THF mixture (28.3 mmol, 2.2 equivalents) as a white suspension.

Third Step (Setup/Reaction)

A 200 mL four-necked round-bottom flask equipped with a magnetic stirring bar, 100 mL dropping funnel, thermometer and a three-way stopcock was evacuated and filled with nitrogen gas, 3,3'-[1,2-phenylenebis(methylene)]bis(2-oxazolidinone) ($2^B$-1) (3.6 g, 12.9 mmol, 1.0 equivalent) obtained in Example 1 and dehydrated THF (39 mL) were charged into the flask successively, and the obtained white suspension was stirred with a magnetic stirrer. Subsequently, the lithium dicyclohexylphosphide-boron trihydride complex/n-hexane/THF mixture (28.3 mmol, 2.2 equivalents) obtained in the second step was transferred to the dropping funnel with dehydrated THF (15 mL) and added dropwise into the suspension over 30 minutes at a rate keeping the inner temperature at 30° C. or less. Thereafter, the obtained pale yellow reaction solution was stirred at room temperature for 1 hour.

(Post Treatment/Isolation/Purification)

After the reaction solution was concentrated under reduced pressure, water (100 mL) and chloroform (100 mL) were charged thereinto successively, followed by stirring at room temperature, and after standing still, the aqueous layer was separated. The organic layer was washed once with water (50 mL) and then concentrated under reduced pressure to afford the residue, which was purified by silica gel column chromatography (after removing impurities by using ethyl acetate/triethylamine=50/1 as an eluent, the eluent was switched to ethyl acetate/triethylamine=10/1 to elute the target substance). The eluate was concentrated to afford the residue, to which was added ethyl acetate (20 mL) and followed by stirring, as a result, white crystals were gradually precipitated. To the obtained white suspension was added n-hexane (100 mL), followed by suction filtration, and the crystals collected by filtration were washed with n-hexane (50 mL) and then dried under reduced pressure to give 6.2 g of title compound ($1^B$-5) as a white powder. Isolated yield: 78.7%.

$^1$H NMR (400 MHz, CDCl$_3$): δ=7.31-7.20 (m, 4H), 3.80 (s, 4H), 2.87 (q, J=7.6 Hz, 4H), 2.10-1.60* (m, 28H), 1.41-1.10 (m, 22H), 0.85 to −0.20 (br m, 6H) (*including a peak derived from water).

$^{31}$P NMR (161 MHz, CDCl$_3$): δ=22.56 (d, J=58.0 Hz, 2P).

Example 10

Synthesis of N,N'-[1,2-phenylenebis(methylene)]bis [2-(methylthio)ethylamine] (Structural Formula ($1^B$-6)) (Eq. 13)

[Chem. 33]

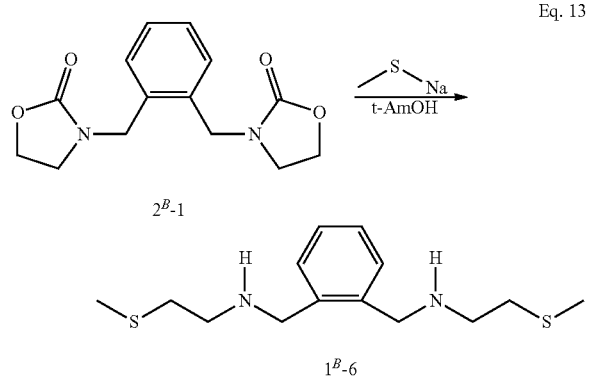

Eq. 13

(Setup/Reaction)

A 200 mL four-necked round-bottom flask equipped with a magnetic stirring bar, condenser, thermometer and a three-way stopcock was evacuated and filled with nitrogen gas, 3,3'-[1,2-phenylenebis(methylene)]bis(2-oxazolidinone) ($2^B$-1) (5.3 g, 19.2 mmol, 1.0 equivalent) obtained in Example 1, 2-methyl-2-butanol (t-AmOH) (80 mL) and sodium methanethiolate (purity: 92.4%, 3.2 g, net weight: 2.96 g, 42.2 mmol, 2.2 equivalents) were charged into the flask successively. The obtained white suspension was heated by means of an oil bath and stirred with a magnetic stirrer for 1 hour under reflux (inner temperature: about 100° C.).

(Post Treatment/Isolation/Purification)

After the reaction solution was cooled to room temperature, water (100 mL) was added thereinto, followed by stirring, and after standing still, the aqueous layer was separated. The aqueous layer was extracted with ethyl acetate (20 mL) three times, and the organic layers were combined and concentrated under reduced pressure. The obtained residue was purified by silica gel column chromatography (eluent: ethyl acetate/triethylamine=10/1) to give 4.1 g of title compound ($1^B$-6) as a pale yellow viscous liquid. Isolated yield: 75.1%.

$^1$H NMR (400 MHz, CDCl$_3$): δ=7.33-7.27 (m, 2H), 7.26-7.21 (m, 2H), 3.84 (s, 4H), 2.85 (t, J=6.4 Hz, 4H), 2.67 (t, J=6.4 Hz, 4H), 2.08* (s, 6H), 2.08* (br s, 2H). (*Peaks derived from methyl group, imino group and water were observed overlappedly)

$^{13}$C NMR (100 MHz, CDCl$_3$): δ=138.74, 130.07, 127.32, 51.80, 47.58, 34.45, 15.31.

Example 11

Synthesis of N,N'-[1,2-phenylenebis(methylene)]bis [2-(p-tolylthio)ethylamine] (Structural Formula ($1^B$-7)) (Eq. 14)

[Chem. 34]

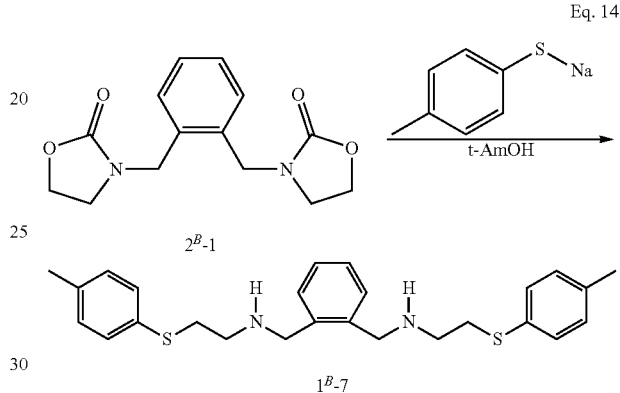

Eq. 14

(Setup/Reaction)

A 100 mL four-necked round-bottom flask equipped with a magnetic stirring bar, condenser, thermometer and a three-way stopcock was evacuated and filled with nitrogen gas, 3,3'-[1,2-phenylenebis(methylene)]bis(2-oxazolidinone) ($2^B$-1) (2.5 g, 9.05 mmol, 1.0 equivalent) obtained in Example 1, t-AmOH (36 mL) and sodium p-toluenethiolate (purity: 98.3%, 3.0 g, net weight: 2.95 g, 19.9 mmol, 2.2 equivalents) were charged into the flask successively. The obtained white suspension was heated by means of an oil bath and stirred with a magnetic stirrer for 1 hour under reflux (inner temperature: about 100° C.).

(Post Treatment/Isolation/Purification)

After the reaction solution was cooled to room temperature, water (36 mL) was added thereinto, followed by stirring, and after standing still, the aqueous layer was separated. The aqueous layer was extracted once with ethyl acetate (10 mL), and the organic layers were combined and concentrated under reduced pressure. The obtained residue was purified by silica gel column chromatography (after removing impurities by using ethyl acetate/triethylamine=50/1 as an eluent, the eluent was switched to ethyl acetate/triethylamine=10/1 to elute the target substance) to give 3.7 g of title compound ($1^B$-7) as a pale yellow viscous liquid. Isolated yield: 93.6%. This compound had difficulty in weighing because of its high viscosity, and therefore it was stored as a toluene solution in air.

$^1$H NMR (400 MHz, CDCl$_3$): δ=7.27-7.19 (m, 8H), 7.10-7.04 (m, 4H), 3.79 (s, 4H), 3.02 (t, J=6.4 Hz, 4H), 2.84 (t, J=6.4 Hz, 4H), 2.31 (s, 6H), 2.11* (br s, 2H) (*including a peak derived from water).

$^{13}$C NMR (100 MHz, CDCl$_3$): δ=138.69, 136.28, 132.06, 130.34, 130.07, 129.68, 51.70, 47.92, 34.86, 20.98.

Example 12

Synthesis of (1S,1'S)-N,N'-[1,2-phenylenebis(methylene)]bis[2-(p-tolylthio)-1-benzyl-ethylamine] (Structural Formula ((S,S)-1$^B$-8)) (Eq. 15)

[Chem. 35]

Eq. 15

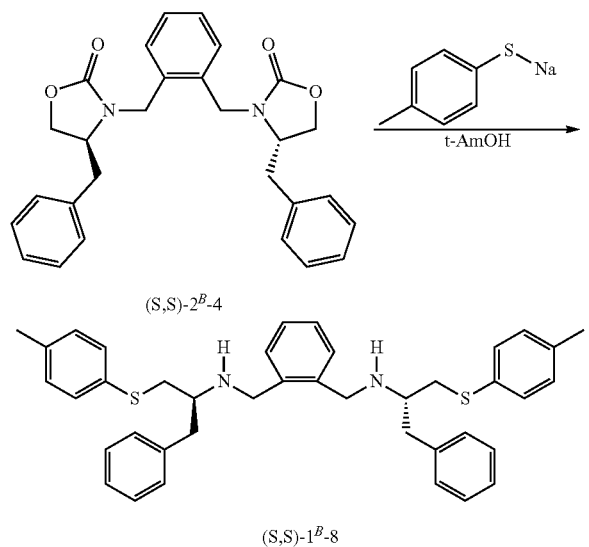

(Setup/Reaction)

A 100 mL four-necked round-bottom flask equipped with a magnetic stirring bar, condenser, thermometer and a three-way stopcock was evacuated and filled with nitrogen gas, 3,3'-[1,2-phenylenebis(methylene)]bis[(S)-4-benzyl-2-oxazolidinone] ((S,S)-2$^B$-4)) (2.8 g, 6.11 mmol, 1.0 equivalent) obtained in Example 4, t-AmOH (24 mL) and sodium p-toluenethiolate (purity: 98.3%, 2.0 g, net weight: 1.97 g, 13.45 mmol, 2.2 equivalents) were charged into the flask successively. The obtained white suspension was heated by means of an oil bath and stirred with a magnetic stirrer for 1 hour under reflux (inner temperature: about 100° C.).

(Post Treatment/Isolation/Purification)

After the reaction solution was cooled to room temperature, water (25 mL) and ethyl acetate (25 mL) were added thereinto successively, followed by stirring, and after standing still, the aqueous layer was separated. The organic layer was concentrated under reduced pressure to afford the residue, which was purified by silica gel column chromatography (after removing impurities by using toluene/ethyl acetate/triethylamine=100/20/1 as an eluent, the eluent was switched to toluene/ethyl acetate/triethylamine=50/25/1 to elute the target substance) to give 3.5 g of title compound (1$^B$-8) as a pale yellow viscous liquid. Isolated yield: 92.9%. This compound had difficulty in weighing because of its high viscosity, and therefore it was stored as a toluene solution in air.

$^1$H NMR (400 MHz, CDCl$_3$): δ=7.26-7.00 (m, 22H), 3.73 (d, J=12.8 Hz, 2H), 3.66 (d, J=12.8 Hz, 2H), 3.03-2.94 (m, 4H), 2.93-2.86 (m, 2H), 2.82 (d, J=6.4 Hz, 4H), 2.30 (s, 6H), 1.75* (br s, 2H) (*including a peak derived from water).

$^{13}$C NMR (100 MHz, CDCl$_3$): δ=138.78, 138.47, 136.00, 132.71, 129.93, 129.71, 129.65, 129.32, 128.38, 127.17, 126.26, 57.98, 48.97, 40.06, 38.40, 20.97.

Example 13

Synthesis of cis-α-dichloro{N,N'-[1,2-phenylenebis(methylene)]bis[2-(diphenylphosphino)ethylamine]}ruthenium(II) (Structural Formula (cis-α-RuCl$_2$(1$^B$-1))) (Eq. 16)

[Chem. 36]

Eq. 16

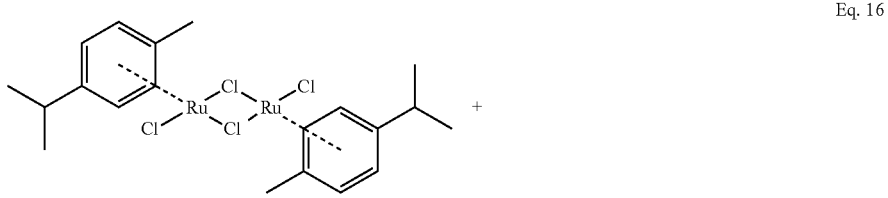

([RuCl$_2$(p-cymene)]$_2$)

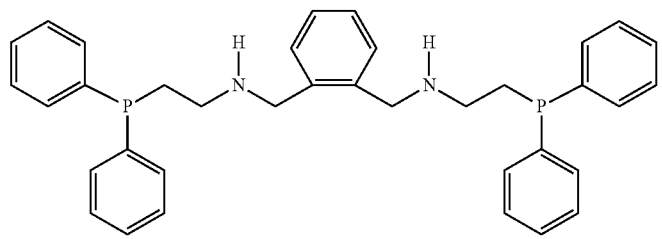

1$^B$-1

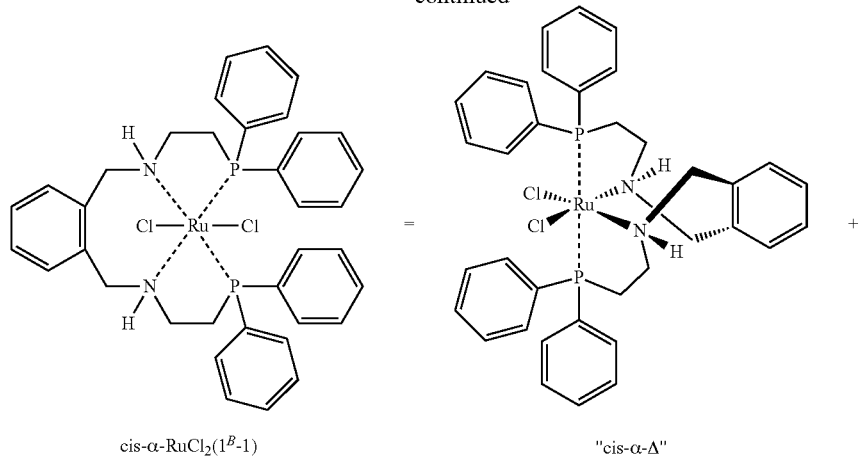

cis-α-RuCl₂(1ᴮ-1)     "cis-α-Δ"

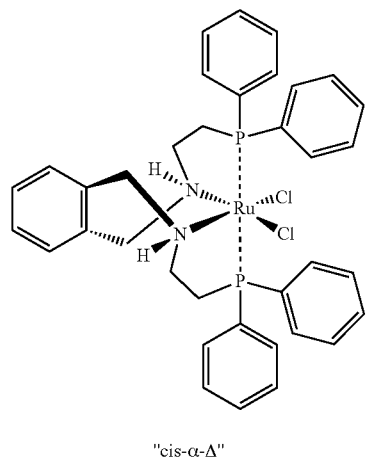

"cis-α-Λ"

(Setup/Reaction)

A 200 mL four-necked round-bottom flask equipped with a magnetic stirring bar, Claisen distillation apparatus, thermometer and a three-way stopcock was evacuated and filled with nitrogen gas, a toluene solution of N,N-[1,2-phenylenebis(methylene)]bis[2-(diphenylphosphino)ethylamine] (1ᴮ-1) (purity: 20.0%, 30.3 g, net weight: 6.06 g, 10.81 mmol, 2.2 equivalents) obtained in Example 5 was charged into the flask, and toluene was distilled off under reduced pressure. Thereafter, the Claisen distillation apparatus was removed, a condenser was attached to the flask, and 1-butanol (1-BuOH) (49 mL) and dichloro(p-cymene)ruthenium (II) dimer ([RuCl₂(p-cymene)]₂) (3.0 g, 4.91 mmol, 1.0 equivalent) were charged into the flask successively. The obtained red suspension was heated by means of an oil bath and stirred with a magnetic stirrer for 1 hour under reflux (inner temperature: about 110° C.).

(Post Treatment/Isolation/Purification)

The obtained orange slurry was cooled to 5° C. by means of an ice-water bath, and methanol (50 mL) was then added, followed by suction filtration. The obtained orange powder was washed with cold methanol (−20° C., 50 mL) and then dried under reduced pressure to give 6.40 g of title compound (cis-α-RuCl₂(1ᴮ-1)) as an orange powder. Isolated yield: 89.0%.

$^1$H NMR (400 MHz, CDCl₃): δ=7.42-7.26 (m, 10H), 7.16-6.98 (m, 10H), 6.91-6.84 (m, 4H), 5.19 (t, J=11.2 Hz, 2H), 3.74-3.58 (m, 4H), 3.50-3.22 (m, 4H), 2.81-2.69 (m, 2H), 2.39-2.26 (m, 2H).

$^{31}$P NMR (161 MHz, CDCl₃): δ=60.10 (s, 2P).

HRMS: mass-to-charge ratio (hereinafter, abbreviated as m/z)=732.0936, compositional formula of molecular-mass ion (hereinafter, abbreviated as M) of title compound=$C_{36}H_{38}Cl_2N_2P_2Ru$.

As seen from the results of $^{31}$P NMR measurement, two phosphorus atoms in the title compound obtained by this synthesis method have the same valence and therefore, the coordination form of the title compound is limited to either trans having no asymmetry or cis-α having asymmetry. On the other hand, when an excess amount of (S)-(+)-2,2,2-trifluoro-1-(9-anthryl)ethanol was added to the title compound and chiral shift NMR measurement was performed, clear separation of peaks was observed in both $^1$H NMR and $^{31}$P NMR. Accordingly, it was revealed that the coordination form of the title compound is cis-α and the title compound is a mixture (i.e., racemic form) of equal parts of Δ form and Λ form.

Example 14

Synthesis of cis-β-dichloro{N,N'-[1,2-phenylenebis(methylene)]bis[2-(diphenylphosphino)ethylamine]}ruthenium(II) (Structural Formula (cis-β-RuCl$_2$(1$^B$-1))) (Eq. 17)

[Chem. 37]

Eq. 17

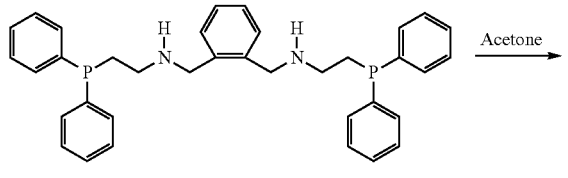
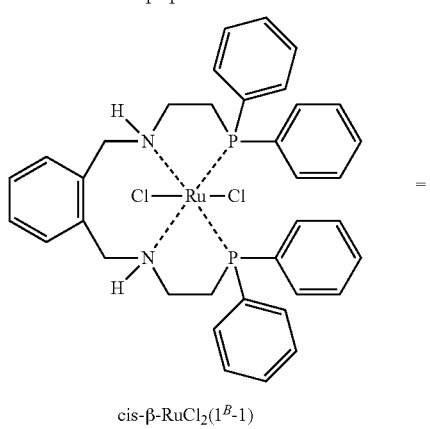
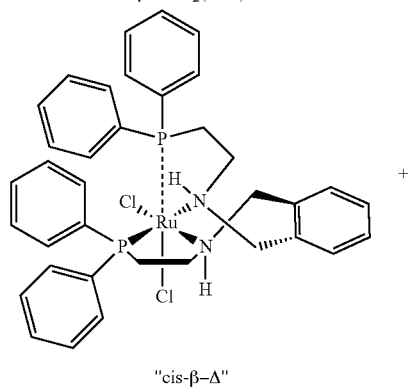
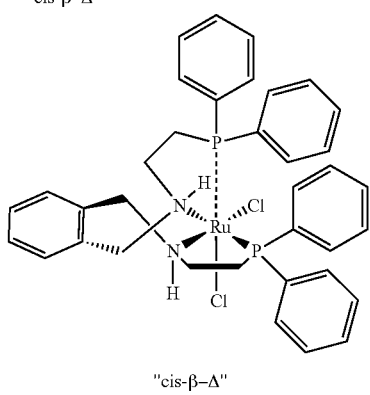

(Setup/Reaction)

A 100 mL four-necked round-bottom flask equipped with a magnetic stirring bar, Claisen distillation apparatus, thermometer and a three-way stopcock was evacuated and filled with nitrogen gas, a toluene solution of N,N'-[1,2-phenylenebis(methylene)]bis[2-(diphenylphosphino)ethylamine] (1$^B$-1) (purity: 20.0%, 10.0 g, net weight: 2.0 g, 3.57 mmol, 1.1 equivalents) obtained in Example 5 was charged into the flask, and toluene was distilled off under reduced pressure. Thereafter, the Claisen distillation apparatus was removed, a condenser was attached to the flask, and dehydrated acetone (30 mL) and dichlorotris(triphenylphosphine)ruthenium(II) (RuCl$_2$(PPh$_3$)$_3$) (3.1 g, 3.25 mmol, 1.0 equivalent) were charged into the flask successively. The obtained dark brown suspension was heated by means of an oil bath and stirred with a magnetic stirrer for 1 hour under reflux (inner temperature: about 55° C.).

(Post Treatment/Isolation/Purification)

The obtained yellow slurry was cooled to room temperature, and n-hexane (30 mL) was then added, followed by suction filtration. The obtained yellow powder was washed with a mixed solution of n-hexane/acetone=1/1 and then dried under reduced pressure to give 1.91 g of title compound (cis-β-RuCl$_2$(1$^B$-1)) as a yellow powder. Isolated yield: 80.3%.

$^1$H NMR (400 MHz, CD$_2$Cl$_2$): δ=8.14-8.06 (m, 2H), 7.64-7.41 (m, 7H), 7.39-7.25 (m, 4H), 7.24-7.15 (m, 3H), 7.07-6.98 (m, 4H), 6.96-6.89 (m, 2H), 6.21-6.13 (m, 2H), 5.47 (dd, J=2.8, 12.4 Hz, 1H), 5.14 (br s, 1H), 4.99 (t, J=11.2 Hz, 1H), 3.89 (ddd, J=2.8, 6.0, 12.4 Hz, 1H), 3.75-3.59 (m, 1H), 3.34-3.15 (m, 1H), 3.09 (d, J=12.0 Hz, 1H), 3.09-2.93 (m, 1H), 2.74-2.52 (m, 2H), 1.88-1.78 (m, 1H), 1.68-1.45 (m, 2H), 1.22-1.09 (m, 1H).

$^{31}$P NMR (161 MHz, CD$_2$Cl$_2$): δ=60.72 (d, J=34.0 Hz, 1P), 53.34 (d, J=34.0 Hz, 1P).

As seen from the results of $^{31}$P NMR measurement, two phosphorus atoms in the title compound obtained by this synthesis method are non-equivalent and therefore, the coordination form of the title compound is cis-β form having asymmetry. Actually, when an excess amount of (S)-(+)-2,2,2-trifluoro-1-(9-anthryl)ethanol was added to the title compound and chiral shift NMR measurement was performed, clear separation of peaks was observed in both $^1$H NMR and $^{31}$P NMR. Accordingly, it was revealed that the coordination form of the title compound is cis-β form and the title compound is a mixture (i.e., racemic form) of equal parts of Δ form and Λ form.

Example 15

Synthesis of chlorohydride{N,N'-[1,2-phenylenebis(methylene)]bis[2-diphenylphosphino)ethylamine]}ruthenium(II) (Structural Formula (RuHCl($1^B$-1))) (Eq. 18)

[Chem. 38]

Eq. 18

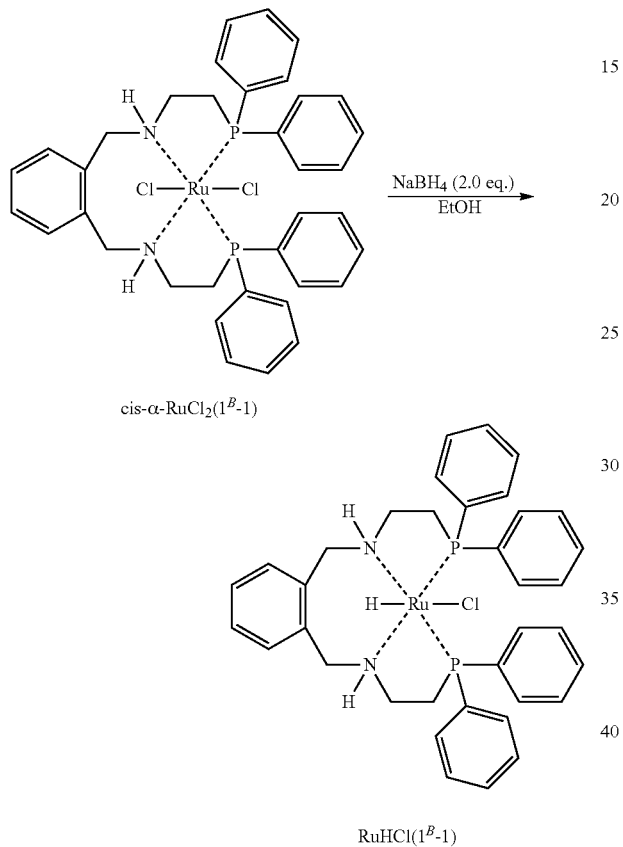

(Setup/Reaction)

A 100 mL four-necked round-bottom flask equipped with a magnetic stirring bar, condenser, thermometer and a three-way stopcock was evacuated and filled with nitrogen, sodium borohydride (NaBH$_4$) (105 mg, 2.73 mmol, 2.0 equivalents), dehydrated ethanol (100 mL) and cis-α-RuCl$_2$ ($1^B$-1) (1.0 g, 1.37 mmol, 1.0 equivalent) obtained in Example 13 were charged into the flask successively. The obtained orange slurry was heated by means of an oil bath while stirring a the magnetic stirrer and heated for 3 hours under reflux.

(Post Treatment/Isolation)

The condenser was removed from the flask, a Claisen distillation apparatus was attached instead, and 60 mL of ethanol was recovered under nitrogen stream and atmospheric pressure (oil bath: 110° C., inner temperature: 76° C.). The obtained yellow-orange slurry was cooled to 5° C. by means of an ice-water bath, and degassed water (40 mL) was added thereinto, followed by suction filtration under nitrogen steam. The obtained yellow powder was washed with degassed 50% hydrous ethanol, degassed water and degassed 50% hydrous ethanol successively, and dried under reduced pressure at room temperature to give 873 mg of title compound (RuHCl($1^B$-1)) as a yellow-orange powder unstable to air. Isolated yield: 91.6%.

$^1$H NMR (400 MHz, C$_6$D$_6$) (a region of 0 ppm or less is shown): −18.83 (major, t, J=26.8 Hz, 0.8H), −19.92 (minor, t, J=30.0 Hz, 0.2H).

$^{31}$P NMR (161 MHz, C$_6$D$_6$): δ=77.50 (major, s, 1.6P), 77.35 (minor, s, 0.4P).

It was revealed by the NMR measurement that the title compound has Ru—H bond and is a mixture of two kinds of coordination isomers.

Example 16

Synthesis of hydrideborohydride{N,N'-[1,2-phenylenebis(methylene)]bis[2-(diphenylphosphino)ethylamine]}ruthenium(II) (Structural Formula (RuH(BH$_4$)($1^B$-1))) (Eq. 19)

[Chem. 39]

Eq. 19

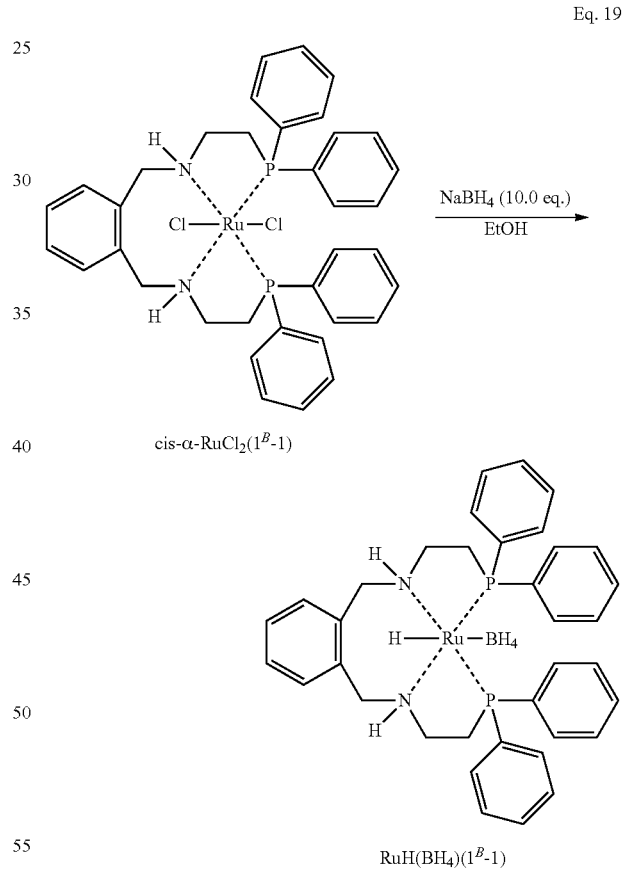

(Setup/Reaction)

A 100 mL four-necked round-bottom flask equipped with a magnetic stirring bar, condenser, thermometer and a three-way stopcock was evacuated and filled with nitrogen gas, NaBH$_4$ (527 mg, 13.65 mmol, 10.0 equivalents), dehydrated ethanol (100 mL) and cis-α-RuCl$_2$($1^B$-1) (1.0 g, 1.37 mmol, 1.0 equivalent) obtained in Example 13 were charged into the flask successively. The obtained orange slurry was heated by means of an oil bath while stirring with a magnetic stirrer and heated for 1 hour under reflux.

(Post Treatment/Isolation)

The condenser was removed from the flask, a Claisen distillation apparatus was attached instead, and 70 mL of ethanol was recovered under nitrogen stream and atmospheric pressure (oil bath: 110° C., inner temperature: 76° C.). The obtained yellow slurry was cooled to 5° C. by means of an ice-water bath, and degassed water (30 mL) was added thereinto, followed by suction filtration under nitrogen steam. The obtained yellow powder was washed with degassed 50% hydrous ethanol, degassed water, degassed 50% hydrous ethanol and degassed ethanol successively, and dried under reduced pressure at room temperature to give 940 mg of title compound (RuH(BH$_4$)(1$^B$-1)) as a yellow powder, which was unstable to air. The isolated yield was quantitative.

$^1$H NMR (400 MHz, C$_6$D$_6$) (a region of 0 ppm or less is shown): −0.45 to −2.10 (br m, 4H), −14.89 (major, t, J=24.8 Hz, 0.7H), −16.08 (minor, t, J=25.2 Hz, 0.3H).

$^{31}$P NMR (161 MHz, C$_6$D$_6$): δ=80.80 (major, br s, 1.4P), 80.12 (minor, br s, 0.6P).

It was revealed by the NMR measurement that the title compound has Ru—H bond and Ru-η$^1$-BH$_4$ bond and is a mixture of two kinds of coordination isomers.

Example 17

Synthesis of dibenzoate{N,N'-[1,2-phenylenebis(methylene)]bis[2-(diphenylphosphino)ethylamine]}ruthenium(II) (Structural Formula (Ru(OBz)$_2$(1$^B$-1))) (Eq. 20)

[Chem. 40]

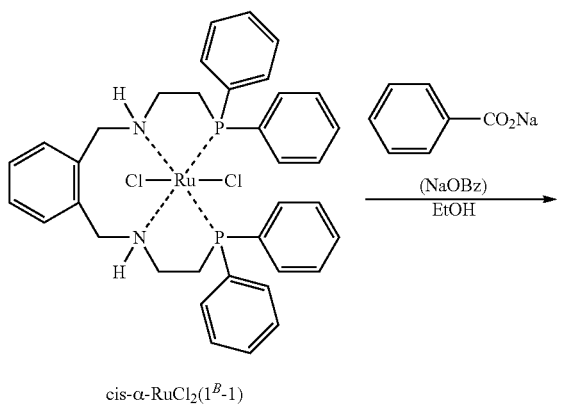

Eq. 20

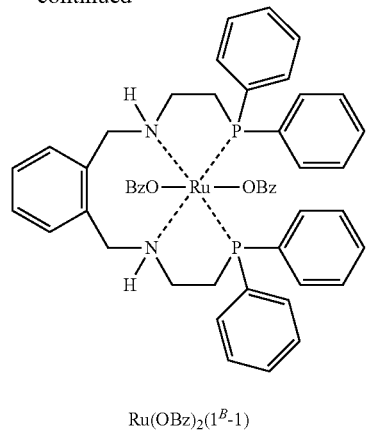

Ru(OBz)$_2$(1$^B$-1)

(Setup/Reaction)

A 100 mL four-necked round-bottom flask equipped with a magnetic stirring bar, condenser, thermometer and a three-way stopcock was evacuated and filled with nitrogen gas, cis-α-RuCl$_2$(1$^B$-1) (500 mg, 0.682 mmol, 1.0 equivalent) obtained in Example 13, dehydrated ethanol (50 mL) and sodium benzoate (492 mg, 3.41 mmol, 5.0 equivalents) were charged into the flask successively. The obtained orange slurry was heated by means of an oil bath while stirring with a magnetic stirrer and stirred for 2 hours under reflux.

(Post Treatment/Isolation/Purification)

After the reaction solution was concentrated under reduced pressure, a slurry obtained by adding toluene (100 mL) was filtered by suction with diatomaceous earth, and the filtrate was concentrated under reduced pressure. The obtained residue was purified by silica gel column chromatography (eluent: toluene/ethyl acetate=5/1 to 3/1) and crystallization from toluene/n-hexane to give 332 mg of title compound (Ru(OBz)$_2$(1$^B$-1)) as a yellow powder. Isolated yield: 53.9%.

$^{31}$P NMR (161 MHz, CD$_2$Cl$_2$): δ1.65 (major, s, 1.8P), 59.68 (minor, s, 0.2P).

It was revealed by the $^{31}$P NMR measurement that the title compound is a mixture of two kinds of coordination isomers.

Example 18

Synthesis of dipivalato{N,N'-[1,2-phenylenebis(methylene)]bis[2-(diphenylphosphino)ethylamine]}ruthenium(II) (Structural Formula (Ru(OPiv)$_2$(1$^B$-1))) (Eq. 21)

[Chem. 41]

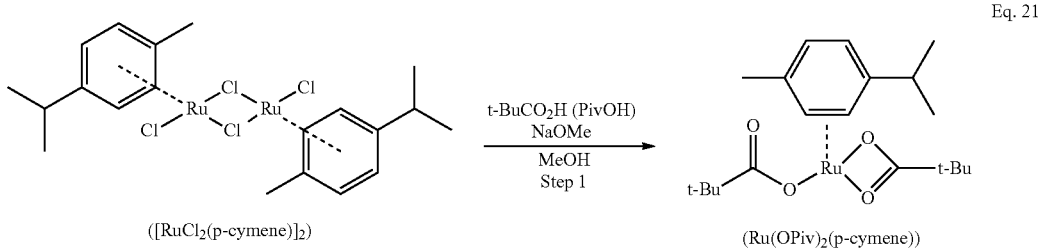

Eq. 21

-continued

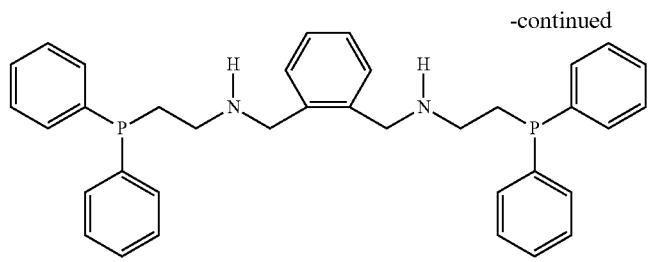

1$^B$-1

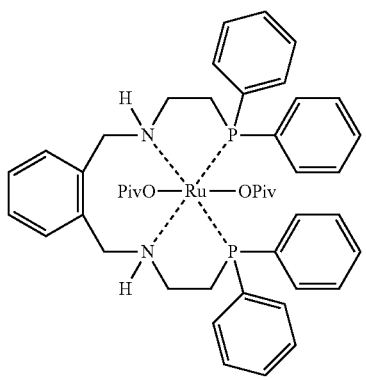

Ru(OPiv)$_2$(1$^B$-1)

First Step: Synthesis of dipivalato(p-cymene)ruthenium(II) (Ru(OPiv)$_2$(p-cymene))

(Setup/Reaction)

A 200 mL four-necked round-bottom flask equipped with a magnetic stirring bar, dropping funnel, thermometer and a three-way stopcock was evacuated and filled with nitrogen gas, pivalic acid (3.67 g, 35.9 mmol, 4.4 equivalents) and dehydrated methanol (60 mL) were charged into the flask successively, and the obtained solution was stirred at room temperature by means of a magnetic stirrer. Subsequently, a methanol solution of sodium methoxide (concentration: 28.4%, 6.52 g, net weight: 1.85 g, 34.3 mmol, 4.2 equivalents) was charged into the dropping funnel and added dropwise into the solution over 15 minutes at a rate keeping the inner temperature at 30° C. or less, and the dropping funnel was then co-washed with dehydrated methanol (5 mL). After the obtained reaction solution was stirred for 30 minutes at room temperature, [RuCl$_2$(p-cymene)]$_2$ (5.0 g, 8.16 mmol, 1.0 equivalent) was added thereinto, followed by stirring at room temperature for 3 hours.

(Post Treatment/Isolation/Purification)

The red-brown suspension obtained after the reaction was concentrated under reduced pressure, chloroform (100 mL) was added thereinto, followed by suction filtration with diatomaceous earth, and the filtrate was concentrated under reduced pressure. To the obtained residue were added chloroform (10 mL) and n-hexane (100 mL) successively, as a result, an orange slurry was obtained. This slurry was cooled to −30° C., and crystals were then collected by suction filtration and washed with cold n-hexane (−70° C.). The obtained crystals were dried under reduced pressure to give 4.33 g of Ru(OPiv)$_2$(p-cymene) as a yellow-orange powder. Isolated yield: 60.6%.

$^1$H NMR (400 MHz, CDCl$_3$): δ=5.71 (d, J=6.0 Hz, 2H), 5.49 (d, J=6.0 Hz, 2H), 2.89 (sept, J=6.8 Hz, 1H), 2.25 (s, 3H), 1.35 (d, J=6.8 Hz, 6H), 1.07 (s, 18H).

Second Step: Synthesis of Ru(OPiv)$_2$(1$^B$-1)

(Setup/Reaction)

A 50 mL four-necked round-bottom flask equipped with a magnetic stirring bar, condenser, thermometer and a three-way stopcock was evacuated and filled with nitrogen gas, a toluene solution of N,N'-[1,2-phenylenebis(methylene)]bis[2-(diphenylphosphino)ethylamine] (1$^B$-1) (purity: 20.0%, 2.50 g, net weight: 500 mg, 0.892 mmol, 1.1 equivalents) obtained in Example 5, dehydrated toluene (16 mL) and Ru(OPiv)$_2$(p-cymene) (355 mg, 0.811 mmol, 1.0 equivalent) obtained in the first step were charged into the flask successively. The obtained solution was heated by means of an oil bath while stirring with a magnetic stirrer and stirred for 8 hours under reflux conditions.

(Post Treatment/Isolation/Purification)

The obtained reaction solution was concentrated under reduced pressure to afford the residue, which was purified by silica gel column chromatography (eluent: toluene/ethyl acetate=5/1 to 3/1) to give 141 mg of title compound (Ru(OPiv)$_2$(1$^B$-1)) as a yellow powder. Isolated yield: 20.1%.

$^{31}$P NMR (161 MHz, C$_6$D$_6$): 64.41 (minor, s, 0.3P), 61.33 (major, s, 1.7P).

It was revealed by the $^{31}$P NMR measurement that the title compound is a mixture of two kinds of coordination isomers.

Example 19

Synthesis of dichloro{(1S,1'S)-N,N'-[1,2-phenylenebis(methylene)]bis[2-(diphenylphosphino)-1-isopropyl-ethylamine]}ruthenium(II) (Structural Formula (RuCl$_2$[(S,S)-1$^B$-2])) (Eq. 22)

[Chem. 42]

Eq. 22

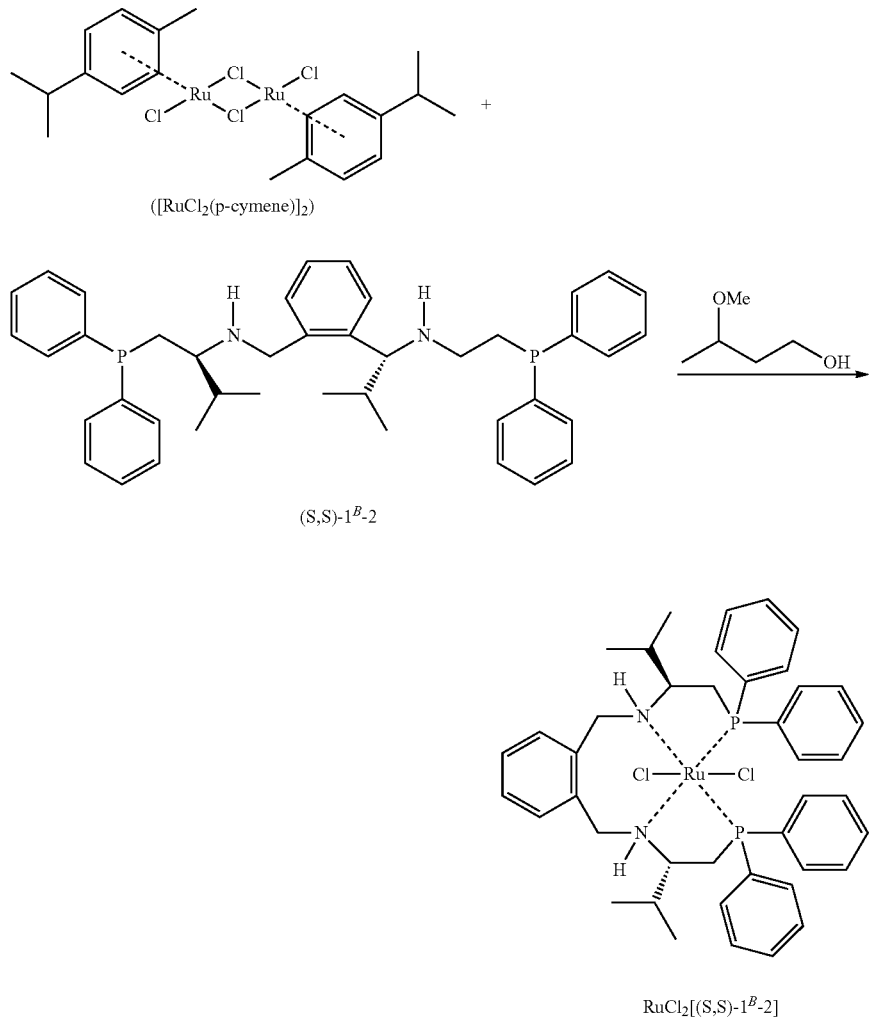

(Setup/Reaction)

A 100 mL four-necked round-bottom flask equipped with a magnetic stirring bar, Claisen distillation apparatus, thermometer and a three-way stopcock was evacuated and filled with nitrogen, a toluene solution of (1S,1'S)-N,N'-[1,2-phenylenebis(methylene)]bis[2-(diphenylphosphino)-1-isopropyl-ethylamine] ((S,S)-1$^B$-2) (purity: 20.0%, 10.0 g, net weight: 2.0 g, 3.10 mmol, 2.2 equivalents) obtained in Example 6 was charged into the flask, and toluene was distilled off under reduced pressure. Thereafter, the Claisen distillation apparatus was removed, a condenser was attached to the flask, 3-methoxy-1-butanol (26 mL) and [RuCl$_2$(p-cymene)]$_2$ (863 mg, 1.41 mmol, 1.0 equivalent) were added into the flask successively. The obtained red suspension was heated by means of an oil bath and stirred with a magnetic stirrer for 1 hour under reflux (inner temperature: about 150° C.).

(Post Treatment/Isolation/Purification)

The red-orange slurry suspension obtained after the reaction was cooled to room temperature and then diluted with methanol (26 mL), followed by suction filtration, and the obtained crystals were washed with methanol (50 mL). The resulting wet crystals were once dissolved in chloroform (50 mL) and then evaporated to dryness under reduced pressure to give 1.15 g of title compound (RuCl$_2$[(S,S)-1$^B$-2]) as a red-brown powder. Isolated yield: 49.9%.

$^{31}$P NMR (161 MHz, CDCl$_3$): δ=59.60 (s, 2P).

HRMS: m/z=816.1876, M=C$_{42}$H$_{50}$Cl$_2$N$_2$P$_2$Ru.

When $^1$H NMR measurement of the title compound was performed, a broad peak was observed over the range of 0 to 8 ppm. This is considered to result because the internal molecular motion was inhibited by steric hindrance due to two isopropyl groups.

Example 20

Synthesis of dichloro{N,N'-[1,2-phenylenebis(methylene)]bis[2-(methylthio)ethylamine]}ruthenium(II) (Structural Formula (RuCl$_2$(1$^B$-6))) (Eq. 23)

[Chem. 43]

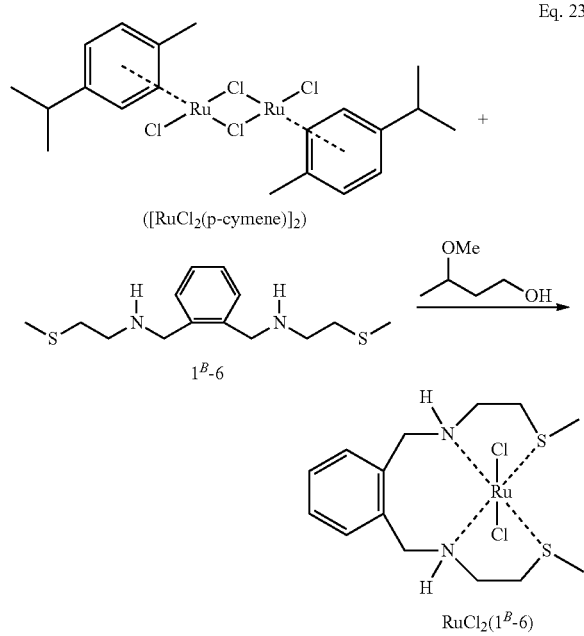

Eq. 23

(Setup/Reaction)

A 50 mL four-necked round-bottom flask equipped with a magnetic stirring bar, condenser, thermometer and a three-way stopcock was evacuated and filled with nitrogen gas, N,N'-[1,2-phenylenebis(methylene)]bis[2-(methylthio)ethylamine] (1$^B$-6) (500 mg, 1.76 mmol, 2.2 equivalents) obtained in Example 10, 3-methoxy-1-butanol (16 mL) and [RuCl$_2$(p-cymene)]$_2$ (490 mg, 0.80 mmol, 1.0 equivalent) were charged into the flask successively. The obtained red suspension was heated by means of an oil bath and stirred with a magnetic stirrer for 2 hours under reflux (inner temperature: about 155° C.).

(Post Treatment/Isolation/Purification)

The reaction solution was concentrated under reduced pressure to give the residue, which was then purified by silica gel column chromatography (eluent: chloroform/ethyl acetate=2/1) to give 589 mg of title compound (RuCl$_2$(1$^B$-6)) as a pale red powder. Isolated yield: 80.6%.

HRMS: m/z=455.9873, M=C$_{14}$H$_{24}$Cl$_2$N$_2$RuS$_2$.

By $^1$H NMR analysis, the title compound was found to be a mixture of coordination isomers. This phenomenon of coordination isomerism is considered to derive from two lone electron pairs on sulfur atom.

Example 21

Synthesis of dichloro{N,N'-[1,2-phenylenebis(methylene)]bis[2-(p-tolylthio)ethylamine]}ruthenium(II) (Structural Formula (RuCl$_2$(1$^B$-7))) (Eq. 24)

[Chem. 44]

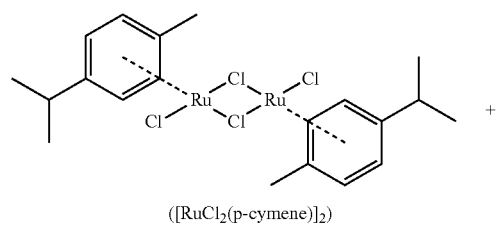

Eq. 24

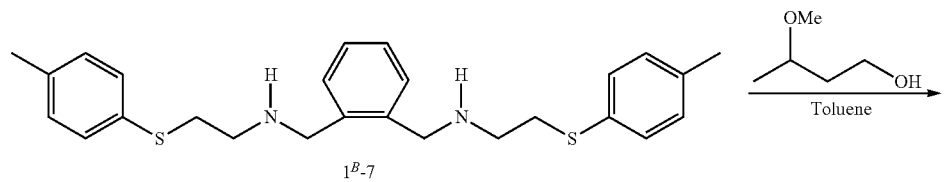

-continued

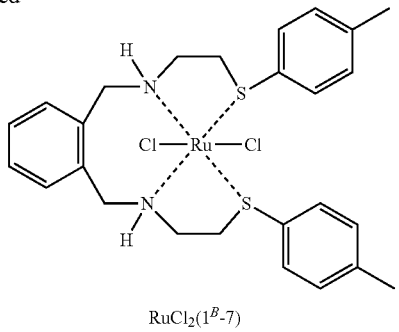

RuCl$_2$(1$^B$-7)

(Setup/Reaction)

A 50 mL four-necked round-bottom flask equipped with a magnetic stirring bar, condenser, thermometer and a three-way stopcock was evacuated and filled with nitrogen gas, a toluene solution of N,N'-[1,2-phenylenebis(methylene)]bis[2-(p-tolylthio)ethylamine] (1$^B$-7) (purity: 19.9%, 2.51 g, net weight: 500 mg, 1.15 mmol, 2.2 equivalents) obtained in Example 11, 3-methoxy-1-butanol (10 mL) and [RuCl$_2$(p-cymene)]$_2$ (319 mg, 0.52 mmol, 1.0 equivalent) were charged into the flask successively. The obtained red suspension was heated by means of an oil bath and stirred with a magnetic stirrer for 1 hour under reflux (inner temperature: about 137° C.).

(Post Treatment/Isolation/Purification)

A red suspension obtained by cooling the reaction solution to room temperature was diluted with methanol (20 mL) and subjected to suction filtration. The obtained crystals were washed with methanol (20 mL) and then dried under reduced pressure to give 440 mg of title compound (RuCl$_2$ (1$^B$-7)) as a red-brown powder. Isolated yield: 69.1%.

HRMS: m/z=608.4028, M=C$_{26}$H$_{32}$Cl$_2$N$_2$RuS$_2$.

By $^1$H NMR analysis, the title compound was found to be a mixture of coordination isomers, similarly to Example 20.

Example 22

Synthesis of dichloro{(1S,1'S)-N,N'-[1,2-phenylenebis(methylene)]bis[2-(p-tolylthio)-1-benzyl-ethylamine]}ruthenium(II) (Structural Formula (RuCl$_2$ [(S,S)-1$^B$-8])) (Eq. 25)

[Chem. 45]

Eq. 25

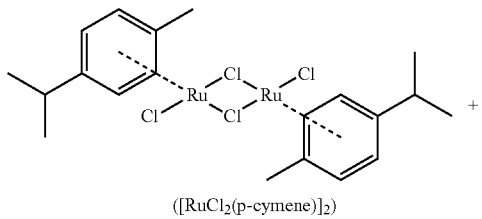

([RuCl$_2$(p-cymene)]$_2$)

+

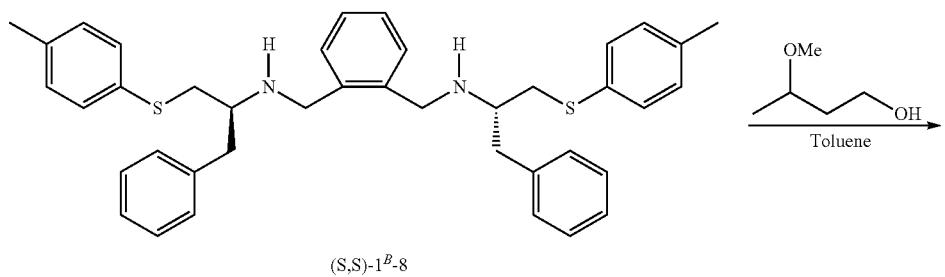

(S,S)-1$^B$-8

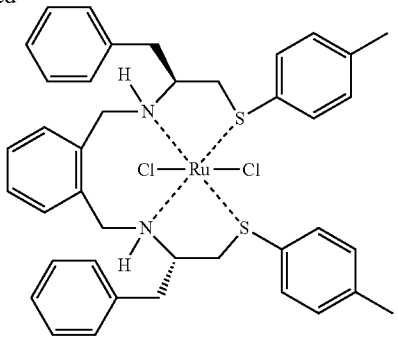

RuCl₂[(S,S)-1^B-8]

(Setup/Reaction)

A 50 mL four-necked round-bottom flask equipped with a magnetic stirring bar, condenser, thermometer and a three-way stopcock was evacuated and filled with nitrogen gas, a toluene solution of (1S,1'S)-N,N'-[1,2-phenylenebis(methylene)]bis[2-(p-tolylthio)-1-benzyl-ethylamine] ((S,S)-1^B-8) (purity: 20.0%, 2.5 g, net weight: 500 mg, 0.81 mmol, 2.2 equivalents) obtained in Example 12, 3-methoxy-1-butanol (7.5 mL) and [RuCl₂(p-cymene)]₂ (226 mg, 0.37 mmol, 1.0 equivalent) were charged into the flask successively. The obtained red suspension was heated by means of an oil bath and stirred with a magnetic stirrer for 1 hour under reflux (inner temperature: about 130° C.).

(Post Treatment/Isolation/Purification)

The reaction solution was concentrated under reduced pressure to afford the residue, which was purified by silica gel column chromatography (eluent: toluene/ethyl acetate=5/1) to give 410 mg of title compound (RuCl₂[(S,S)-1^B-8]) as a pale red powder. Isolated yield: 70.2%.

HRMS: m/z=788.1390, M=C₄₀H₄₄Cl₂N₂RuS₂.

By ¹H NMR analysis, the title compound was found to be a mixture of coordination isomers, similarly to Examples 20 and 21.

Example 23

Synthesis of dichloro{N,N'-[1,2-phenylenebis(methylene)]bis[2-(diphenylphosphino)ethylamine]}iron (II) (Structural Formula (FeCl₂(1^B-1))) (Eq. 26)

[Chem. 46]

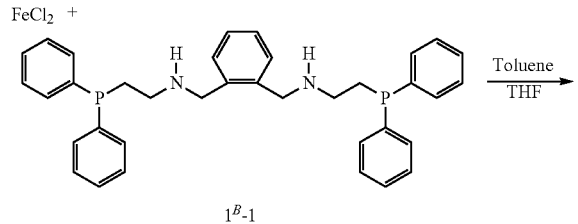

Eq. 26

1^B-1

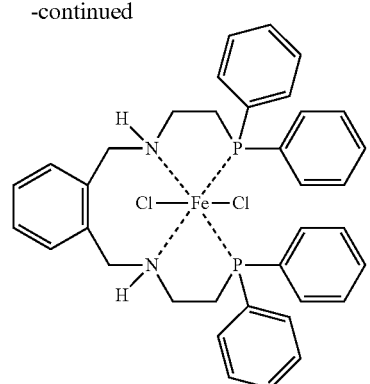

FeCl₂(1^B-1)

(Setup/Reaction)

A 50 mL four-necked round-bottom flask equipped with a magnetic stirring bar, condenser, thermometer and a three-way stopcock was evacuated and filled with nitrogen gas, a toluene solution of N,N'-[1,2-phenylenebis(methylene)]bis[2-(diphenylphosphino)ethylamine] (1^B-1) (purity: 20.00/0, 5.0 g, net weight: 1.0 g, 1.78 mmol, 1.1 equivalents) obtained in Example 5, dehydrated THF (10 mL) and iron(II) chloride (FeCl₂) (206 mg, 1.62 mmol, 1.0 equivalents) were charged into the flask successively. The obtained white suspension was heated by means of an oil bath and stirred with a magnetic stirrer for 3 hours under reflux (inner temperature: about 70° C.).

(Post Treatment/Isolation/Purification)

A cream-colored suspension obtained by cooling the reaction solution to room temperature was subjected to suction filtration under nitrogen stream. The crystals collected by filtration were washed with toluene (20 mL) and dried under reduced pressure to give 730 mg of title compound (FeCl₂(1^B-1)) as a white powder. Isolated yield: 65.6%.

HRMS: m/z=686.1219, M=C₃₆H₃₈Cl₂FeN₂P₂.

As a result of ¹H NMR measurement, a broad peak was observed over a wide range of −5 to 150 ppm, and therefore it was revealed that the title compound is paramagnetic. Furthermore, in the range of −150 to 250 ppm, no peak was observed by ³¹P NMR.

Example 24

Synthesis of dichloro{(1S,1'S)-N,N'-[1,2-phenylenebis(methylene)]bis[2-(diphenylphosphino)-1-phenyl-ethylamine]}iron(II) (Structural Formula (FeCl$_2$[(S,S)-1$^B$-3])) (Eq. 27)

[Chem. 47]

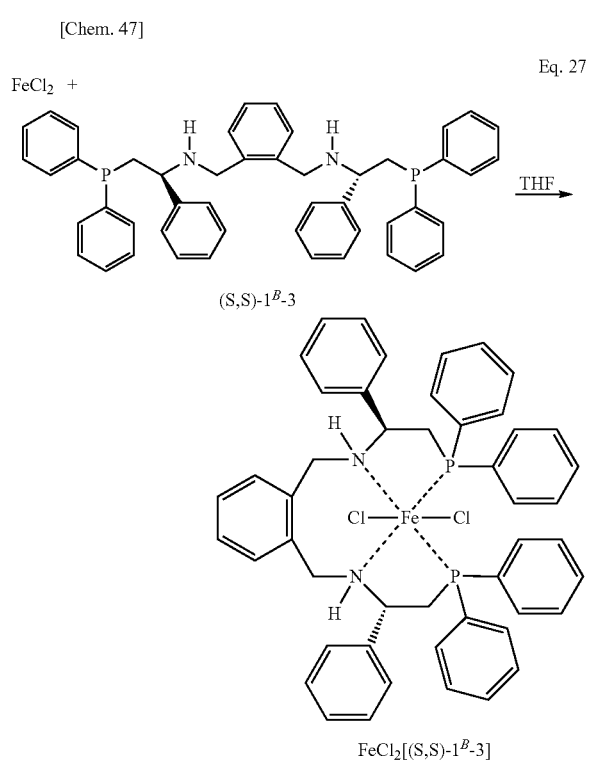

(Setup/Reaction)

A 50 mL four-necked round-bottom flask equipped with a magnetic stirring bar, condenser, thermometer and a three-way stopcock was evacuated and filled with nitrogen gas, (1S,1'S)-N,N'-[1,2-phenylenebis(methylene)]bis[2-diphenylphosphino)-1-phenyl-ethylamine] ((S,S)-1$^B$-3) (1.5 g, 2.10 mmol, 1.1 equivalents) obtained in Example 7, dehydrated THF (10 mL) and FeCl$_2$ (242 mg, 1.91 mmol, 1.0 equivalent) were charged into the flask successively. The obtained white suspension was heated by means of an oil bath and stirred with a magnetic stirrer for 3 hours under reflux (inner temperature: about 67° C.).

(Post Treatment/Isolation/Purification)

A cream-colored suspension obtained by the reaction was cooled to room temperature and diluted with dehydrated diethyl ether (20 mL), followed by suction filtration under nitrogen stream. The crystals collected by filtration were washed with diethyl ether (20 mL) and dried under reduced pressure to give 1.52 g of title compound (FeCl$_2$[(S,S)-1$^B$-3]) as a cream-colored powder. Isolated yield: 94.8%.

HRMS: m/z=838.1839, M=C$_{48}$H$_{46}$Cl$_2$FeN$_2$P$_2$.

As a result of $^1$H NMR measurement, a broad peak was observed over a wide range of −10 to 140 ppm, and therefore it was revealed that the title compound is paramagnetic. Furthermore, in the range of −150 to 250 ppm, no peak was observed by $^{31}$P NMR.

Example 25

Production (1) of Benzyl Alcohol by Catalytic Hydrogenation Reaction of Methyl Benzoate (Eq. 28)

[Chem. 48]

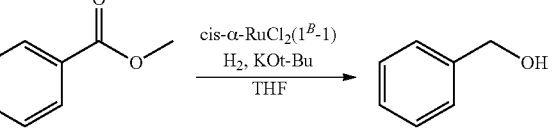

To a 100 mL stainless steel-made autoclave apparatus equipped with a glass-made inner tube and a magnetic stirring bar was charged cis-α-RuCl$_2$(1$^B$-1) (3.7 mg, 5.00 µmol, 0.1 mol %) obtained in Example 13 as a catalyst, and the inside of the apparatus was purged with nitrogen gas. Subsequently, dehydrated THF (5.0 mL) as a solvent, methyl benzoate (626 µL, 5.00 mmol, 1.0 equivalent), and a THF solution of potassium tert-butoxide (KOt-Bu) (concentration: 1.0 mol/L, 500 µL, 0.50 mmol, 0.1 equivalents) were charged into the apparatus successively. Furthermore, the inside of the apparatus was replaced by hydrogen gas and the hydrogen pressure was set to 1 MPa, followed by stirring with a magnetic stirrer at 80° C. for 5 hours to produce benzyl alcohol that is the title compound. Conversion: 93.2%, selectivity: 99.3% (according to GC analysis).

GC Retention time (measurement condition 1): methyl benzoate: 6.81 minutes, benzyl alcohol: 5.84 minutes.

Example 26

Production of Benzyl Alcohol by Catalytic Hydrogenation Reaction of Methyl Benzoate (2)

Benzyl alcohol was produced in the same manner as in Example 25 except that dehydrated toluene was used as the solvent. Conversion: 94.0%, selectivity: 98.7%.

Example 27

Production of Benzyl Alcohol by Catalytic Hydrogenation Reaction of Methyl Benzoate (3)

Benzyl alcohol was produced in the same manner as in Example 25 except that cis-β-RuCl$_2$(1$^B$-1) obtained in Example 14 was used as the catalyst. Conversion: 93.7%, selectivity: 99.1%.

Example 28

Production of Benzyl Alcohol by Catalytic Hydrogenation Reaction of Methyl Benzoate (4)

Benzyl alcohol was produced in the same manner as in Example 25 except that RuH(BH$_4$)(1$^B$-1) obtained in Example 16 was used as the catalyst, a THF solution of KOt-Bu as a base was not added, and the hydrogen pressure was set to 5 MPa. Conversion: >99.9%, selectivity: >99.9%.

Example 29

Production of Benzyl Alcohol by Catalytic Hydrogenation Reaction of Methyl Benzoate (5)

Benzyl alcohol was produced in the same manner as in Example 25 except that RuCl$_2$(1$^B$-6) obtained in Example 20 was used as the catalyst and the hydrogen pressure was set to 5 MPa. Conversion: 94.8%, selectivity: 98.7%.

The results of Examples 25 to 29 are shown together in Table 1 below.

TABLE 1

| Example | Catalyst | Hydrogen Pressure | Conversion | Selectivity | Remarks |
|---|---|---|---|---|---|
| 25 | cis-α-RuCl$_2$(1$^B$-1) | 1 MPa | 93.2% | 99.3% | |
| 26 | cis-α-RuCl$_2$(1$^B$-1) | 1 MPa | 94.0% | 98.7% | solvent: toluene |
| 27 | cis-β-RuCl$_2$(1$^B$-1) | 1 MPa | 93.7% | 99.1% | |
| 28 | RuH(BH$_4$)(1$^B$-1) | 5 MPa | >99.9% | >99.9% | no addition of KOt-Bu |
| 29 | RuCl$_2$(1$^B$-6) | 5 MPa | 94.8% | 98.7% | SNNS tetradentate ligand complex |

Among the transition metal complexes of the present invention, cis-α-RuCl$_2$(1$^B$-1) as a ruthenium complex having a PNNP tetradentate ligand gave benzyl alcohol by efficiently catalyzing the hydrogenation reaction of methyl benzoate, irrespective of the polarity of the reaction solvent, with a small catalyst amount of 0.1 mol % even in a low-pressure hydrogen gas atmosphere of 1 MPa (Examples 25 and 26).

Furthermore, cis-β-RuCl$_2$(1$^B$-1) differing in the coordination form also had excellent catalytic activity comparable to cis-α form (Example 27).

Accordingly, it is understood that these complexes have greatly enhanced catalytic activity, compared to a ruthenium complex having a conventional PNNP tetradentate ligand (Patent Document 1 and Non-Patent Document 1 described above).

In addition, RuH(BH$_4$)(1$^B$-1) obtained by chemical conversion of cis-α-RuCl$_2$(1$^B$-1) exhibited high catalytic activity even without addition of a base such as KOt-Bu (Example 28)

Moreover, among the transition metal complexes of the present invention, RuCl$_2$(1$^B$-6) as a ruthenium complex having an SNNS tetradentate ligand was proved to allow for efficient progress of hydrogenation reaction of esters having poorer reactivity than that of ketones, which was at all difficult with the conventional ruthenium complex having a conventional SNNS tetradentate ligand (Non-Patent Document 2 described above), though a high-pressure hydrogen gas of 5 MPa was required (Example 29).

Example 30

Production of Benzyl Alcohol by Catalytic Hydrogenation Reaction of Tert-Butyl Benzoate (Eq. 29)

[Chem. 49]

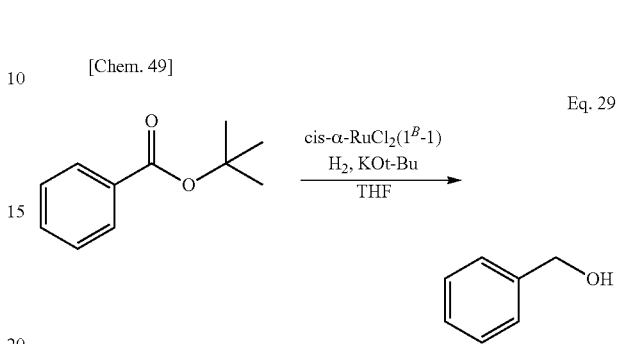

Eq. 29

To a 100 mL stainless steel-made autoclave apparatus equipped with a glass-made inner tube and a magnetic stirring bar was charged cis-α-RuCl$_2$(1$^B$-1) (3.7 mg, 5.00 μmol, 0.1 mol %) obtained in Example 13 as a catalyst, and the inside of the apparatus was purged with nitrogen gas. Subsequently, dehydrated THF (5.0 mL), tert-butyl benzoate (891 μL, 5.00 mmol, 1.0 equivalent) as a substrate, and a THF solution of KOt-Bu (concentration: 1.0 mol/L, 500 μL, 0.50 mmol, 0.1 equivalents) were charged into the apparatus successively. Furthermore, the inside of the apparatus was replaced by hydrogen gas and the hydrogen pressure was set to 5 MPa, followed by stirring with a magnetic stirrer at 100° C. for 5 hours to produce benzyl alcohol that is the title compound. Conversion: 100%, selectivity: 98.8% (according to GC analysis).

GC Retention time (measurement condition 1): tert-butyl benzoate: 9.02 minutes, benzyl alcohol: 5.73 minutes.

Example 31

Production of Benzyl Alcohol by Catalytic Hydrogenation Reaction of N,N-dimethylbenzamide (Eq. 30)

[Chem. 50]

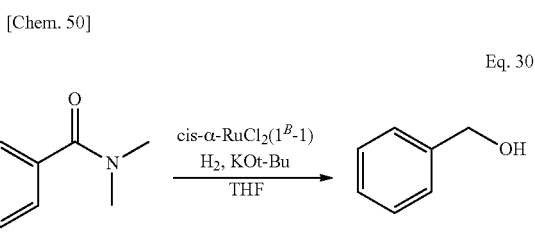

Eq. 30

Benzyl alcohol was produced in the same manner as in Example 30 except that N,N-dimethylbenzamide was used as the substrate, the catalyst amount was changed to 0.5 mol %, and the reaction temperature was set to 120° C. Conversion: 99.8%, selectivity: 96.0% (according to GC analysis).

GC Retention time (measurement condition 2): N,N-dimethylbenzamide: 10.56 minutes, benzyl alcohol: 6.15 minutes.

Example 32

Production of 4-Bromobenzyl Alcohol by Catalytic Hydrogenation Reaction of Methyl 4-bromobenzoate (Eq. 31)

[Chem. 51]

Eq. 31

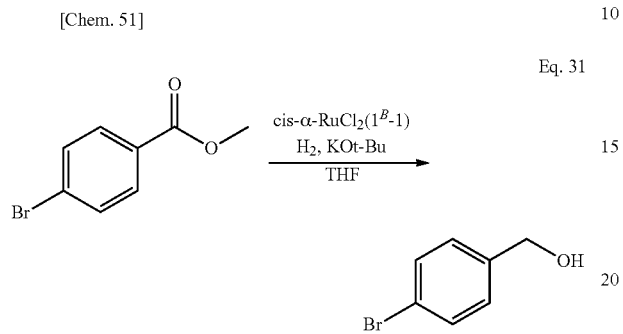

4-Bromobenzyl alcohol was produced in the same manner as in Example 30 except that methyl 4-bromobenzoate was used as the substrate and the reaction temperature was set to 80° C. Conversion: >99.9%, selectivity: 98.1% (according to GC analysis).

GC Retention time (measurement condition 2): methyl 4-bromobenzoate: 10.44 minutes, 4-bromobenzyl alcohol: 10.15 minutes.

The results of Examples 30 to 32 are shown together in Table 2 below.

TABLE 2

| Example | Substrate | Catalyst Amount | Reaction Temperature | Product | Conversion | Selectivity |
|---|---|---|---|---|---|---|
| 30 | tert-butyl benzoate | 0.1 mol % | 100° C. | benzyl alcohol | >99.9% | 98.8% |
| 31 | N,N-dimethyl-benzamide | 0.5 mol % | 120° C. | benzyl alcohol | 99.8% | 96.0% |
| 32 | methyl 4-bromo benzoate | 0.1 mol % | 80° C. | 4-bromo-benzyl alcohol | >99.9% | 98.1% |

In the hydrogenation reaction using cis-α-RuCl$_2$(1$^B$-1) that is the transition metal complex of the present invention as the catalyst, benzyl alcohol could be efficiently produced on high-pressure conditions even when tert-butyl benzoate having low reactivity because of its high bulkiness or N,N-dimethylbenzamide as amides having further poorer reactivity was used as the substrate (Examples 30 and 31). In addition, a hydrolysis of carbon-halogen bond often becomes a problem in the hydrogenation reaction of esters having a halogeno group generally. However, 4-bromobenzyl alcohol could be highly selectively produced from methyl 4-bromobenzoate when the technique of the present invention was used (Example 32).

Example 33

Production of (4E)-decen-1-ol by Catalytic Hydrogenation Reaction of Ethyl (4E)-decenoate (Eq. 32)

[Chem. 52]

Eq. 32

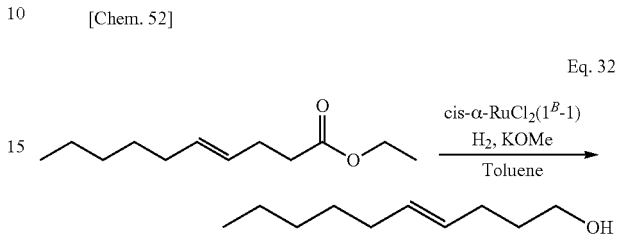

To a 100 mL stainless steel-made autoclave apparatus equipped with a glass-made inner tube and a magnetic stirring bar were charged cis-α-RuCl$_2$(1$^B$-1) (1.2 mg, 1.70 μmol, 0.033 mol %) obtained in Example 13 and potassium methoxide (KOMe) (105 mg, 1.50 mmol, 0.3 equivalents) successively, and f the inside of the apparatus was purged with nitrogen gas. Subsequently, dehydrated toluene (7.1 mL) and ethyl (4E)-decenoate (1.13 mL, 5.00 mmol, 1.0 equivalent) as a substrate were charged into the apparatus successively. Furthermore, the inside of the apparatus was replaced by hydrogen gas and the hydrogen pressure was set to 5 MPa, followed by stirring with a magnetic stirrer at 100° C. for 5 hours to produce (4E)-decen-1-ol that is the title compound. Conversion: >99.9%, selectivity: 99.3% (according to GC analysis).

GC Retention time (measurement condition 2): ethyl (4E)-decenoate: 11.03 minutes, (4E)-decen-1-ol: 9.41 minutes.

Example 34

Production of Oleyl Alcohol by Catalytic Hydrogenation Reaction of Methyl Oleate (Eq. 33)

[Chem. 53]

Eq. 33

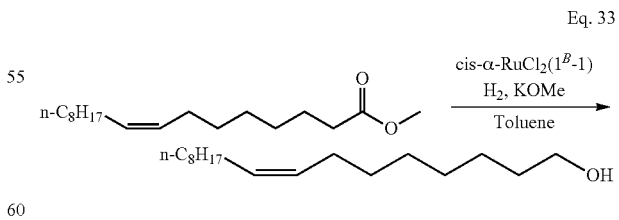

Oleyl alcohol was produced in the same manner as in Example 33 except that methyl oleate was used as the substrate. Conversion: 99.4%, selectivity: 97.1% (according to GC analysis).

GC Retention time (measurement condition 2): methyl oleate: 18.69 minutes, oleyl alcohol: 18.35 minutes.

Example 35

Production of Linoleyl Alcohol by Catalytic Hydrogenation Reaction of Methyl Linoleate (Eq. 34)

[Chem. 54]

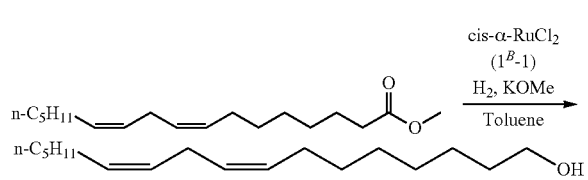

Eq. 34

Linoleyl alcohol was produced in the same manner as in Example 33 except that methyl linoleate was used as the substrate. Conversion: 93.5%, selectivity: 92.6% (according to GC analysis).

GC Retention time (measurement condition 2): methyl linoleate: 18.61 minutes, linoleyl alcohol: 18.24 minutes.

The results of Examples 33 to 35 are shown together in Table 3 below.

TABLE 3

| Example | Substrate | Product | Conversion | Selectivity |
|---|---|---|---|---|
| 33 | ethyl (4E)-decenoate | (4E)-decen-1-ol | >99.9% | 99.3% |
| 34 | methyl oleate | oleyl alcohol | 99.4% | 97.1% |
| 35 | methyl linoleate | linoleyl alcohol | 93.5% | 92.6% |

Generally, by-production of saturated alcohols often becomes a problem in the hydrogenation reaction of unsaturated esters. However, industrially useful unsaturated alcohols could be highly selectively produced from unsaturated esters when cis-α-RuCl$_2$(1$^B$-1) that is the transition metal complex of the present invention was used as the catalyst in the reaction above.

Example 36

Production of tert-butyl(4-hydroxybutan-2-yl)carbamate by Catalytic Hydrogenation Reaction of Methyl 3-[(tert-butoxycarbonyl)amino]butyrate Under Neutral Conditions (Eq. 35)

[Chem. 55]

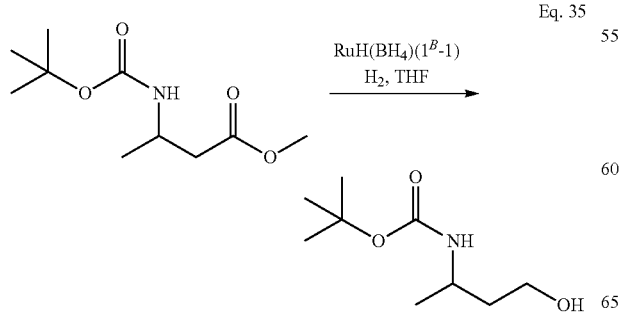

Eq. 35

To a 50 mL stainless steel-made autoclave apparatus equipped with a glass-made inner tube and a magnetic stirring bar were charged RuH(BH$_4$)(1$^B$-1) (6.8 mg, 10.0 μmol, 0.5 mol %) obtained in Example 16 and methyl 3-[(tert-butoxycarbonyl)amino]butyrate (435 mg, 2.00 mmol, 1.0 equivalent) successively. After purging the inside of the apparatus with nitrogen gas, dehydrated THF (4.0 mL) was further charged. Subsequently, the inside of the apparatus was replaced by hydrogen gas and the hydrogen pressure was set to 5 MPa, followed by stirring with a magnetic stirrer at 100° C. for 7 hours to produce tert-butyl (4-hydroxybutan-2-yl)carbamate that is the title compound. Conversion: >99.9%, selectivity: 99.6% (according to GC analysis).

GC Retention time (measurement condition 2): methyl 3-[(tert-butoxycarbonyl)amino]butyrate: 10.60 minutes, tert-butyl(4-hydroxybutan-2-yl)carbamate: 10.12 minutes.

Example 37

Production of 1,4-butanediol by Catalytic Hydrogenation Reaction of γ-butyrolactone Under Neutral Conditions (Eq. 36)

[Chem. 56]

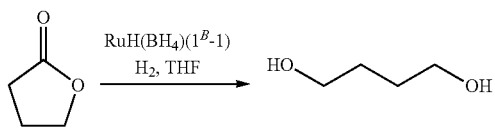

Eq. 36

To a 100 mL stainless steel-made autoclave apparatus equipped with a glass-made inner tube and a magnetic stirring bar was charged RuH(BH$_4$)(1$^B$-1) (3.4 mg, 5.00 μmol, 0.1 mol %) obtained in Example 16, and the inside of the apparatus was purged with nitrogen gas. Subsequently, dehydrated THF (5.0 mL) and γ-butyrolactone (381 μL, 5.00 mmol, 1.0 equivalent) were charged into the apparatus successively. The inside of the apparatus was then replaced by hydrogen gas and the hydrogen pressure was set to 5 MPa, followed by stirring with a magnetic stirrer at 80° C. for 5 hours to produce 1,4-butanediol that is the title compound. Conversion: 98.0%, selectivity: 99.3% (according to GC analysis).

GC Retention time (measurement condition 2): γ-butyrolactone: 4.24 minutes, 1,4-butanediol: 4.89 minutes.

Example 38

Synthesis of Benzylamine by Catalytic Hydrogenation Reaction of Benzonitrile (Eq. 37)

[Chem. 57]

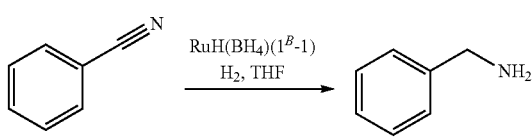

Eq. 37

To a 100 mL stainless steel-made autoclave apparatus equipped with a glass-made inner tube and a magnetic stirring bar was charged RuH(BH$_4$)($1^B$-1) (6.1 mg, 9.0 µmol, 0.1 mol %) obtained in Example 16 as a catalyst, and the inside of the apparatus was purged with nitrogen gas. Subsequently, dehydrated THF (3.0 mL) and benzonitrile (923 µL, 9.00 mmol, 1.0 equivalent) as a substrate were charged into the apparatus successively. The inside of the apparatus was then replaced by hydrogen gas and the hydrogen pressure was set to 5 MPa, followed by stirring with a magnetic stirrer at 110° C. for 5 hours to produce benzylamine that is the title compound. Conversion: >99.9%, selectivity: 94.3% (according to GC analysis).

GC Retention time (measurement condition 2): benzonitrile: 5.49 minutes, benzylamine: 5.87 minutes.

Example 39

Production of 1-octylamine by Catalytic Hydrogenation Reaction of 1-octanenitrile (Eq. 38)

[Chem. 58]

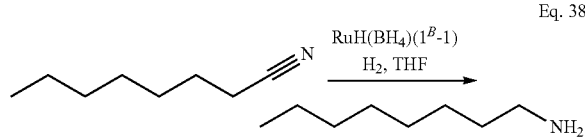

Eq. 38

1-Octylamine was produced in the same manner as in Example 38 except that 1-octanenitrile was used as the substrate and the catalyst amount was changed to 0.2 mol %. Conversion: 99.8%, selectivity: 99.9% (according to GC analysis).

GC Retention time (measurement condition 2): 1-octanenitrile: 6.67 minutes, 1-octylamine: 6.46 minutes.

The results of Examples 36 to 39 are shown together in Table 4 below.

TABLE 4

| Example | Substrate | Catalyst Amount | Product | Conversion | Selectivity |
|---|---|---|---|---|---|
| 36 | methyl 3-[(tert-butoxy-carbonyl)amino]butyrate | 0.5 mol % | tert-butyl(4-hydroxybutan-2-yl)carbamate | >99.9% | 99.6% |
| 37 | γ-butyrolactone | 0.1 mol % | 1,4-butanediol | 98.0% | 99.3% |
| 38 | benzonitrile | 0.1 mol % | benzylamine | >99.9% | 94.3% |
| 39 | 1-octanenitrile | 0.2 mol % | 1-octylamine | 99.8% | 99.9% |

As demonstrated in Example 28, RuH(BH$_4$)($1^B$-1) that is the transition metal complex of the present invention exhibits high catalytic activity even under neutral conditions and therefore, functionalized primary alcohols or diols could be highly selectively produced from esters or lactones having a functional group unstable to basic conditions when the hydrogenation reaction was performed using the complex as the catalyst (Examples 36 and 37). In addition, by-production of secondary amines generally becomes a problem at the time of production of primary amines by a hydrogenation reaction of nitriles. However, primary amines could be highly selectively produced when the reaction was performed under neutral conditions by using RuH(BH$_4$)($1^B$-1) that is the transition metal complex of the present invention (Examples 38 and 39).

While the present invention has been described in detail and with reference to specific embodiments thereof, it will be apparent to one skilled in the art that various changes and modifications can be made therein without departing from the spirit and scope of the present invention. This application is based on Japanese Patent Application (Patent Application No. 2016-067534) filed on Mar. 30, 2016, the contents of which are incorporated herein by way of reference.

INDUSTRIAL APPLICABILITY

The compound ($1^A$) of the present invention can be efficiently produced by the reaction of compound ($2^A$) and compound (3). Furthermore, the compound ($1^A$) of the present invention acts as a tetradentate ligand and therefore, the transition metal complex of the present invention having excellent catalytic activity in a variety of organic synthesis reactions can be easily produced by the reaction thereof with various transition metal compounds.

Furthermore, compared with conventional transition metal complexes such as a ruthenium complex having a 2-diphenylphosphinobenzaldehyde-ethylene diamine dehydrative condensate as a PNNP tetradentate ligand or a ruthenium complex having a 2-alkylthiobenzaldehyde-ethylene diamine dehydrative condensate as an SNNS tetradentate ligand, the transition metal complex of the present invention exhibits more excellent catalytic activity in a hydrogenation reaction of esters and therefore, primary alcohols can be efficiently produced by this catalytic reaction.

In addition, not only primary alcohols but also useful compounds such as halogenated alcohols, unsaturated alcohols, diols, and primary amines can be produced with high selectivity and high yield when a hydrogenation reaction of amides, halogenated esters, unsaturated esters, lactones, and nitriles is performed by using the transition metal complex of the present invention as a catalyst.

The invention claimed is:
1. A compound represented by the following formula ($1^A$):

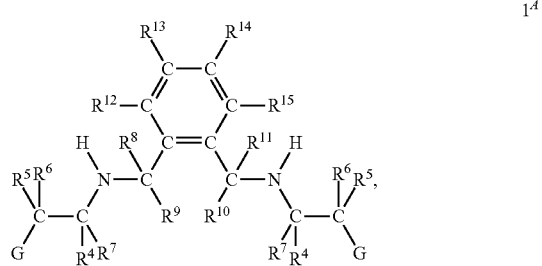

$1^A$ wherein the solid lines represent a single bonds and the double lines represent double bonds, C represents a carbon atom, H represents a hydrogen atom and N represents a nitrogen atom, each of $R^4$, $R^5$, $R^6$, $R^7$, $R^8$, $R^9$, $R^{10}$, $R^{11}$, $R^{12}$, $R^{13}$, $R^{14}$, and $R^{15}$ independently represents a group selected from the group consisting of a hydrogen atom, an alkyl group, a cycloalkyl group, an aryl group, and an aralkyl group, and G represents a group selected from the group consisting of a monovalent group represented by the following formula ($G^F$) and a monovalent group represented by the following formula ($G^S$):

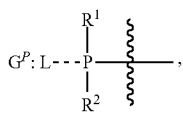

wherein the solid lines represent a single bonds, a dotted line represents a coordinate bond and a solid line intersected by a wavy line represents a bond to an adjacent atom, P represents a phosphorus atom, L represents a lone electron pair or a boron trihydride, each of $R^1$ and $R^2$ independently represents a group selected from the group consisting of an alkyl group, a cycloalkyl group, an alkenyl group, an aryl group, a heteroaryl group, and an aralkyl group, and $R^1$ and $R^2$ may combine with each other to form a phosphorus atom-containing ring; and

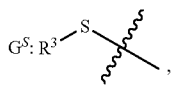

wherein a solid line represents a single bond and a solid line intersected by a wavy line represents a bond to an adjacent atom, S represents a sulfur atom, and $R^3$ represents a group selected from the group consisting of an alkyl group, a cycloalkyl group, an alkenyl group, an aryl group, a heteroaryl group, and an aralkyl group; and an alkenyl group in $R^1$ to $R^3$, an aryl group in $R^1$ to $R^3$, a heteroaryl group in $R^1$ to $R^3$, an aralkyl group in $R^1$ to $R^3$, and a phosphorus atom-containing ring formed by combining $R^1$ with $R^2$ each other may be substituted by a substituent selected from the group consisting of an alkyl group, a cycloalkyl group, a halogenoalkyl group, an aryl group, an aralkyl group, an alkoxy group, a silyl group, and a halogeno group.

2. The compound according to claim 1, wherein all of the $R^5$ to $R^{15}$ are hydrogen atoms.

3. The compound according to claim 1, which is an optically active substance.

4. A method for producing the compound according to claim 1, comprising subjecting a compound represented by the following formula ($2^A$) to a reaction with a compound represented by the following formula (3):

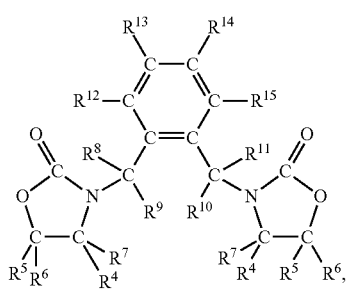

wherein the solid lines represent single bonds and double lines represent double bonds, C represents a carbon atom, N represents a nitrogen atom, O represents an oxygen atom, and each of $R^4$, $R^5$, $R^6$, $R^7$, $R^8$, $R^9$, $R^{10}$, $R^{11}$, $R^{12}$, $R^{13}$, $R^{14}$, and $R^{15}$ independently represents a group selected from the group consisting of a hydrogen atom, an alkyl group, a cycloalkyl group, an aryl group, and an aralkyl group; and

wherein the solid line represents a single bond, H represents a hydrogen atom, and G represents the same group as G defined in claim 1.

5. A compound represented by the following formula ($2^A$):

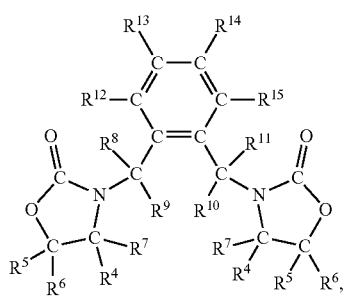

wherein the solid lines represent single bonds and double lines represent double bonds, C represents a carbon atom, N represents a nitrogen atom, O represents an oxygen atom, and each of $R^4$, $R^5$, $R^6$, $R^7$, $R^8$, $R^9$, $R^{10}$, $R^{11}$, $R^{12}$, $R^{13}$, $R^{14}$, and $R^{15}$ independently represents a group selected from the group consisting of a hydrogen atom, an alkyl group, a cycloalkyl group, an aryl group, and an aralkyl group.

6. The compound according to claim 5, wherein all of the $R^5$ to $R^{15}$ are hydrogen atoms.

7. The compound according to claim 5, which is an optically active substance.

8. A ruthenium complex comprising the compound according to claim 1 as a ligand.

9. An iron complex comprising the compound according to claim 1 as a ligand.

* * * * *